US012779084B2

(12) United States Patent
Brown et al.

(10) Patent No.: US 12,779,084 B2
(45) Date of Patent: Nov. 3, 2026

(54) BRAIDED SURGICAL IMPLANTS

(71) Applicant: Embody, Inc., Norfolk, VA (US)

(72) Inventors: Robert S. Brown, Norfolk, VA (US); Caitlin Harclerode, Norfolk, VA (US); Nardos Sori, Norfolk, VA (US); Michael P. Francis, Norfolk, VA (US); Nicholas Thayer, Morrisville, NC (US)

(73) Assignee: Embody, Inc., Norfolk, VA (US)

( * ) Notice: Subject to any disclaimer, the term of this patent is extended or adjusted under 35 U.S.C. 154(b) by 545 days.

(21) Appl. No.: 18/167,051

(22) Filed: Feb. 9, 2023

(65) Prior Publication Data

US 2023/0263932 A1 Aug. 24, 2023

Related U.S. Application Data

(63) Continuation-in-part of application No. 17/162,568, filed on Jan. 29, 2021, now abandoned.

(60) Provisional application No. 62/968,873, filed on Jan. 31, 2020.

(51) Int. Cl.

*A61L 17/14* (2006.01)
*A61L 17/08* (2006.01)
*A61L 17/10* (2006.01)

(52) U.S. Cl.

CPC ............... *A61L 17/14* (2013.01); *A61L 17/08* (2013.01); *A61L 17/105* (2013.01)

(58) Field of Classification Search

CPC ......... A61L 17/14; A61L 17/08; A61L 17/105
See application file for complete search history.

(56) References Cited

U.S. PATENT DOCUMENTS

| | | | |
|---|---|---|---|
| 1,254,031 | A | 1/1918 | Davis |
| 2,598,608 | A | 5/1952 | Salo et al. |
| 2,748,774 | A | 6/1956 | Novak |
| 2,750,251 | A | 6/1956 | Alfred et al. |
| 3,114,591 | A | 12/1963 | Joseph et al. |
| 3,366,440 | A | 1/1968 | Nuwayser |
| 3,534,740 | A | 10/1970 | Thompson |
| 3,565,077 | A | 2/1971 | Glick |
| 3,926,194 | A | 12/1975 | Greenberg et al. |
| 3,949,756 | A | 4/1976 | Ace |
| 3,963,031 | A | 6/1976 | Hunter |
| 3,980,177 | A | 9/1976 | Mcgregor |
| 4,772,288 | A | 9/1988 | Borner et al. |

(Continued)

FOREIGN PATENT DOCUMENTS

| | | | |
|---|---|---|---|
| AU | 2021213237 | B2 | 4/2024 |
| CN | 1596996 | A | 3/2005 |

(Continued)

OTHER PUBLICATIONS

"U.S. Appl. No. 17/162,568, Non Final Office Action mailed Sep. 9, 2024", 13 pgs.

(Continued)

*Primary Examiner* — Yashita Sharma
*Assistant Examiner* — Aren Patel
(74) *Attorney, Agent, or Firm* — SCHWEGMAN LUNDBERG & WOESSNER, P.A.

(57) ABSTRACT

An implantable biopolymer scaffold includes at least one braided strand comprising high strength collagen fibers and synthetic fibers, wherein the collagen fibers have a greater cross-sectional deform ability than the synthetic fibers.

20 Claims, 56 Drawing Sheets

(56) References Cited

U.S. PATENT DOCUMENTS 5,078,744 A 1/1992 Chvapil
5,156,788 A 10/1992 Chesterfield et al.
5,171,273 A 12/1992 Silver et al.
5,195,542 A 3/1993 Gazielly et al.
5,374,278 A 12/1994 Chesterfield et al.
5,378,469 A 1/1995 Kemp et al.
5,412,068 A 5/1995 Tang et al.
5,441,508 A 8/1995 Gazielly et al.
5,458,636 A 10/1995 Brancato
5,486,593 A 1/1996 Tang et al.
5,496,371 A 3/1996 Eppley et al.
5,658,516 A 8/1997 Eppley et al.
5,697,969 A 12/1997 Schmitt et al.
5,733,337 A 3/1998 Carr, Jr. et al.
6,051,750 A 4/2000 Bell
6,179,872 B1 1/2001 Bell
6,390,096 B1 5/2002 Conrad et al.
6,398,819 B1 6/2002 Bell
6,450,989 B2 9/2002 Dubrul et al.
6,578,580 B2 6/2003 Conrad et al.
6,596,296 B1 7/2003 Nelson et al.
6,689,153 B1 2/2004 Skiba
6,716,234 B2 4/2004 Grafton et al.
6,755,863 B2 6/2004 Ferree
6,852,330 B2 2/2005 Bowman et al.
6,858,222 B2 2/2005 Nelson et al.
6,994,719 B2 2/2006 Grafton
7,029,490 B2 4/2006 Grafton et al.
7,033,603 B2 4/2006 Nelson et al.
7,060,103 B2 6/2006 Carr, Jr. et al.
7,153,312 B1 12/2006 Torrie et al.
7,235,295 B2 6/2007 Laurencin et al.
7,237,553 B2 7/2007 Knudson et al.
7,326,200 B2 2/2008 Trieu et al.
7,514,095 B2 4/2009 Nelson et al.
7,601,172 B2 10/2009 Segal et al.
7,803,395 B2 9/2010 Datta et al.
7,819,918 B2 10/2010 Malaviya et al.
7,824,701 B2 11/2010 Binette et al.
7,862,831 B2 1/2011 Wang et al.
7,878,786 B2 2/2011 Yost et al.
7,887,551 B2 2/2011 Bojarski et al.
7,892,256 B2 2/2011 Grafton et al.
7,909,886 B2 3/2011 Carr, Jr. et al.
7,963,972 B2 6/2011 Foerster et al.
8,012,172 B2 9/2011 Grafton et al.
8,048,361 B2 11/2011 Wang et al.
8,062,654 B2 11/2011 Nelson et al.
8,084,428 B2 12/2011 Spector et al.
8,092,529 B2 1/2012 Malaviya et al.
8,177,839 B2 5/2012 Koob et al.
8,241,654 B2 8/2012 Stopek
8,304,595 B2 11/2012 Daniels et al.
8,319,002 B2 11/2012 Daniels et al.
8,323,351 B2 12/2012 Kubena et al.
8,333,803 B2 12/2012 Park et al.
8,348,988 B2 1/2013 Lad et al.
8,353,938 B2 1/2013 Trieu et al.
8,367,148 B2 2/2013 Greenhalgh et al.
8,383,188 B2 2/2013 Mazzocca et al.
8,409,270 B2 4/2013 Clerc et al.
8,486,143 B2 7/2013 Laurencin et al.
8,491,457 B2 7/2013 Atala et al.
8,585,753 B2 11/2013 Scanlon et al.
8,586,345 B2 11/2013 Simpson et al.
8,608,758 B2 12/2013 Singhatat et al.
8,628,573 B2 1/2014 Roller et al.
8,637,066 B2 1/2014 Binnette et al.
8,691,542 B2 4/2014 Guilak et al.
8,697,044 B2 4/2014 Schroeder et al.
8,747,468 B2 6/2014 Martin et al.
8,790,699 B2 7/2014 Lauritzen et al.
8,852,265 B2 10/2014 Clerc et al.
8,870,915 B2 10/2014 Mayer et al.
8,986,378 B2 3/2015 Koob
9,005,285 B2 4/2015 Niu et al.
9,017,404 B2 4/2015 Champagne et al.
9,034,239 B2 5/2015 Yun et al.
9,125,759 B2 9/2015 Greenhalgh et al.
9,179,950 B2 11/2015 Zajac et al.
9,179,976 B2 11/2015 Paulos et al.
9,186,432 B2 11/2015 Mazzocca et al.
9,198,750 B2 12/2015 Van Kampen et al.
9,216,077 B2 12/2015 Davis et al.
9,233,187 B2 1/2016 Chun et al.
9,273,191 B2 3/2016 Ladet et al.
9,326,841 B2 5/2016 Martin et al.
9,370,381 B2 6/2016 Lu et al.
9,387,280 B2 7/2016 Brunelle et al.
9,393,104 B2 7/2016 Kampen et al.
9,408,636 B2 8/2016 Lu et al.
9,421,086 B2 8/2016 Roller et al.
9,421,305 B2 8/2016 Lee et al.
9,421,306 B2 8/2016 Park et al.
9,433,489 B2 9/2016 Reilly et al.
9,511,171 B2 12/2016 Binette et al.
9,511,175 B2 12/2016 Ladet et al.
9,539,084 B2 1/2017 Champagne et al.
9,555,155 B2 1/2017 Ganatra et al.
9,597,430 B2 3/2017 Ratcliffe et al.
9,610,151 B2 4/2017 Niu et al.
9,636,209 B2 5/2017 Koob et al.
9,642,891 B2 5/2017 Hart et al.
9,683,011 B2 6/2017 Wnek et al.
9,694,106 B2 7/2017 Brown et al.
9,757,120 B2 9/2017 Mayer et al.
9,757,121 B2 9/2017 Mayer et al.
9,757,132 B2 9/2017 Laurencin et al.
9,771,410 B2 9/2017 Lauritzen et al.
9,801,742 B2 10/2017 Clerc et al.
9,801,978 B2 10/2017 Paulos et al.
9,821,089 B2 11/2017 Haj-Ali et al.
9,873,861 B2 1/2018 Koob
9,943,393 B2 4/2018 Martin et al.
9,968,431 B2 5/2018 Martin et al.
10,022,231 B2 7/2018 Estes et al.
10,149,918 B2 12/2018 Davis et al.
10,149,923 B2 12/2018 Carter
10,206,686 B2 2/2019 Swayze et al.
10,231,821 B2 3/2019 Gabriele et al.
10,238,773 B2 3/2019 Li et al.
10,251,686 B2 4/2019 Zajac et al.
10,285,801 B2 5/2019 Roller et al.
10,493,180 B2 12/2019 Brunelle et al.
10,524,895 B2 1/2020 Zheng
10,532,127 B2 1/2020 Limem et al.
10,542,972 B2 1/2020 Mayer et al.
10,595,983 B1 3/2020 Ferguson et al.
10,603,408 B2 3/2020 Binette et al.
10,653,514 B2 5/2020 Koob et al.
10,660,638 B2 5/2020 Gedet et al.
10,689,621 B2 6/2020 Koob
10,716,876 B2 7/2020 Shoseyov et al.
10,745,855 B2 8/2020 Jessup et al.
10,758,644 B2 9/2020 Derwin et al.
10,792,393 B2 10/2020 Derwin et al.
10,813,763 B2 10/2020 Schlachter
10,864,028 B2 12/2020 Zajac et al.
2002/0090725 A1 7/2002 Simpson et al.
2002/0100725 A1 8/2002 Lee et al.
2002/0127265 A1 9/2002 Bowman et al.
2003/0105528 A1 6/2003 Shimp et al.
2003/0114937 A1 6/2003 Leatherbury et al.
2004/0199208 A1 10/2004 Foerster
2005/0008675 A1 1/2005 Bhatia et al.
2005/0033362 A1 2/2005 Grafton
2005/0055051 A1 3/2005 Grafton
2005/0113938 A1 5/2005 Jamiolkowski et al.
2006/0079596 A1 4/2006 Schroeder et al.
2006/0154063 A1 7/2006 Fujihara et al.
2006/0195011 A1* 8/2006 Arnal .................... A61F 2/0063
600/30
2006/0204539 A1 9/2006 Atala et al.
2006/0247641 A1 11/2006 Re et al.

(56) References Cited

U.S. PATENT DOCUMENTS

| | | | |
|---|---|---|---|
| 2007/0041952 | A1 | 2/2007 | Guilak et al. |
| 2007/0156174 | A1 | 7/2007 | Kaiser et al. |
| 2007/0190108 | A1 | 8/2007 | Datta et al. |
| 2007/0203564 | A1 | 8/2007 | Rusk et al. |
| 2007/0260279 | A1 | 11/2007 | Hotter et al. |
| 2007/0269481 | A1 | 11/2007 | Li et al. |
| 2007/0288023 | A1 | 12/2007 | Pellegrino et al. |
| 2008/0051809 | A1 | 2/2008 | Verhelst et al. |
| 2008/0051888 | A1 | 2/2008 | Ratcliffe et al. |
| 2008/0188936 | A1 | 8/2008 | Ball et al. |
| 2009/0098175 | A1 | 4/2009 | Buehrer et al. |
| 2009/0143819 | A1 | 6/2009 | D Agostino |
| 2009/0163951 | A1 | 6/2009 | Simmons et al. |
| 2009/0202430 | A1 | 8/2009 | Hoemann et al. |
| 2009/0202616 | A1 | 8/2009 | Chong et al. |
| 2009/0222039 | A1 | 9/2009 | Dreyfuss et al. |
| 2009/0240342 | A1 | 9/2009 | Lindh, Sr. et al. |
| 2010/0063599 | A1 | 3/2010 | Brunelle et al. |
| 2010/0075020 | A1 | 3/2010 | Reinprecht |
| 2010/0145367 | A1 | 6/2010 | Ratcliffe |
| 2010/0191332 | A1 | 7/2010 | Euteneuer et al. |
| 2010/0280532 | A1 | 11/2010 | Gingras |
| 2010/0291058 | A1 | 11/2010 | Bowlin et al. |
| 2010/0292791 | A1* | 11/2010 | Lu .......................... A61P 37/06 623/13.12 |
| 2010/0292792 | A1* | 11/2010 | Stone ........................ A61F 2/08 623/13.14 |
| 2010/0331980 | A1 | 12/2010 | Lee et al. |
| 2011/0022086 | A1 | 1/2011 | D Agostino et al. |
| 2011/0224702 | A1 | 9/2011 | Van Kampen et al. |
| 2011/0238178 | A1 | 9/2011 | Downes et al. |
| 2011/0270399 | A1 | 11/2011 | Yurek et al. |
| 2011/0293685 | A1 | 12/2011 | Kuo et al. |
| 2012/0093877 | A1 | 4/2012 | Zheng |
| 2012/0273993 | A1 | 11/2012 | Shoseyov et al. |
| 2012/0277863 | A1 | 11/2012 | Allinson et al. |
| 2013/0018463 | A1 | 1/2013 | Haddad et al. |
| 2013/0095078 | A1 | 4/2013 | Malcuit et al. |
| 2013/0095167 | A1 | 4/2013 | Warnke |
| 2013/0149532 | A1 | 6/2013 | Yun et al. |
| 2014/0005797 | A1 | 1/2014 | Park et al. |
| 2014/0011416 | A1 | 1/2014 | Yang et al. |
| 2014/0051169 | A1 | 2/2014 | Ganey et al. |
| 2014/0112973 | A1 | 4/2014 | Steinberg et al. |
| 2014/0148827 | A1 | 5/2014 | Odermatt et al. |
| 2014/0188212 | A1* | 7/2014 | Haselby .................... A61F 2/07 623/1.15 |
| 2014/0243891 | A1* | 8/2014 | Schmieding ....... A61B 17/0493 606/228 |
| 2014/0288634 | A1 | 9/2014 | Shalev |
| 2015/0045454 | A1 | 2/2015 | Kong et al. |
| 2015/0081000 | A1 | 3/2015 | Hossainy et al. |
| 2015/0086607 | A1 | 3/2015 | Johnson et al. |
| 2015/0230913 | A1 | 8/2015 | Derwin et al. |
| 2015/0230918 | A1 | 8/2015 | Detamore et al. |
| 2015/0367030 | A1 | 12/2015 | Murray |
| 2016/0015852 | A1 | 1/2016 | Liou et al. |
| 2016/0022865 | A1 | 1/2016 | Francis et al. |
| 2016/0045296 | A1 | 2/2016 | Guo |
| 2016/0067372 | A1 | 3/2016 | Davis et al. |
| 2016/0068654 | A1 | 3/2016 | Huh et al. |
| 2016/0106548 | A1 | 4/2016 | Li et al. |
| 2016/0130558 | A1 | 5/2016 | Baer |
| 2016/0136895 | A1 | 5/2016 | Beyer et al. |
| 2016/0199537 | A1 | 7/2016 | Koob |
| 2016/0263280 | A1 | 9/2016 | Harrell |
| 2016/0279219 | A1 | 9/2016 | Mooney et al. |
| 2016/0279301 | A1 | 9/2016 | He et al. |
| 2016/0287374 | A1 | 10/2016 | Soletti et al. |
| 2016/0296627 | A1 | 10/2016 | Garcia et al. |
| 2016/0317281 | A1 | 11/2016 | Van Kampen et al. |
| 2016/0325013 | A1 | 11/2016 | Li et al. |
| 2016/0325022 | A1 | 11/2016 | Liu et al. |
| 2016/0345674 | A1 | 12/2016 | Bruce et al. |
| 2017/0189163 | A1 | 7/2017 | Koob et al. |
| 2017/0202920 | A1 | 7/2017 | Hart et al. |
| 2017/0233834 | A1 | 8/2017 | Purcell et al. |
| 2017/0246351 | A1 | 8/2017 | Murthy et al. |
| 2017/0273680 | A1 | 9/2017 | Sengun et al. |
| 2017/0273775 | A1 | 9/2017 | Rocco et al. |
| 2017/0296328 | A1 | 10/2017 | Albertorio et al. |
| 2018/0168791 | A1* | 6/2018 | Gorman ................ A61F 2/0063 |
| 2018/0177921 | A1 | 6/2018 | Paulos et al. |
| 2018/0193524 | A1 | 7/2018 | Shoseyov et al. |
| 2018/0280567 | A1 | 10/2018 | Kohn et al. |
| 2018/0289490 | A1 | 10/2018 | Estes et al. |
| 2018/0360914 | A1 | 12/2018 | Hart et al. |
| 2018/0368982 | A1 | 12/2018 | Ball |
| 2019/0151074 | A1 | 5/2019 | Gabriele et al. |
| 2019/0175170 | A1 | 6/2019 | Yagnik et al. |
| 2019/0184062 | A1 | 6/2019 | Park et al. |
| 2019/0275207 | A1 | 9/2019 | Park et al. |
| 2019/0343985 | A1 | 11/2019 | Zreiqat et al. |
| 2019/0367733 | A1 | 12/2019 | Frampton, IV |
| 2020/0022701 | A1 | 1/2020 | Crook et al. |
| 2020/0046872 | A1* | 2/2020 | Wan ........................ A61L 17/08 |
| 2020/0113670 | A1 | 4/2020 | Zheng |
| 2020/0121316 | A1 | 4/2020 | Mayer et al. |
| 2020/0171205 | A1 | 6/2020 | Tod |
| 2020/0215228 | A1 | 7/2020 | Coulombe et al. |
| 2020/0237498 | A1 | 7/2020 | Koob et al. |
| 2020/0246505 | A1 | 8/2020 | Francis et al. |
| 2020/0306029 | A1 | 10/2020 | Rocco et al. |
| 2020/0316255 | A1 | 10/2020 | Ginn et al. |
| 2020/0332463 | A1 | 10/2020 | Jessup et al. |
| 2021/0000603 | A1 | 1/2021 | Schlachter |
| 2021/0275716 | A1 | 9/2021 | Francis et al. |
| 2023/0000481 | A1* | 1/2023 | Best ...................... A61F 2/0811 |
| 2025/0170296 | A1 | 5/2025 | Brown et al. |
| 2026/0069742 | A1 | 3/2026 | Francis et al. |

FOREIGN PATENT DOCUMENTS

| | | | |
|---|---|---|---|
| CN | 104606713 | A | 5/2015 |
| CN | 107261210 | A | 10/2017 |
| CN | 115315277 | A | 11/2022 |
| EP | 1216296 | B1 | 4/2009 |
| EP | 1504773 | B1 | 10/2009 |
| EP | 2322234 | B1 | 8/2013 |
| EP | 2774546 | A1 | 9/2014 |
| EP | 1863547 | B1 | 5/2016 |
| EP | 4096729 | A1 | 12/2022 |
| FR | 2800595 | B1 | 1/2002 |
| JP | 2008508003 | A | 3/2008 |
| JP | 2010540791 | A | 12/2010 |
| JP | 2010540792 | A | 12/2010 |
| JP | 2011506787 | A | 3/2011 |
| JP | 2015511502 | A | 4/2015 |
| JP | 2015200055 | A | 11/2015 |
| JP | 2023512211 | A | 3/2023 |
| JP | 7489599 | B2 | 5/2024 |
| JP | 2024113667 | A | 8/2024 |
| WO | WO-9830252 | A1 | 7/1998 |
| WO | WO-9939724 | A1 | 8/1999 |
| WO | WO-03043486 | A2 | 5/2003 |
| WO | WO-2007109304 | A2 | 9/2007 |
| WO | WO-2008131293 | A2 | 10/2008 |
| WO | WO-2009079211 | A1 | 6/2009 |
| WO | WO-2009149181 | A2 | 12/2009 |
| WO | WO-2011112976 | A2 | 9/2011 |
| WO | WO-2012121986 | A2 | 9/2012 |
| WO | WO-2013093921 | A1 | 6/2013 |
| WO | WO-2013123147 | A1 | 8/2013 |
| WO | WO-2013172788 | A1 | 11/2013 |
| WO | WO-2015138970 | A1 | 9/2015 |
| WO | WO-2016042211 | A1 | 3/2016 |
| WO | WO-2016156992 | A2 | 10/2016 |
| WO | WO-2017053757 | A1 | 3/2017 |
| WO | WO-2017165889 | A2 | 9/2017 |
| WO | WO-2018092098 | A1 | 5/2018 |
| WO | WO-2018119493 | A1 | 7/2018 |
| WO | WO-2018212792 | A2 | 11/2018 |
| WO | WO-2019084209 | A1 | 5/2019 |

(56) References Cited

FOREIGN PATENT DOCUMENTS

WO WO-2020125910 A1 6/2020
WO WO-2020160491 A1 8/2020
WO WO-2021155216 A1 8/2021

OTHER PUBLICATIONS

"U.S. Appl. No. 17/162,568, Response filed Apr. 12, 2024 to Restriction Requirement mailed Mar. 8, 2024", 5 pgs.
"U.S. Appl. No. 17/162,568, Response filed Dec. 5, 2024 to Non Final Office Action mailed Sep. 9, 2024", 7 pgs.
"U.S. Appl. No. 17/162,568, Restriction Requirement mailed Mar. 8, 2024", 8 pgs.
"U.S. Appl. No. 18/807,587, Preliminary Amendment filed Aug. 19, 2024", 6 pgs.
"U.S. Appl. No. 19/023,137, Preliminary Amendment filed Jan. 24, 2025", 6 pgs.
"Canadian Application Serial No. 3,169,222, Examiners Rule 86(2) Report mailed Aug. 5, 2024", 3 pgs.
"Canadian Application Serial No. 3,169,222, Response filed Dec. 4, 2024 to Examiners Rule 86(2) Report mailed Aug. 5, 2024", 8 pgs.
"European Application Serial No. 21748188.6, Response filed Aug. 16, 2024 to Extended European Search Report mailed Feb. 2, 2024", 12 pgs.
"European Application Serial No. 24156664.5, Extended European Search Report mailed Jun. 10, 2024", 8 pgs.
"European Application Serial No. 24156664.5, Response filed Jan. 23, 2025 to Extended European Search Report mailed Jun. 10, 2024", 10 pgs.
"Japanese Application Serial No. 2022-545800, Final Notification of Reasons for Refusal mailed Feb. 8, 202024", W/ English translation, 7 pgs.
"Japanese Application Serial No. 2022-545800, Response filed Mar. 11, 2024 to Final Notification of Reasons for Refusal mailed Feb. 8, 2024", w/ current English claims, 7 pgs.
"Chinese Application Serial No. 202180016725.8, Office Action mailed Feb. 15, 2023", W English Translation, 23 pgs.
"International Application Serial No. PCT US2018 000119, International Search Report mailed Dec. 11, 2018", 3 pgs.
"International Application Serial No. PCT US2018 000119, Written Opinion mailed Dec. 11, 2018", 6 pgs.
"U.S. Appl. No. 17/162,568, Preliminary Amendment filed Nov. 22, 2022", 3 pgs.
"Synthasome X-Repair Technology", FAQs, [Online] Retrieved from the internet:http: www.synthasome.comxRepair-technology.php, (Mar. 22, 2017), 1 pg.
"Achilles Tendon Information", WRIGHT brochure, [Online] Retrieved from the internet:http: www.wright.com healthcare-professionals graftjacket applications achilles-tendon accessed Nov. 12, 2017, 2 pgs.
"International Application Serial No. PCT US2021 015801, International Search Report mailed May 5, 2021", 2 pgs.
"International Application Serial No. PCT US2021 015801, Written Opinion mailed May 5, 2021", 6 pgs.
"International Application Serial No. PCT US2021 015801, International Preliminary Report on Patentability mailed Aug. 11, 2022", 8 pgs.
"International Application Serial No. PCT US2020 016244, Invitation to Pay Additional Fees mailed Apr. 23, 2020", 2 pgs.
"International Application Serial No. PCT US2020 016244, International Search Report mailed Jun. 22, 2020", 4 pgs.
"International Application Serial No. PCT US2020 016244, Written Opinion mailed Jun. 22, 2020", 6 pgs.
"K80 HS80 Series Braider Manual for Steeger", USA, (2018), 61 pgs.
Addad, "Isolation, Characterization and Biological Evaluation of Jellyfish Collagen for Use in Biomedical Applications", Marine Drugs, vol. 9, (Jun. 7, 2011), 967-983.
Ahmad, Z., "Effect of 1-ethyl-3-(3-dimethylaminopropyl) carbodiimide and N-hydroxysuccinimide concentrations on the mechanical and biological characteristics of cross-linked collagen fibres for tendon repair", Regenerative Biomaterials, vol. 2, No. 2, (May 16, 2015), 77-85.
Benjamin, M., "The structure of tendons and ligaments, Regenerative Medicine and Biomaterials for the Repair of Connective Tissues", Woodhead, (2010).
Benjamin, M., "Structure-function relationships in tendons: A review", Journal of Anatomy, 212, (2008), 18 pgs.
Bishop, "Design of an Extrusion System to Optimize the Production of Self-Assembled Collagen Microthreads", Degree of Bachelor of Science Paper, Worcester Polytechnic Institute, Project No. GXP-0508, 124 pgs.
Bokor, D. J, "Preliminary investigation of a biological augmentation of rotator cuff repairs using a collagen implant: A 2-year MRI follow-up", Muscles, Ligaments and Tendons Journal, 5(3), (2015), 144-150.
Brown, B, "Macrophage phenotype and remodeling outcomes in response to biologic scaffolds with and without a cellular component", Biomaterials, 30(8), (2009), 24 pgs.
Brown, B. N, "Macrophage phenotype as a predictor of constructive remodeling following the implantation of biologically derived surgical mesh materials", Acta Biomaterialia, 8(3), (2012), 23 pgs.
Brown, B. N, "Expanded applications, shifting paradigms and an improved understanding of host-biomaterial interactions", Acta Biomaterialia. Acta Materialia Inc., 9(2), (2013), 8 pgs.
Caruso, A. B, "Functional evaluation of collagen fiber scaffolds for ACL reconstruction: Cyclic loading in proteolytic enzyme solutions", Journal of Biomedical Materials Research- Part A, 69(1), Apr. 2004., (Apr. 2004), 9 pgs.
Caves, J., "Fibrillogenesis in Continuously Spun Synthetic Collagen Fiber", J Biomed Mater Res B. Appl Biomater, 93(1), Apr. 2010., (Apr. 2010), 31 pgs.
Chattopadhyay, S., "Review collagen-based biomaterials for wound healing", Biopolymers, 101(8): 821-833, Aug. 2014., (2014), 24 pgs.
Chen, J., "Scaffolds for tendon and ligament repair: Review of the efficacy of commercial products", Expert Review of Medical Devices, 6(1), (2009), 61-73.
Cheng, "Isolation, Characterization and Evaluation of Collagen from Jellyfish *Rhopilema esculentum* Kishinouye for Use in Hemostatic Applications", PLoS One 12(1), 1-21., (Jan. 19, 2017), 1-21.
Chu, C. C, "Materials for absorbable and nonabsorbable surgical sutures", in Biotextiles As Medical Implants, (2013), 3 pgs.
Cornwell, K. G, "Characterizing fibroblast migration on discrete collagen threads for applications in tissue regeneration", Journal of Biomedical Materials Research—Part A, Aug. 2004. 55-62., https: www.researchgate.net publication 8346982, (Aug. 2004), 9 pgs.
Cornwell, K. G, "Crosslin king of discrete self-assembled collagen threads: Effects on mechanical strength and cell-matrix interactions", Journal of Biomedical Materials Research Part A,80(2):362-71 Feb. 2007., (Feb. 2007), 10 pgs.
Cui, "Investigation of Drug Release and Matrix Degradation of Electrospun Poly(DL-lactide) Fibers with Paracetanol inoculation", Biomacromolecules, Jul. 2006, 1623-1629., (Mar. 2006), 7 pgs.
Delgado, L. M, "To Cross-Link or Not to Cross-Link? Cross-Linking Associated Foreign Body Response of Collagen-Based Devices", Tissue Engineering Part B: Reviews, 21(3), (2015), 298-313.
Delguerra, "Optimization if the interaction between ethylene-vinyl alcohol copolymers and human endothelial cells", Journal of Materials Science: Materials in Medicine 7, (1996), 5 pgs.
Demirbilek, "Oxidative Stress Parameters of L929 Cells Cultured on Plasma-Modified PDLLA Scaffolds", Appl. Biochem Biotechnol, 164:780-792; Abstract Only, 14 pgs., (Feb. 2011), 14 pgs.
Dong, "Electrospinning of Collagen Nanofiber Scaffolds from Benign Solvents", Macromol. Rapid Commun. 2009, 30, 539-542., (2009), 4 pgs.
Dunn, M. G, "Optimization of extruded collagen fibers for ACL reconstruction", Journal of Biomedical Materials Research, 27(12), (1993), 11 pgs.

(56) References Cited

OTHER PUBLICATIONS

Elder, S., "Suitability of EGCG as a Means of Stabilizing a Porcine Osteochondral Xenograft", Journal of functional biomaterials, 8(43), (2017), 14 pgs.
Enea, D., "Extruded collagen fibres for tissue engineering applications: Effect of crosslinking method on mechanical and biological properties", Journal of Materials Science: Materials in Medicine, 22(6), [Online]. Retrieved from the Internet:URL: https: link.springer.com content pdf 10.1007 s10856-011-4336-1.pdf?pdf=button, (Jun. 1, 2011), 1569-1578.
Enea, D., "Collagen fibre implant for tendon and ligament biological augmentation. In vivo study in an ovine model", Knee Surgery, Sports Traumatology, Arthroscopy, vol. 21, No. 8, [Online]. Retrieved from the Internet: URL: https: link.springer.com content pdf 10.1007 s00167-012-2102-7.pdf?pdf=button, (Aug. 1, 2013), 1783-1793.
Fathima, N. N, "Interaction of aldehydes with collagen: Effect on thermal, enzymatic and conformational stability", International Journal of Biological Macromolecules 34 (2004) 241-247., (May 2004), 7 pgs.
Frederick, C Eichmiller, "Mechanical Properties of Ultra High Molecular Weight Polyethylene NIST Reference Material # 8456", [Online]. Retrieved from the Internet: URL: https: www.nist.gov publications mechanical-properties-ultra-high-molecular-weight-polyethylene-nisi-reference-material, (Apr. 1, 2001), 1 pg.
Gabler, "In Vivo Evaluation of Different Collagen Scaffolds in an Achilles Tendon Defect Model", BioMed Research International, vol. 2018, Article ID 6432742, (2018), 1-11.
Gallagher, A. J, "Dynamic tensile properties of human skin", RCOBI Conference Proceedings—International Research Council on theBiomechanics of Injury, (2012), 494-502.
Garlotta, Donald, "A Literature Review of Poly(Lactic Acid)", Journal of Polymers and the Environment, vol. 9, No. 2, Apr. 2001., (2001), 22 pgs.
Gentleman, Eileen, "Mechanical characterization of collagen fibers and scaffolds for tissue engineering", Biomaterials, Elsevier, Amsterdam, NL, vol. 24, No. 21, accepted Mar. 24, 2003, (Sep. 1, 2003), 3805-3813.
Gigante, A., "Collagen I membranes for tendon repair: Effect of collagen fiber orientation on cell behavior", Journal of Orthopaedic Research, 27, (2009), 826-832.
Gillette, "In situ collagen assembly for integrating microfabricated three-dimensional cell-seeded matrices", Nature Materials vol. 7 Aug. 2008, 5 pgs., (May 30, 2008), 5 pgs.
Gordon, S., "Monocyte and macrophage heterogeneity", Nature Reviews Immunology, vol. 5, Dec. 2005, 12 pgs., (Dec. 2005), 12 pgs.
Gough, J. E, "Cytotoxicity of glutaraldehyde crosslinked collagen poly(vinyl alcohol) films is by the mechanism of apoptosis", Journal of Biomedical Materials Research, 61(1), (2002), 10 pgs.
Peters, A. E, "Tissue material properties and computational modelling of the human tibiofemoral joint: a critical review", PeerJ, 6, (2018).
Haider, "A comprehensive review summarizing the effect of electrospinning parameters and potential applications of nanofibers in biomedical and biotechnology", Arabian Journal of Chemistry, (2015), 1-24.
Haugh, M. G, "The effect of dehydrothermal treatment on the mechanical and structural properties of collagen-GAG scaffolds", Journal of Biomedical Materials Research—Part A, 89(2), (2009), 22 pgs.
Haynl, Christian, "Microfluidics-produced collagen fibers show extraordinary mechanical properties", Nanoletters, 16 (9), 2016, 5917-5922., (Aug. 2016), 8 pgs.
Hochleitner, "Melt electrowriting below the critical translation speed to fabricate crimped elastomer scaffolds with non-linear extension behaviour mimicking that of ligaments and tendons", Acta Blomaterialia, 72, (2018), 110-120.
Hochleitner, "Melt Electrowriting of Thermoplastic Elastomers", Macromolecular Rapid Communications, 39, 1800055, (2018), 7 pgs.
Hogan, M. V, "Tissue engineering of ligaments for reconstructive surgery", Arthroscopy—Journal of Arthroscopic and Related Surgery. Arthroscopy Association of North America, 31 {5), (2015), 9 pgs.
Hoque, "Extrusion Based Rapid Prototyping Technique: An Advanced Platform for Tissue Engineering Scaffold Fabrication", Biopolymers 97: 83-93, 2012, (Aug. 9, 2011), 11 pgs.
Hrynevich, "Dimension-Based Design of Melt Electrowritten Scaffolds", Nano-Micro Small, 14, 1800232, 2018. 6pgs., (2018), 6 pgs.
Huang, "A review on polymer nanofibers by electrospinning and their applications in nanocomposites", Composites Science and Technology 63, (2003), 2223-2253.
Hwang, "Effects of Zero-Length and Non-Zero-Length Cross-Linking Reagents on the Optical Spectral Properties and Structures of Collagen Hydrogels", ACS Appl. Mater. Interfaces. 4, (2012), 7 pgs.
Jamshidi, "Thermal characterization of polylactides", Polymer, vol. 29,, (1988), 6 pgs.
Jha, "Electrospun Collagen: A Tissue Engineering Scaffold with Unique Functional Properties in a Wide Variety of Applications", Journal of Nanomaterials, vol. 2011, Article ID 348268, (2011), 1-15.
Kato, Y. P, "Mechanical properties of collagen fibres: a comparison of reconstituted and rat tail tendon fibres", Biomaterials, Elsevier, Amsterdam, NL, vol. 10, No. 1,, (Jan. 1, 1989), 38-42.
Katsogiannis, "Porous electrospun polycarprolactone (PCL) fibres by phase separation", European Polymer Journal, 69, (2015), 284-295.
Kew, "Synthetic collagen fascicles for the regeneration of tendon tissue", [Online] Retrieved from the internet:www.elsevier.com locate actabiomat, (2012), 15 pgs.
Kiapour, A. M, "Validation of Porcine Knee as a Sex-specific Model to Study Human Anterior Cruciate Ligament Disorders", Clinical Orthopaedics and Related Research, 473(2), (2015), 639-650.
Koob, T. J, "Biocompatibility of NGDA-polymerized collagen fibers. II. Attachment, proliferation, and migration of tendon fibroblasts in vitro", Journal of Biomedical Materials Research, 56, (2001), 9 pgs.
Koster, Sarah, "An in-situ Study of Collagen Self-Assembly Processes", Biomacromolecules. Jan. 2008 ; 9(1):199-207., (Jan. 2008), 19 pgs.
Krishnamoorthi, "Isolation and partial characterization of collagen from outer skin of Sepia pharaonis (Ehrenberg, 1831) from Puducherry coast", Biochemistry and Biophysics Reports 10, (2017), 39-45.
Kudur, M. H, "Sutures and suturing techniques in skin closure", Indian Journal of Dermatology, Venereology and Leprology, 75{4), (2009), 425-434.
Lam, Kevin H, "A high-throughput microfluidic method for fabricating aligned collagen fibrills to study Keratocyte behavior", Biomed Microdevices. ; 21(4): 99, [Online]. Retrieved from the Internet:URL: https: doi.org 10.007s10544-019-0436-3, (2019), 22 pgs.
Lanfer, Babette, "The growth and differentiation of mesenchymal stem and progenitor cells cultured on aligned collagen matrices", Biomaterials 30, 2009, 5950-5958., [Online]. Retrieved from the Internet: URL: www.elsevier.com locate biomaterials, (2009), 9 pgs.
Lee, C. H, "Biomedical applications of collagen", International Journal of Pharmaceutics, 221, (2001), 22 pgs.
Lee, P., "Microfluidic alignment of collagen fibers for in vitro cell culture", Biomed Microdevices, 8: 35-41., (2006), 7 pgs.
Leiter, R. S. J, "Long-term follow-up of ACL reconstruction with hamstring autograft", Knee Surgery, Sports Traumatology, Arthroscopy, 22(5), (2014), 10 pgs.
Li, "Recent advances in stereocomplexation of enantiomeric PLA-based copolymers and applications", Progress in Polymer Science, 62, Abstract Only, (2016), 1 pg.
Li, "3D-Printed Biopolymers for Tissue Engineering Application", International Journal of Polymer Science vol. 2014, Article ID 829145, (2014), 1-13.

(56) References Cited

OTHER PUBLICATIONS

Liao, "In Vitro and in Vivo Degradation of Mineralized Collagen-Based Composite Scaffold: Nanohydroxyapatite Collagen Poly(L-lactide)", Tissue Engineering Part A, vol. 10, Issue 1-2, (2004), 8 pgs.
Lin, "Functionalized Poly(D,L-lactide) for Pulmonary Epithelial Cell Culture", Advanced Engineering Materials, (Mar. 8, 2010), 2 pgs.
Liu, "Novel 3D collagen scaffolds fabricated by indirect printing technique for tissue engineering", Abstract, J. Biomedical Materials Research Part B: Applied Biomaterials, Issue 2, (2008), 3 pgs.
Liu, S. H, "Collagen in tendon, ligament, and bone healing: A current review", Clinical Orthopaedics and Related Research, (318), (1995), 265-278.
Lu, "Techniques for fabrication and construction of three-dimensional scaffolds for tissue engineering", International Journal of Nanomedicine, vol. 8, (Jan. 17, 2013), 337-350.
Lubasova, Daniela, "Controlled Morphology of Porous Polyvinyl Butyral Nanofibers", Hindawi Publishing Corporation Journal of Nanomaterials, vol. 2011, Article ID 292516, 6 pgs.
Ma, "Scaffolds for tissue fabrication", Materialstoday, (May 2004), 30-40.
Maghdouri-White, Y., "Biomanufacturing and Translational Research of an Aligned Collagen-Based Electrospun Tissue Engineered Device (TEND) for Tendon Regeneration", Biomed. Mater. 16 (2021) 025025, (2019), 22 pgs.
Matava, "Partial-Thickness Rotator Cuff Tears", The American Journal of Sports Medicine, vol. 33, No. 9, [Online]. Retrieved from the Internet: URL: https: www.wosm.com wp-content uploads 2014 11 Partial_Thickness-rotator-cuff-tears.Pdf., (2005), 13 pgs.
Matsusue, Y., "Tissue reaction of bioabsorbable ultra high strength poly (L-lactide) rod: A long-term study in rabbits", Clinical Orthopaedics and Related Research, 317, (1995), 246-253.
Mccarty, "Layer-by-layer Collagen Deposition in Microfluidic Devices for Microtissue Stabilization", Journal of Visualized Experiments Sep. 2015, 103, e53078, (Sep. 29, 2016), 9 pgs.
Meena, C., "Biomedical and industrial applications of collagen", Proceedings of the Indian Academy of Sciences: Chemical Sciences, 111(2), (1999), 319-329.
Meyer, M., "Processing of collagen based biomaterials and the resulting materials properties", BioMedical Engineering Online. BioMed Central, 18(1), (2019), 1-74.
Middleton, "Synthetic biodegradable polymers as orthopedic devices", Biomaterials 21, (2000), 2335-2346.
Mills, C. D, "M-1 M-2 Macrophages and the Th1 Th2 Paradigm", The Journal of Immunology, 164(12), (2000), 6166-6173.
Mosser, D. M, "The many faces of macrophage activation", Journal of Leukocyte Biology, 73(2), (2003), 209-212.
Noyes, F., "The strength of the anterior cruciate ligament in humans and *Rhesus* monkeys", The Journal of Bone and Joint Surgery, 58{8), (1976), 9 pgs.
Oryan, "Chemical crosslinking of biopolymeric scaffolds: Current knowledge and future directions of crosslinked engineered bone scaffolds", International Journal of Biological Macromolecules, 107, (2018), 11 pgs.
Paul, R. G, "Chemical stabilisation of collagen as a biomimetic", TheScientificWorldJOURNAL 3, (2003), 138-155.
Perrone, G. S, "Bench-to-bedside: Bridge-enhanced anterior cruciate ligament repair", Journal of Orthopaedic Research, (2017).
Porcheray, F., "Macrophage activation switching: An asset for the resolution of inflammation", Clinical and Experimental Immunology, 142, (2005), 481-489.
Price, J., "4 Figures: Liquid Crystalline Ordered Collagen Substrates for Applications in Tissue Engineering", ACS Biomaterials Science and Engineering, [Online] Retrieved from the internet:https: www.researchgate.net publication 297595398, (Mar. 2016), 18 pgs.
Punnoose, "Electrospun Type 1 Collagen matrices using a novel benign solvent for Cardiac tissue engineering", Artificial Cells, Nanomedicine, and Biotechnology, 44:5, 1318-1325, (May 2015), 9 pgs.
"Australian Application Serial No. 2021213237, First Examination Report mailed Jun. 29, 2023", 5 pgs.
"Australian Application Serial No. 2021213237, Response filed Sep. 1, 2023 to First Examination Report mailed Jun. 29, 2023", 19 pgs.
"Australian Application Serial No. 2021213237, Response filed Dec. 1, 2023 to Subsequent Examiners Report mailed Sep. 7, 2023", 14 pgs.
"Australian Application Serial No. 2021213237, Subsequent Examiners Report mailed Sep. 7, 2023", 4 pgs.
"Canadian Application Serial No. 3,169,222, Examiners Rule 86(2) Requisition mailed Sep. 14, 2023", 5 pgs.
"Canadian Application Serial No. 3,169,222, Response filed Jan. 12, 2024 to Examiners Rule 86(2) Report mailed Sep. 14, 2023", 21 pgs.
"European Application Serial No. 21748188.6, Extended European Search Report mailed Feb. 2, 2024", 8 pgs.
"Japanese Application Serial No. 2022-545800, Notification of Reasons for Rejection mailed Aug. 31, 2023", W/ English Translation, 7 pgs.
"Japanese Application Serial No. 2022-545800, Response Filed Nov. 21, 2023 to Notification of Reasons for Rejection mailed Aug. 31, 2023", W/ English Claims, 11 pgs.
"Japanese Application Serial No. 2022-545800, Written Amendment filed Nov. 21, 2022", w/English Translation, 5 pgs.
Qiao, "Compositional and in Vitro Evaluation of Nonwoven Type I Collagen Poly-dl-lactic Acid Scaffolds for Bone", Journal of Functional Biomaterials, vol. 6, (2015), 667-686.
Rangaraj, Aravindan, "Role of collagen in wound management", Wounds UK, 7(2), (2011), 54-63.
Ratcliffe, A, "Scaffolds for Tendon and Ligament Repair and Regeneration", Ann Biomed Eng. Mar. 2015, 43(3):819-831., (Mar. 2015), 27 pgs.
Ratner, B D, "The biocompatibility manifesto: Biocompatibility for the twenty-first century", J. of Cardiovasc. Trans. Res. (2011) 4:523-527, (2011), 5 pgs.
Reddy, N, "Crosslinking biopolymers for biomedical applications", Trends in Biotechnology, Elsevier Ltd, 33(6), (2015), 8 pgs.
Rudolph, "Surface Modification of Biodegradable Polymers towards Better Biocompatibility and Lower Thrombogenicity", PLOS One, (Dec. 7, 2015), 1-17.
Saeidi, Nima, "Production of highly aligned collagen lamellae by combining shear force and thin film confinement", Acta Biomater. Jun. 2011 ; 7(6): 2437-2447., [Online]. Retrieved from the Internet: URL: www.elsevier.com locate actabiomat, (Jun. 2011), 22 pgs.
Salgado, "Bone Tissue Engineering: State of the Art and Future Trends", Abstract, Macromolecular, Bioscience, 2004, vol. 4, Issue 8, (2004), 4 pgs.
Sanchez-Ruiz, J. M, "Differential scanning calorimetry of proteins", in Proteins: Structure, Function, and Engineering, Subcellular Biochemistry, Abstract Only, (1995), 11 pgs.
Schlegel, T. F, "Radiologic and clinical evaluation of a bioabsorbable collagen implant to treat partial-thickness tears: a prospective multicenter study", Journal of Shoulder and Elbow Surgery, 27(2), 2017., (2017), 10 pgs.
Sensini, Alberto, "Biofabrication of bundles of poly(lactic acid)-collagen blends mimicking the fascicles of the human Achille tendon", Biofabrication V9 N1, [Online]. Retrieved from the Internet:http: doi.org 10.1088 1758-5090 aa6204, (Mar. 8, 2017), 1-28.
Seon, J. K, "Osteoarthritis after anterior cruciate ligament reconstruction using a patellar tendon autograft", International Orthopaedics, 30(2), (2006), 94-98.
Shaerf, D. A, "Anterior cruciate ligament reconstruction best practice: A review of graft choice", World Journal of Orthopedics, 5(1), (2014), 9 pgs.
Shepherd, D V, "The process of EDC-NHS cross-linking of reconstituted collagen fibres increases collagen fibrillar order and alignment", APL Materials, 3(1), (2015), 1-13.
Sherman, O. H, "Anterior cruciate ligament reconstruction: Which graft is best?", Arthroscopy—Journal of Arthroscopic and Related Surgery, 20(9), (2004), 7 pgs.

(56) References Cited

OTHER PUBLICATIONS

Showery, J. E, "The Rising Incidence of Degenerative and Post-traumatic Osteoarthritis of the Knee in the United States Military", Journal of Arthroplasty, 31 (10), (2016), 2108-2114.
Slow, "Plasma Methods for the Generation of Chemically Reactive Surfaces for Biomolecule Immobilization and Cell Colonization—A Review", Plasma Processes and Polymers, vol. 3, (Jun. 2006), 392-418.
Smith, T. O, "Is reconstruction the best management strategy for anterior cruciate ligament rupture? A systematic review and meta-analysis comparing anterior cruciate ligament reconstruction versus non-operative treatment", Knee, 21(2), (2014), 2 pgs.
Spanneberg, Robert, "Glyoxal modification of gelatin leads to change in properties of solutions and resulting films", (2011), 8 pgs.
Stout, R. D, "Macrophages Sequentially Change Their Functional Phenotype in Response to Changes in Microenvironmental Influences", The Journal of Immunology, 175, (2005), 9 pgs.
Taylor, "Six Bioabsorbable Polymers: In Vitro Acute Toxicity of Accumulated Degradation Products", Journal of applied biomaterials, 5(2), (1994), 151-157.
Tham, "Surface Modification of Poly (lactic acid) (PLA) via Alkaline Hydrolysis Degradation", Advanced Materials Research, vol. 970, Abstract Only, (2014), 324-327.
Tsugawa, A. J, "Suture materials and biomaterials", in Oral and Maxillofacial Surgery in Dogs and Cats, (2012), 3 pgs.
Tsuji, H, "Poly(lactide) Stereocomplexes: Formation, Structure, Properties, Degradation, and Applications", Macroomol. Biosci., 5, (2005), 569-597.
Tutak, "The support of bone marrow stromal cell differentiation by airbrushed nanofibers scaffolds", Abstract, Biomaterials, 2013, vol. 34, Issue 10, (2013), 3 pgs.
Umashankar, P. Kumari, "Glutaraldehyde treatment elicits toxic response compared to decellularization in bovine pericardium", Toxicology International, 19, (2012), 51-58.
Van Kampen, C., "Tissue-engineered augmentation of a rotator cuff tendon using a reconstituted collagen scaffold: A histological evaluation in sheep", Muscles, Ligaments and Tendons Journal, 3, (2013), 229-235.
Vavken, P, "Biomechanical outcomes after bioenhanced anterior cruciateligament repair and anterior cruciate ligament reconstruction are equal in a porcine model", Arthroscopy—Journal of Arthrosoopic and Related Surgery, 28(5), (2012), 15 pgs.
Vijayaraghavan, R, "Biocompatibility of choline salts as crosslinking agents for collagen based biomaterials", Chemical Communications, 46(2), (2010), 4 pgs.
Vunjak-Novakovic, G, "Tissue Engineering of Ligaments", Annual Review of Biomedical Engineering. Annual Reviews, 6(1), (2004), 31 pgs.
Wang, H., "Acceleration of wound healing in acute full-thickness skin wounds using a collagen-binding peptide with an affinity for MSCs", Burns and Trauma, 2(4), (2014), 6 pgs.
Wang, J H.-C, "Tendon Biomechanics and Mechanobiology—a mini-review of basic concepts", Journal of Hand Therapy, 25(2), (2012), 14 pgs.
Wang, L, "Glyoxal crosslinking of cell-seeded chitosan collagen hydrogels for bone regeneration", Acta Blomaterialia, 7(6), (2011), 16 pgs.
Wang, Ming-Che, "Collagen fibres with improved strength for the repair of soft tissue injuries", Biomaterials, Elsevier, Amsterdam, NL, vol. 15, No. 7, (Jun. 1, 1994), 507-512.
Watts, G, "Sutures for Skin Closure", The Lancet, 305(7906), (1975), 1 pg.
Wiegand, N, "The Role of Differential Scanning Calorimetry in the Diagnostics of Musculoskeletal Diseases", EC Orthopaedics, 4, (2017), 14 pgs.
Winkler, "microfabricated, optically accessible device to study the effects of mechanical cues on collagen fiber organization", Biomed Microdevices, 16, (2014), 25 pgs.
Woo, S. L. Y, "Tissue engineering of ligament and tendon healing", in Clinical Orthopaedics and Related Research, (1999), 12 pgs.
Wortmann, "New Polymers for Needleless Electrospinning from Low-Toxic Solvents", Nanomaterials, 9, 52, (2019), 1-11.
Wren, T. A. L, "Mechanical properties of the human achilles tendon", Clinical Biomechanics, 16, (2001), 8 pgs.
Yaari, Amit, "Wet Spinning and Drawing of Human Recombinant Collagen", ACS Biomaterials Sci. Eng. Feb. 3, 2016, 349-360., (Feb. 15, 2016), 6 pgs.
Yang, G, "Tendon and ligament regeneration and repair: Clinical relevance and developmental paradigm", Birth Defects Research Part C—Embryo Today: Reviews, vol. 99(3), (2013), 35 pgs.
Yannas, I., "Cross-Linking of Gelatine by Dehydration", Nature, 215, (1967), 509-510.
Zagho, "Recent Trends in Electrospinning of Polymer Nanofibers and their Applications as Templates for Metal Oxide Nanofibers Preparation", INTECH open science, open minds, (2016), 4-24.
Zeugolis, "Cross-linking of extruded collagen fibers", Wiley InterScience, [Online] Retrieved from the internet:www.interscience.wiley.com, (2008), 14 pgs.
Zhang, "Electrospun scaffolds from silk fibroin and their cellular compatibility", Journal of Biomedical Materials Research Part A, (2009), 8 pgs.
Zhong, "Isolation and Characterization of Collagen from the Body Wall of Sea Cucumber *Stichopus monotuberculatus*", Journal of Food Science, vol. 80, No. 4, (2015), 9 pgs.
Zobitz, "Determination of the Compressive Material Properties of the Supraspinatus Tendon", Journal of Biomechanical Engineering, vol. 123, (2001), 5 pgs.
"U.S. Appl. No. 17/162,568, Advisory Action mailed May 6, 2025", 3 pgs.
"U.S. Appl. No. 17/162,568, Final Office Action mailed Mar. 3, 2025", 14 pgs.
"U.S. Appl. No. 17/162,568, Response filed Mar. 27, 2025 to Final Office Action mailed Mar. 3, 2025", 7 pgs.
"U.S. Appl. No. 18/807,587, Supplemental Preliminary Amendment filed Feb. 13, 2025", 5 pgs.
"U.S. Appl. No. 19/023,137, Supplemental Preliminary Amendment filed Feb. 6, 2025", 6 pgs.
"Australian Application Serial No. 2024200575, First Examination Report mailed May 9, 2025", 3 pgs.
"Canadian Application Serial No. 3,228,811, Examiners Rule 86(2) Report mailed Jun. 19, 2025", 6 pgs.
"Australian Application Serial No. 2024200575, Response Filed Nov. 24, 2025 to Subsequent Examination Report mailed Aug. 22, 2025", 15 pgs.
"Australian Application Serial No. 2024200575, Subsequent Examination Report mailed Dec. 22, 2025", 3 pgs.
"Canadian Application Serial No. 3,228,811, Response filed Oct. 17, 2025 to Examiners Rule 86(2) Report mailed Jun. 19, 2025", W/ English Claims, 16 pgs.
"Australian Application Serial No. 2024200575, Response filed Feb. 16, 2026 to Subsequent Examination Report mailed Dec. 22, 2025", W/ English Claims, 16 pgs.
"Australian Application Serial No. 2024200575, Subsequent Examination Report mailed Mar. 18, 2026", 3 pgs.
"European Application Serial No. 21748188.6, Response filed Nov. 28, 2025 to Communication Pursuant to Article 94(3) EPC mailed Sep. 1, 2025", 3 pgs.
U.S. Appl. No. 18/807,587, filed Aug. 16, 2024, Braided Surgical Implants.
U.S. Appl. No. 19/023,137, filed Jan. 15, 2025, Braided Surgical Implants.

* cited by examiner

| Mechanical Property | | High Strength Collagen Fiber | UHMWPE Fiber |
|---|---|---|---|
| Ultimate Tensile Strength (MPA) | Min | 50 | 3000 |
| | Max | 500 | 5000 |

FIG. 16

| | SIZE (CONSTRUCT) | | | |
|---|---|---|---|---|
| **Property** | **2-0 (Round)** | **#2 (Round)** | **1.5mm (Suture Tape)** | **2.5mm (Suture Tape)** |
| Straight Tensile Strength (N) (Observed) | 123-142 | 251-278 | 275-312 | 549-653 |
| Target range | 100-200 | 200-400 | 200-450 | 350-900 |
| Knot Tensile Strength (N) (Observed) | 44-68 | 103-148 | 125-177 | N/A |
| Target range | 26-100 | 85-200 | 100-250 | N/A |
| Abraded Tensile Strength (N) (Observed) | 106-146 | 264-270 | 260 - 282 | 474-609 |
| Target range | 30-200 | 150-350 | 150-350 | 200-750 |
| Fluid Absorption (fold) (Observed) | 2X-3.4X | 2X-3.3X | 2X-3.7X | 2X-3.7X |
| Target range | 0.75X-4.25X | 0.75X-4.1X | 0.75X-4.6X | 0.75X-4.6X |
| Knot Security (N) (Observed) | 32-86.5 | 52-159 | 52-182 | N/A |
| Target range | 24-150 | 39-250 | 39-250 | N/A |
| Knot Profile (mm) (Observed) | 0.6-1.0 | 1.2-1.6 | 1.6-1.8 | N/A |
| Target range | 0.45-1.25 | 0.9-2.0 | 1.2-2.25 | N/A |
| Abrasiveness to Tissue (mm) (Observed) | 4.6-6.0 | 5.3-6.0 | 5.2-7.5 | 5.4-7.0 |
| Target range | 3.5-7.5 | 4.0-9.4 | 4.0-9.4 | 4.1-8.75 |
| Diameter (mm) (Observed) | 0.29-0.35 | 0.53-0.61 | 0.51-0.82 | 0.32-0.58 |

FIG. 31

| | SIZE (CONSTRUCT) | | | |
|---|---|---|---|---|
| **Property** | **2-0 (Round)** | **#2 (Round)** | **1.5mm (Suture Tape)** | **2.5mm (Suture Tape)** |
| Collagen % (Nominal) | 50% | 54% | 52% | 48% |
| Preferred range of Collagen % | 15-85% | 15-85% | 15-85% | 15-85% |
| UHMWPE % (Nominal) | 50% | 46% | 48% | 52% |
| Preferred range of UHMWPE % | 15-85% | 15-85% | 15-85% | 15-85% |

FIG. 32

Cellular Attachment Post Proliferation for 9 days

SUMMARY REPORT FOR DIAMETER 35 PPI

Anderson-Darling Normality Test

| | |
|---|---|
| A-Squared | 0.80 |
| P-Value | 0.034 |
| Mean | 0.33923 |
| StDev | 0.01823 |
| Variance | 0.00033 |
| Skewness | 0.18717 |
| Kurtosis | -1.30868 |
| N | 30 |
| Minimum | 0.30900 |
| 1st Quartile | 0.32500 |
| Median | 0.33650 |
| 3rd Quartile | 0.35550 |
| Maximum | 0.37000 |

99% Confidence Interval for Mean 0.33006 0.34841

99% Confidence Interval for Median 0.32500 0.35432

99% Confidence Interval for StDev 0.01357 0.02711

Summary Report for Knot Tensile_35PPI

Anderson-Darling Normality Test

| | |
|---|---|
| A-Squared | 0.21 |
| P-Value | 0.817 |
| Mean | 51.404 |
| StDev | 3.206 |
| Variance | 10.281 |
| Skewness | 0.153283 |
| Kurtosis | -0.987022 |
| N | 10 |
| Minimum | 47.110 |
| 1st Quartile | 48.622 |
| Median | 51.415 |
| 3rd Quartile | 54.248 |
| Maximum | 56.140 |
| **99% Confidence Interval for Mean** | |
| 48.109 | 54.699 |
| **99% Confidence Interval for Median** | |
| 47.153 | 55.898 |
| **99% Confidence Interval for StDev** | |
| 1.981 | 7.303 |

Tukey Pairwise Comparisons

Grouping Information Using the Tukey Method and 95% Confidence

| Factor | N | Mean | Grouping | |
|---|---|---|---|---|
| Visual size2R_21PPI_CCW | 30 | 16.37 | A | |
| Visual size2R_21PPI_Mixed W | 30 | 2.033 | | B |
| Visual size2R_31PPI_CCW | 30 | 0.400 | | B |
| Visual size2R_31PPI_Mixed W | 30 | 0.000000 | | B |

*Means that do not share a letter are significantly different.*

FIG. 47

BRAIDED SURGICAL IMPLANTS

CROSS-REFERENCE TO RELATED APPLICATIONS

This application is a continuation-in-part of U.S. patent application Ser. No. 17/162,568, filed Jan. 29, 2021, and entitled "BRAIDED SURGICAL IMPLANTS," which claims the benefit of Provisional Patent Application No. 62/968,873, filed on Jan. 31, 2020, and titled "Braided and Bundled Surgical Devices and Implants." The entire disclosure of each of the applications listed above is incorporated herein by reference.

STATEMENT OF U.S. GOVERNMENT SUPPORT

This invention was made with government support under SBIR contract 140D042000005 awarded by DARPA. The government has certain rights in the invention.

BACKGROUND

Surgical repair of injuries to various joints, ligaments and tendons is a common procedure, including those of the ankle, knee, shoulder, Achilles tendon, patellar tendon, and supraspinatus tendon, among others.

For example, in the United States, there are approximately 500,000 knee ligament ruptures annually, of which an estimated 100,000 are augmented with a scaffold implant or suture (typically a synthetic polymer, autograft or allograft).

Collagen tape repairs are intended to provide additional mechanical stabilization post-operatively and serve as a stimulus for healing and regeneration. However, despite their widespread use, currently marketed scaffolds do not share the same mechanical properties of human ligaments, nor have they been shown clinically to augment cellular/tissue healing in a meaningful way.

The current standard of care for a ruptured anterior cruciate ligament (ACL) is patient autografting, where tissue is harvested (for example, from hamstring or patellar tendon) for use in place of the ruptured or torn ACL. Autograft, as well as allograft tissues, are sometimes reinforced with a permanent synthetic suture—a procedure known as a ligament "internal brace." Allografting, where tissue is harvested from cadaveric human tendons, is also used in ACL reconstruction. ACL reconstruction with autografts or allografts entails drilling through and destroying the native ACL, eliminating its associated bone bed, nerve, and blood supply, thereby killing the native cell types present within and adjoining the ACL tissue. Allografts are supply-limited, promote scar formation, may provoke an immune response, and have poorly defined turnover rates, all of which can inhibit healing.

Such products must function in a variety of challenging biomechanical environments in which multiple functional parameters must be addressed. These parameters include, for example, compatibility with bodily tissue and fluids, strength, flexibility, and biodegradability.

There is a need in the art for a system and method that addresses the shortcomings of the prior art discussed above.

SUMMARY

In one aspect, an implantable biopolymer scaffold includes at least one braided strand, where the at least one braided strand consists essentially of high strength collagen fibers and high strength biocompatible fibers.

In another aspect, an implantable biopolymer scaffold includes a set of high strength collagen fibers braided with a set of high strength polyethylene fibers. A high strength collagen fiber of the set of high strength collagen fibers has a first ultimate tensile strength, and a high strength polyethylene fiber of the set of high strength polyethylene fibers has a second ultimate tensile strength. The first ultimate tensile strength is at least about 1 percent, 3 percent, 5 percent, or 10 percent of the second ultimate tensile strength.

In another aspect, a braided strand includes a set of high strength collagen fibers braided with a set of high strength polyethylene fibers. A high strength collagen fiber of the set of high strength collagen fibers has a first ultimate tensile strength, and a high strength polyethylene fiber of the set of high strength polyethylene fibers has a second ultimate tensile strength. The first ultimate tensile strength is at least about 1 percent, 3 percent, 5 percent, or 10 percent of the second ultimate tensile strength.

In yet other embodiments, the invention relates to methods of repairing an injured joint, ligament or tendon, involving the implanting of an implantable biopolymer scaffold according to the invention. In some procedures, the scaffold has a form factor of a brace. Related procedures include the securing of such an implant by suturing the implant into a desired position with a suture comprised of fibers according to the invention. Such methods may include fixation using various anchors as would be known to persons skilled in the art. Other procedures involve the closing of an incision or wound or repairing injured tissue utilizing such sutures. It is contemplated that such procedures and methods may be utilized for human and animal subjects.

In another aspect, an implantable biopolymer scaffold includes at least one braided strand comprising high strength collagen fibers and synthetic fibers, wherein the collagen fibers have a greater cross-sectional deformability than the synthetic fibers.

In another aspect, an implantable biopolymer scaffold includes a set of high strength collagen fibers braided with a set of high strength synthetic fibers. A high strength collagen fiber of the set of high strength collagen fibers has a first ultimate tensile strength, and a high strength synthetic fiber of the set of high strength synthetic fibers has a second ultimate tensile strength. In addition, the first ultimate tensile strength is at least one percent of the second ultimate tensile strength.

In another aspect, a braided strand includes a set of high strength collagen fibers braided with a set of high strength polyethylene fibers, wherein the collagen fibers have a greater cross-sectional deformability than the high strength polyethylene fibers.

In another aspect, an implantable biopolymer scaffold may include at least one braided strand, the braided strand consisting essentially of high strength collagen fibers and synthetic fibers, wherein the collagen fibers are configured to be replaced with native tissue with time following implantation.

In another aspect, a method of braiding a biopolymer scaffold. The method may include winding one or more synthetic fibers around a first high strength collagen fiber to form a first wound subassembly, and braiding the subassembly with two or more synthetic fibers.

Other systems, methods, features and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

FIG. 16 is a schematic view of a table listing tensile properties of ultra-high-molecular-weight polyethylene fibers and collagen fibers manufactured according to the embodiments;

FIG. 31 is a table showing properties of four different braided sutures constructed in accordance with the present disclosure;

FIG. 32 is a table showing the composition/ratios of collagen to UHMWPE of four exemplary braided sutures constructed in accordance with the present disclosure;

FIG. 47 is a table showing Tukey pairwise comparisons of #2 round sutures formed at various braiding settings;

DETAILED DESCRIPTION

Figure 1:
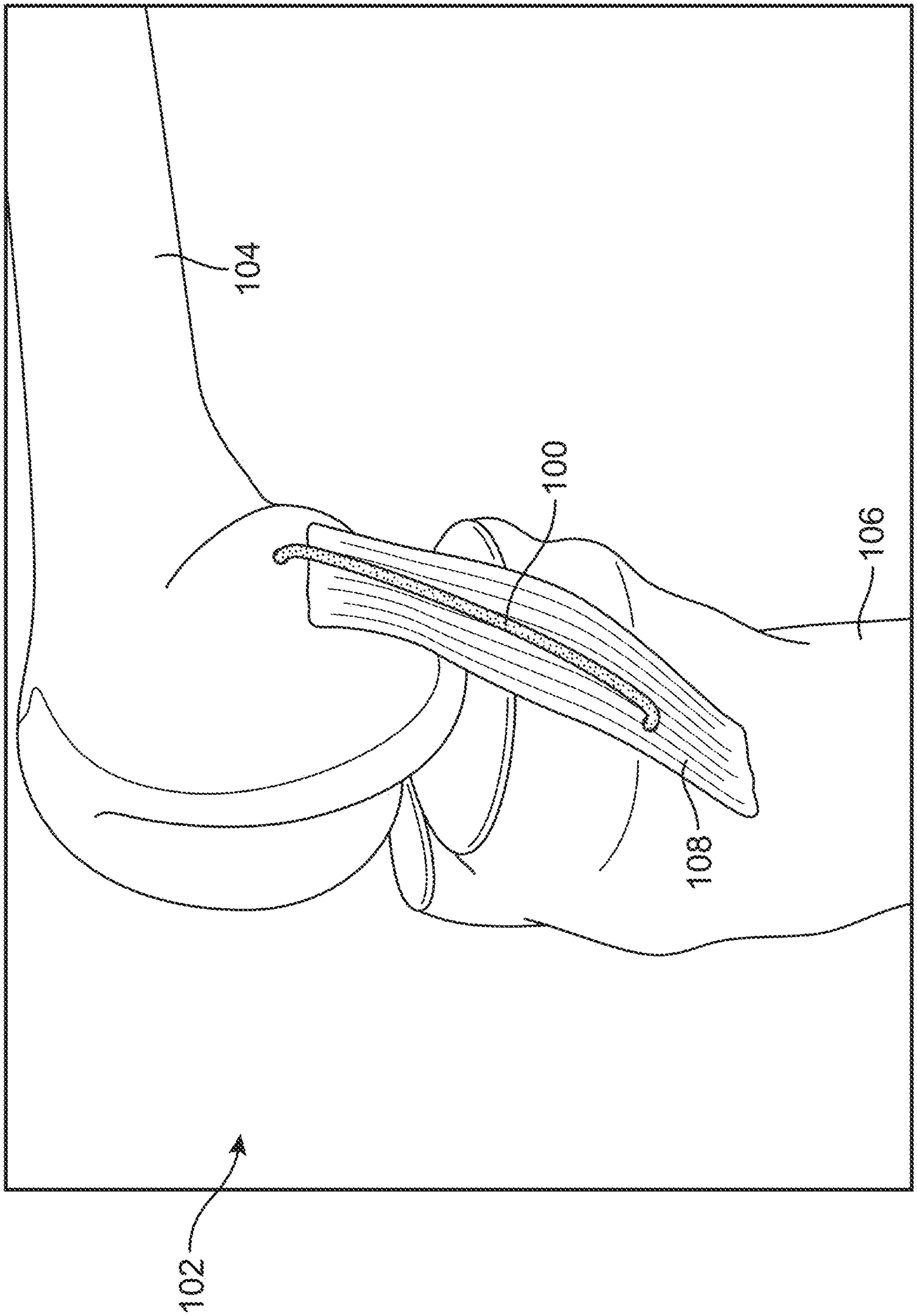
FIG. 1 is a schematic view of an anatomical region associated with a knee, in which an implantable biocompatible scaffold has been placed against a damaged ligament, according to an embodiment.

The present invention relates generally to novel form factors composed of high strength collagen fibers preferably combined with biocompatible fibers, preferably made of high strength biomaterials. Such biocompatible fibers may be those used in various biotextiles and medical textiles as are known in the art as well as synthetic and semi-synthetic polymers, carbon fibers and steel fibers. Contemplated biocompatible fibers include Polyhydroxy Butyrate (P4HB), Polyvinyl Alcohol (PVA), Reinforcing Cellulose Nanocrystals (CNC), Polycaprolactone (PCL), Polyglycolic acid (PGA), Polyglactin (PG), glycolide-co-e-caprolactone (PGC), Poly-L-lactide (PLLA), Poly-D,L-lactice (PDLLA), Poly-D-Lactide (PDLA), Glycomer 631, PLAGA, PLGA, Polydioxanone (PDO), Cottons, Silk fibroin, Polyethylene (UHMWPE), Polyethylene terephthalate, PEEK, PEKK, Polyester, Polypropylene, Nylon, PTFE, Stainless steel, and Carbon fiber.

One embodiment is directed to braided strands that include a set of high strength collagen fibers braided with a set of high strength polyethylene fibers, preferably high molecular weight polyethylene. Such braided strands have utility for various purposes including, for example, medical uses in orthopedics and surgery.

Some embodiments are directed to implantable biocompatible scaffolds and devices in the form of braided and bundled surgical implants, and surgical and orthopedic devices utilizing such scaffolds, including sutures, as well as related methods for their production and use to support the repair of injured soft and hard tissues, and to stabilize and support various body structures including ligaments, tendons, and joints.

In one embodiment, the scaffold comprises a suture construct that further comprises fibers manufactured using a microfluidic extrusion biomanufacturing process, which is described in further detail below. The suture is designed to be resorbed and replaced with the patient's tissue as the tissue heals completely. The implantable biocompatible scaffold is designed to promote healing in the tissue (such as ligaments, tendons, or other suitable tissues) and support accelerated return to activity by enabling early physical therapy compared to conventional alternative treatments.

The sutures and scaffolds of the embodiments may be comprised of one or more braided strands. Each braided strand may be further comprised of fibers that are braided, as well as some non-braided fibers that may be twisted, or otherwise bundled together. In one embodiment, a braided strand is comprised of two types of fibers: high strength collagen fibers and high strength polymer fibers.

As used herein, the term "high strength collagen fiber" refers to a collagen fiber that has an ultimate tensile strength that is substantially greater than that of known manufactured collagen fibers. Preferably, the ultimate tensile strength of collagen fiber embodiments according to the invention have an ultimate tensile strength of at least about 50, 60, 70, 80, 90, 100, 110, 120, 130, 140, 150 or 160 mega Pascals (MPa), where the strength of human ACL comprising of collagen fibers is about 20 MPa to 40 MPa.

The high strength collagen fibers of the embodiments may be formed according to the processes and composed of the compositions described herein, and further detailed in U.S. Patent Application Publication Number 2020/0246505, published Aug. 6, 2020, and titled "Microfluidic Extrusion," the entirety of which is herein incorporated by reference, and hereafter referred to as the "Microfluidic Extrusion Application." Accordingly, the high strength collagen fibers of the embodiments may comprise resorbable micro-fibrous type I bovine fibers that are crosslinked with a benign, biological, and biomimetic crosslinker glyoxal (a crosslinking agent found normally in human ligaments and tendons). The resulting collagen fibers, which are described in further detail below, have a relatively high tensile strength compared to other manufactured collagen strands. In particular, the collagen fibers are sufficiently strong to withstand the mechanical forces applied to the fibers during braiding on high-throughput braiding machines, as are known and used, for example, in the textile and wire industries. See, for example, the various textile and wire braiding systems from manufacturers such as Herzog GmbH (https://herzog-online.com/braidingmachines/) and Seeger USA (https://steegerusa.com/product/medical-braiders/).

The high strength polymer fibers may be high strength polyethylene fibers. As used herein, the term "high strength polyethylene fiber" refers to a fiber with an ultimate tensile strength of at least 80 MPa. In an exemplary embodiment, the high strength polyethylene fibers are ultra-high-molecular-weight polyethylene (hereafter "UHMWPE") fibers.

Various terms that are used throughout the detailed description and in the claims are collected here for reference.

As used herein, the term "fiber" refers to a filament of material, or to multiple filaments that have been twisted or otherwise bundled together. Fibers may be compared using units that measure the linear density of the fibers. For example, fiber size may be measured using the "tex" unit, which indicates the weight in grams of 1,000 meters of fiber. Dtex, or deci-tex, indicates the weight in grams per 10,000 meters of fiber.

Two or more fibers may be twisted, braided, or otherwise bundled together to form a "strand" of material. Twisted fibers may be twisted around a common axis, or one another, in the same (rotational) direction. By contrast, braided fibers may be interlaced to form more complex patterns. Bundled fibers may be held together by an exterior layer, tie, or other structure.

Parts comprised of two or more fibers that have been braided together may also be referred to as "braided structures."

The term "over-braiding" refers to the process of braiding two or more fibers over another fiber, collection of fibers, or other suitable structures. A structure that has been formed by an over-braiding process may be referred to as an "over-braided" structure.

As used herein, the term "scaffold" refers to any framework or structure that hold tissues together. A scaffold could comprise a linear structure, such as a suture, a two-dimensional structure, such as a patch or ribbon, or any suitable three-dimensional structure.

The embodiments make reference to several ligaments that may be commonly torn or ruptured and repaired using a scaffold. These include the medial collateral ligament (the "MCL"), the posterior cruciate ligament (the "PCL"), the anterior cruciate ligament (the "ACL"), and the ulnar collateral ligament (the "UCL"). Each of these ligaments are disposed at different anatomical locations and may be torn or ruptured during various kinds of physical activities.

The sutures of the present embodiments could be used in a variety of different surgical procedures. In particular, the sutures may be used in surgeries where a ligament must be repaired, internally braced, and/or replaced. Because the sutures of the embodiments have an overall tensile strength that is equal to, or greater than, the tensile strength of some ligaments and tendons in the body, the sutures can be used without other implants, to reinforce and/or repair ligaments such as the ACL, MCL, UCL, and PCL, and tendons such as the supraspinatus in the shoulder, the patellar tendon, and Achilles tendon, among others.

An exemplary procedure that may use a suture to repair a damaged ligament is shown in FIG. 1. Specifically, FIG. 1 is a schematic view of an anatomical region of the leg 102, in which a suture 100 has been attached at its ends to the femur 104 and tibia 106 in order to repair a damaged MCL 108.

As with other structures used for ACL, MCL, and PCL repairs, suture 100 may be implanted using conventional open, minimally invasive and arthroscopic techniques, into the normal ACL, MCL, or PCL anatomical tract using specialized tools, fixation devices and guides that have already been developed and are currently in use by surgeons today.

Once implanted, suture 100 will provide load share and strain relief on the associated ligament. Suture 100 will remodel in vivo into dense regularly oriented connective tissue and exhibit resorption over 8-16 weeks post implantation.

Although the exemplary embodiment shows the use of a suture comprised of braided strands for use in repairing knee ligaments, it may be appreciated that the embodiments could be used in the repair of tissue in the shoulder, foot, ankle, and other suitable repairs in the body. In some cases, the braided strands of the embodiments could also be used in plastic surgery.

Figure 2:
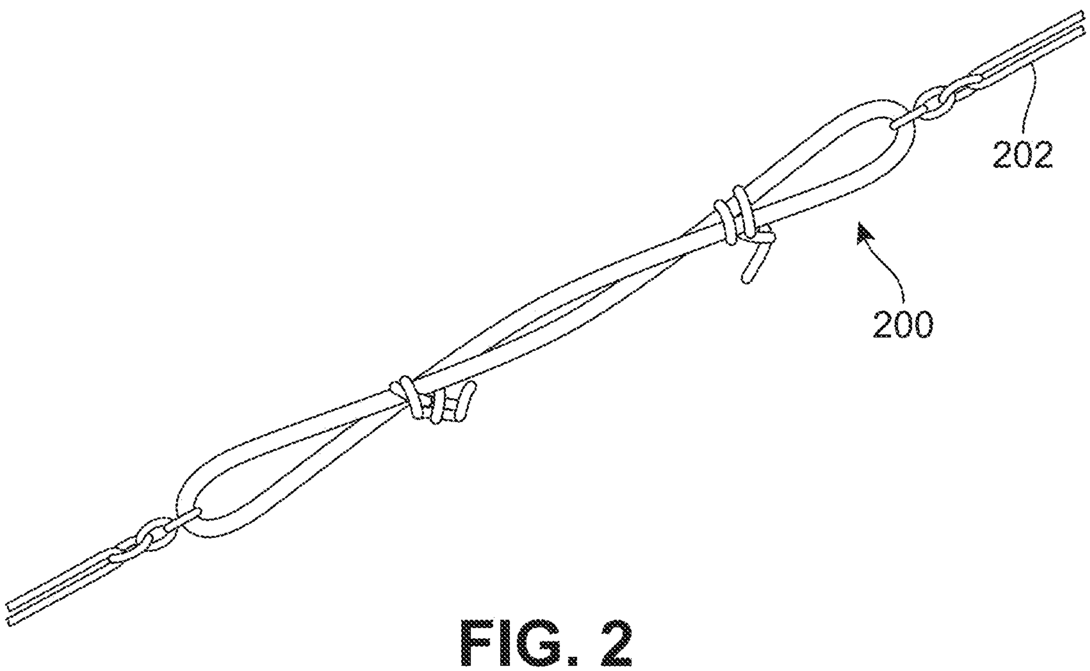
FIG. 2 is a schematic view of an implantable biocompatible scaffold, according to an embodiment.

FIG. 2 is a schematic view of a suture 200, shown in isolation. In some cases, suture 200 could comprise a single strand comprised of braided, twisted, or bundled fibers. In other embodiments, however, suture 200 could comprise multiple strands (formed of braided, twisted, or bundled fibers) that have been looped, or otherwise arranged, together. In some cases, a bundle or loop of strands could be joined on each end by non-absorbable polyethylene sutures 202 or other anchors (not shown) for bone fixation.

Sutures of the embodiments could be configured with different geometries. In some embodiments, a suture comprised of one or more braided strands may have a rounded cross-sectional shape. Other embodiments of sutures could have a flattened geometry. Still other embodiments of sutures could include combinations of flattened and rounded portions. For example, one embodiment of a suture could comprise a flattened middle portion with rounded ends that facilitate tie down properties for the suture. Likewise, at the level of an individual strand, braided strands could also be configured with flattened geometries, rounded geometries, or a combination of flattened and rounded geometries. As described below, one way to achieve a rounded strand geometry is to over-braid fibers onto a core of straight or twisted fibers. Flattened braided strands can be made using flat-braiding techniques.

While the embodiment of FIG. 2 depicts a suture comprised of braided strands, other embodiments may comprise fibers braided strands incorporated into a variety of other suitable geometries and structures, including, for example, patches, braces, and tapes.

Figure 3:
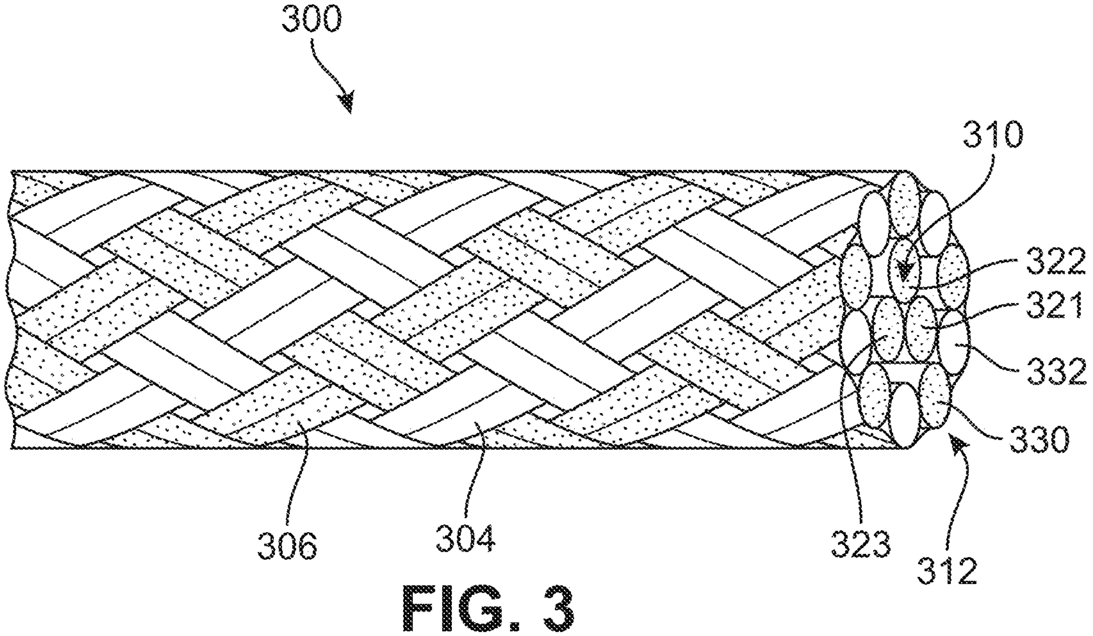
FIG. 3 is a schematic view of a strand that may comprise part of an implantable biocompatible scaffold, where the strand is formed of a core of non-braided fibers, and an outer layer of braided fibers, according to an embodiment.

FIG. 3 is a schematic view of a section of a single strand 300. Strand 300 may be further comprised of a set of collagen fibers 304 and a set of polymer fibers 306. Sets of fibers may include one, two, three, or more than three fibers. For purposes of illustration, polymer fibers are shown with shading in the Figures to distinguish them from the collagen fibers.

Collagen fibers 304 may be high strength collagen fibers according to the embodiments. The high strength collagen fibers may have sufficiently higher tensile strength than conventionally manufactured collagen fibers. Specifically, the fibers may be strong enough to withstand stresses imparted to the fibers when manipulated on industrial scale braiding machines. The specific tensile properties of these high strength collagen fibers are described in further detail below and shown, for example, in FIG. 16.

Polymer fibers 306 may comprise a high strength polyethylene material. More specifically, in some embodiments, polymer fibers 306 are ultra-high-molecular-weight polyethylene fibers 306.

The fibers of strand 300 may be further arranged into a core 310 and an outer layer 312. Core 310 may comprise a plurality of fibers with a straight or twisted configuration. That is, the fibers in core 310 may not be braided. In contrast, outer layer 312 is comprised of fibers that have been over-braided along the fibers of core 310. Over-braiding fibers onto a core of straight or twisted fibers may help strand 300 take on a generally rounded cross-sectional shape. As described in further detail below, in some embodiments, the core may be omitted.

In the exemplary embodiment, core 310 includes three fibers. These include a first polymer fiber 321, a second polymer fiber 322, and a third polymer fiber 323. By contrast, outer layer 312 is seen to include eight fibers. These include four polymer fibers 330 that alternate with four collagen fibers 332 along the exterior of strand 300.

For purposes of illustration, strand 300 is shown with a particular braided pattern, visible along its side. However, it may be appreciated that embodiments are not limited to a particular braiding pattern. Any suitable braided pattern could be used and selected according to various factors such as the number of fibers used and the sizes of the fibers.

Scaffolds, including sutures, of the present embodiments can be formed from a single strand, or from multiple strands that are looped, bundled, braided, twisted, or otherwise joined together. For example, referring back to FIG. 2, suture 200 may be formed from a single strand, such as strand 300 shown in FIG. 3, or else from multiple strands like strand 300 that have been bundled, twisted, and/or braided together into the looped configuration shown in FIG. 2.

In still other embodiments, strands similar to strand 300 could be arranged into two-dimensional configurations to form ribbons, rectangular patches, or other two-dimensional implants used for tissue repair, tissue augmentation, wound closure and delivery of biological agents such as cells, cell-based products, genes, growth factors, small molecules, drugs or other therapeutic agents as would be known to persons skilled in the art.

Figure 4:
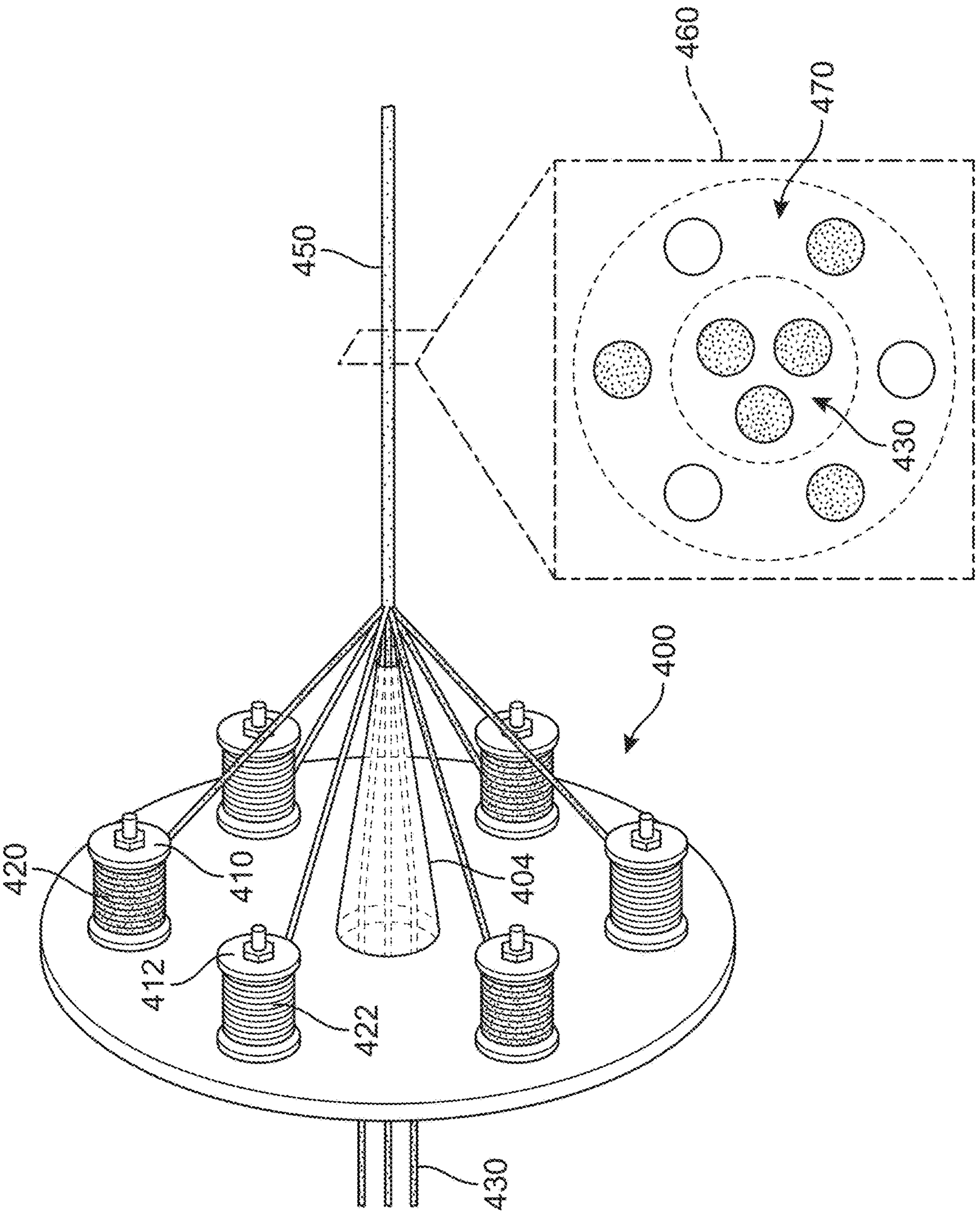
FIG. 4 is a schematic view of a machine and process for making a strand comprised of braided and non-braided fibers, according to an embodiment.

FIG. 4 is a schematic view of an exemplary braiding process for forming a strand that comprises a core of fibers and an over-braided outer layer of fibers. Referring to FIG. 4, a braiding machine 400 may be used to over-braid fibers onto a central core, thereby forming a braided strand 450. Braiding machines may generally include spools, or bobbins, that are moved or passed along various paths on the machine by carriers.

For purposes of illustration, braiding machine 400 is shown with six bobbins that ride on six carriers (not shown). However, it may be appreciated that in other embodiments additional bobbins/carriers could also be used. In one embodiment, for example, a 24-carrier braiding machine could be used.

Each carrier includes a bobbin with either high strength polymer fiber or high strength collagen fiber. For example, a first bobbin 410 holds a high strength polymer fiber 420. Likewise, a second bobbin 412 holds a high strength collagen fiber 422. As the braiding machine is run and bobbins are passed around between carriers, braided strands extending from the bobbins towards a center of the machine may converge at a "braiding point".

Core fibers 430 are fed from behind into a central channel of machine 400 and exit out through a nozzle 404. Strands from each carrier are drawn out to a braiding point just beyond nozzle 404 so that the strands can be over-braided around core fibers 430 to form a two layered construction.

An enlarged cross-sectional view 460, taken along a section of braided strand 450, shows six fibers braided together in an outer layer 470. The outer layer 470 of fibers encircle the core fibers 430. In this exemplary embodiment, core fibers 430 all comprise polymer fibers. Also, outer layer 470 is comprised of three collagen fibers and three polymer fibers arranged in an alternating configuration. For reference, dotted lines are shown in the enlarged cross-sectional view of braided strand 450 to indicate approximate boundaries of the core and outer layer. However, these boundaries are not intended to represent physical structures or barriers.

A braided strand can be configured with different properties according to the number, type, and spatial arrangement of fibers used, and the types of copolymer(s) used in the fibrous constructs. These different properties include, but are not limited to: tensile strength, elasticity, size (e.g., diameter), weight, biocompatibility, visibility, and cost.

FIGS. 5-14 are schematic views of various possible fiber configurations within a braided strand. As already described, the embodiments include an inner core of fibers and an over-braided outer layer of fibers. It may be appreciated that the material properties of a braided strand may depend on the number, size, shape, type, and spatial arrangements of fibers both within the core and in the outer over-braided layer.

Figure 5:
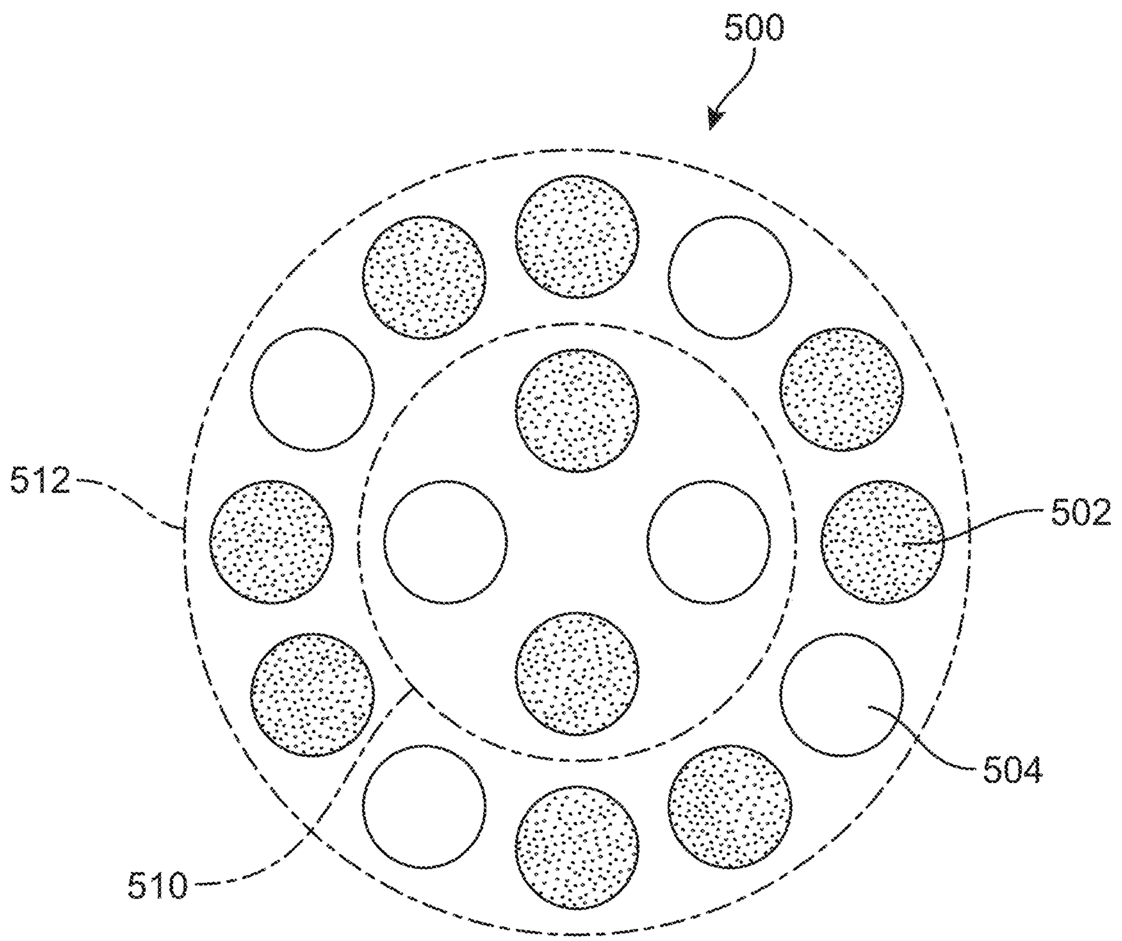
FIGS. 5-14 comprise various schematic views depicting different possible configurations of collagen fibers and high strength polymer fibers in a strand, according to various embodiments.

FIG. 5 is a schematic view of an exemplary braided configuration. In this embodiment, a braided strand 500 includes sixteen total fibers, including both high strength polymer fibers 502 (specifically UHMWPE fibers) and high strength collagen fibers 504. More specifically, core 510 comprises four fibers, while outer layer 512 is comprised of the remaining twelve fibers. In this example, core 510 includes two polymer fibers and two collagen fibers. Of the remaining fibers in outer layer 512, four are collagen fibers while eight are polymer fibers. More specifically, the fibers in outer layer 512 are arranged at this particular location along the strand such that there are two polymer fibers disposed between each pair of adjacent collagen fibers. The relatively large number of polymer fibers results in a strand with about ninety percent of the tensile strength of a similarly configured strand in which each of the sixteen fibers are UHMWPE polymer fibers (that is, in a similarly constructed strand where all fibers are polymer fibers).

Figure 6:
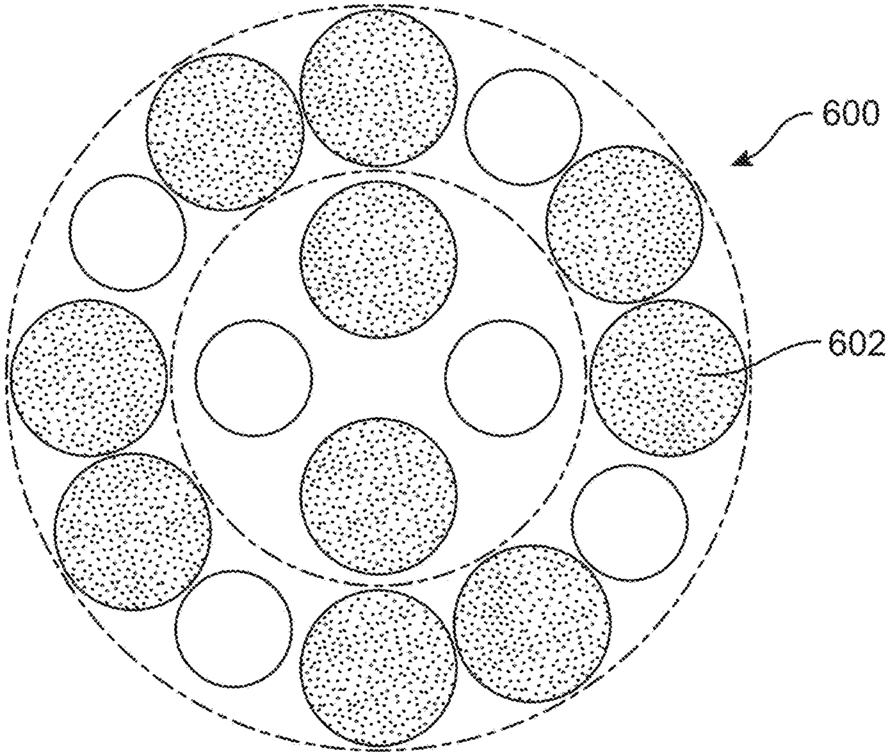

FIG. 6 is a schematic view of another exemplary braided configuration. The configuration of braided strand 600 in FIG. 6 may be substantially similar to that of braided strand 500 in FIG. 5. However, the polymer fibers 602 in this embodiment have a larger linear density than the polymer fibers 502 of the previous embodiment. For purposes of illustration, this increased linear density of polymer fibers 602 compared to polymer fibers 502 is represented with larger diameter fibers. In some embodiments the polymer fibers of braided strand 500 have a linear density of 110 dTex, while the polymer fibers of braided strand 600 have a linear density of 165 dTex. This increased size for the polymer fibers may provide better cushioning for the adjacent collagen fibers.

Figure 7:
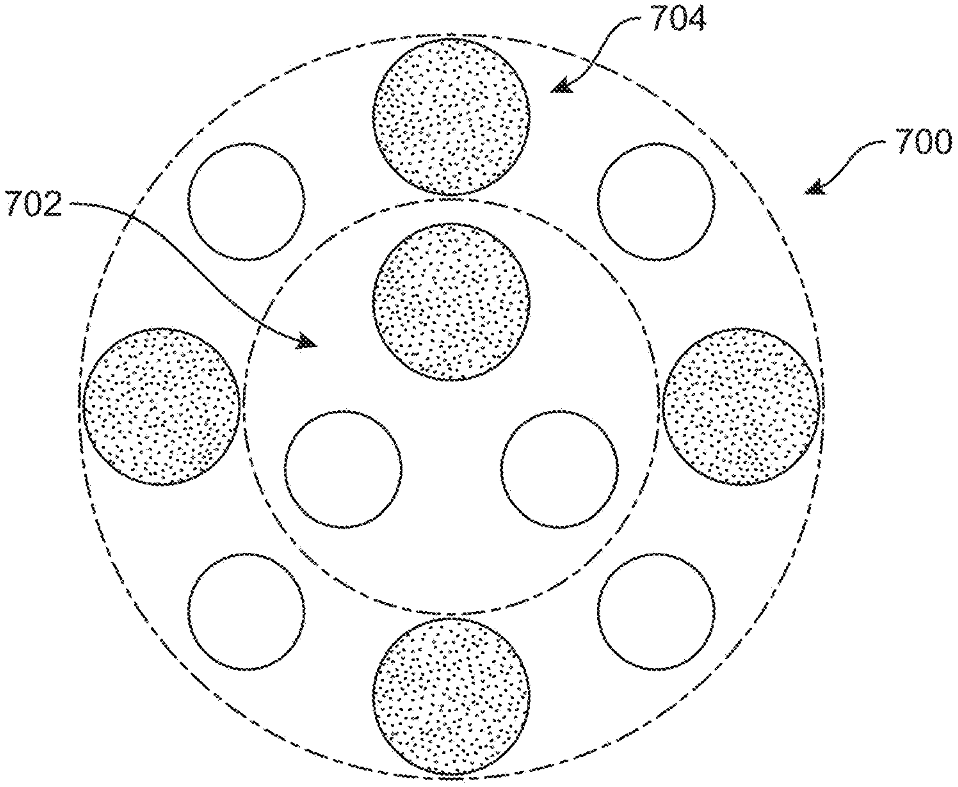

FIG. 7 is a schematic view of another exemplary braided configuration. The configuration of FIG. 7 includes a braided strand 700 with three core fibers 702 and eight fibers 704 in the outer layer (for a total of eleven fibers). The three core fibers are further comprised of two collagen fibers and a single polymer fiber. The outer layer includes four polymer fibers alternating with four collagen fibers. This configuration provides a strand with a higher collagen percentage relative to the previous embodiments (approximately 55% for strand 700 vs. approximately 38% for strand 500 and strand 600).

Figure 8:
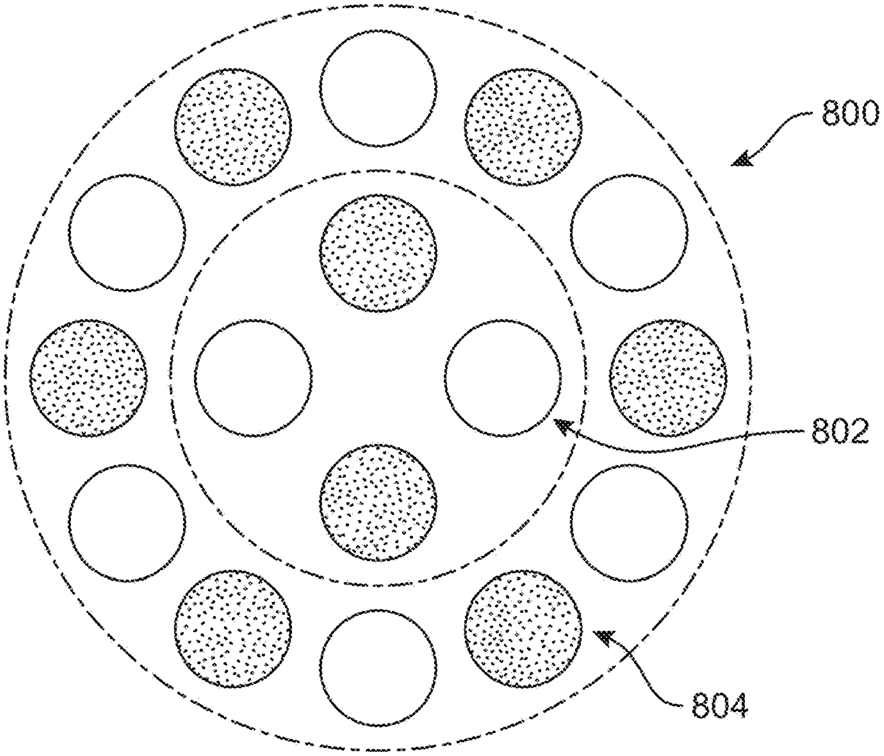

FIG. 8 is a schematic view of another exemplary braided configuration. The configuration of FIG. 8 includes a braided strand 800 with four core fibers 802 and twelve outer fibers 804 in the outer layer (for a total of sixteen fibers). Both the core and outer layer have an equal number of collagen and polymer fibers, so that overall the strand has eight collagen fibers and eight polymer fibers. Braided strand 800 retains approximately 85% of the tensile strength of a similar strand comprised solely of polymer fibers, and is comprised of approximately 50% collagen.

Figure 9:
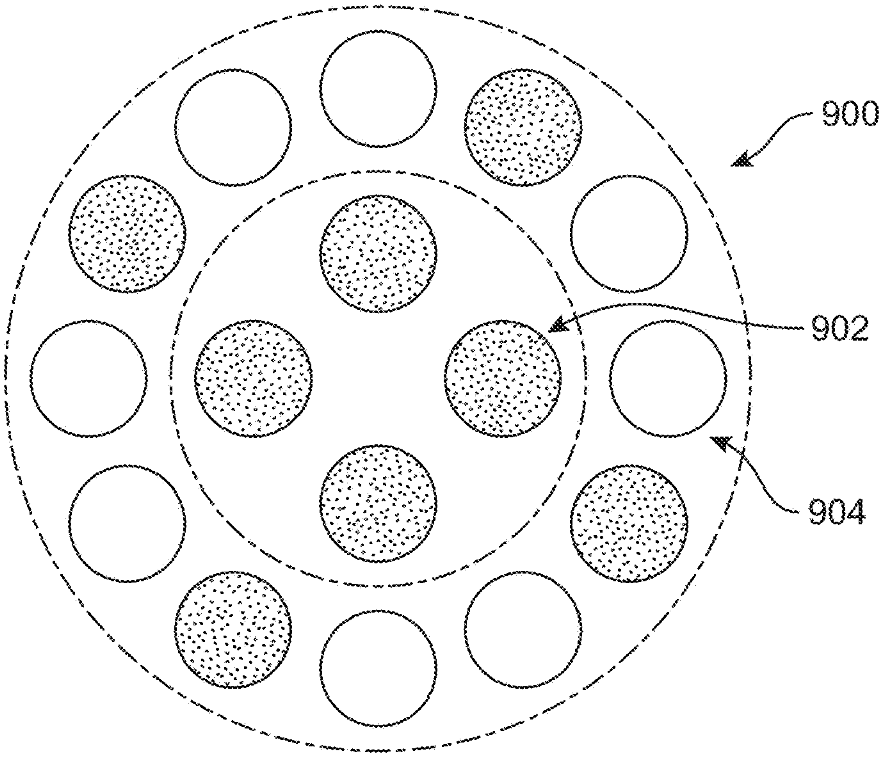

FIG. 9 is a schematic view of another exemplary braided configuration. The configuration of FIG. 9 includes a braided strand 900 with four core fibers 902 and twelve outer fibers 904 in the outer layer (for a total of sixteen fibers). In this example, the core is comprised only of polymer fibers. Of the remaining fibers in the outer layer, eight are collagen fibers while four are polymer fibers. More specifically, the fibers in the outer layer are arranged at this particular section of the braided strand such that there are two collagen fibers disposed between each pair of adjacent polymer fibers. The relatively large number of polymer fibers results in a strand with about ninety percent of the tensile strength of a similarly configured strand in which each of the sixteen fibers are UHMWPE polymer fibers (that is, in a strand that lacks any collagen fibers). Moreover, this embodiment positions all of the collagen strands on the outside of the strand, where they can more easily contact tissue in the body to better facilitate healing.

Figure 10:
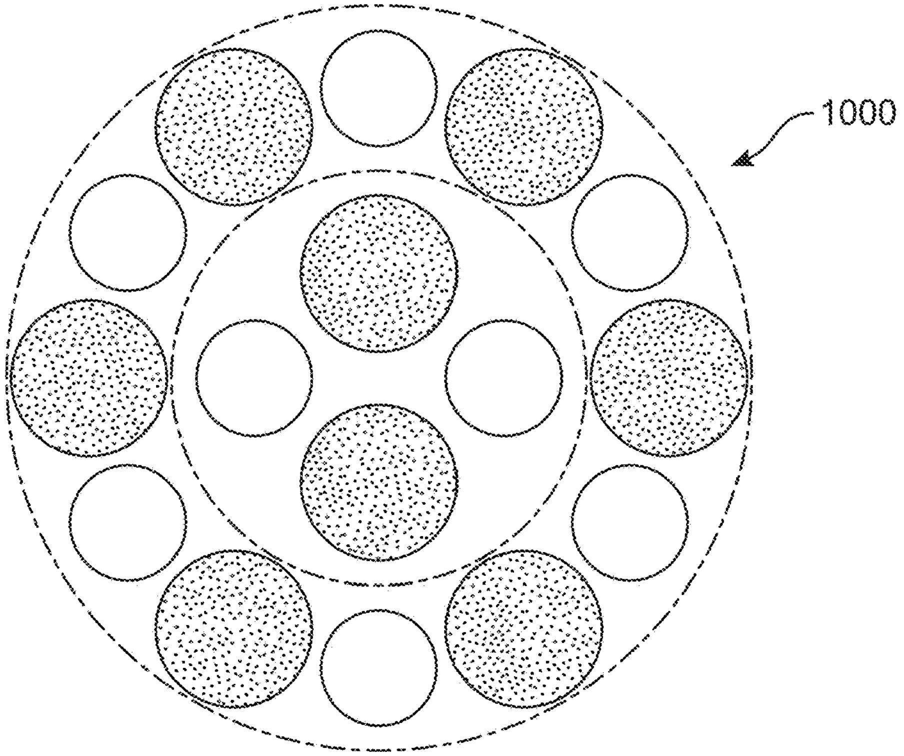

FIG. 10 is a schematic view of another exemplary braided configuration. The configuration of a braided strand 1000 in FIG. 10 may be substantially similar to that of braided strand 900 in FIG. 9. However, whereas the polymer fibers of braided strand 900 have a linear density of 110 dTex, the polymer fibers of braided strand 1000 have a linear density of 165 dTex. This increased size for the polymer fibers may facilitate improved cushioning for the collage fibers on the exterior of the strand.

Figure 11:
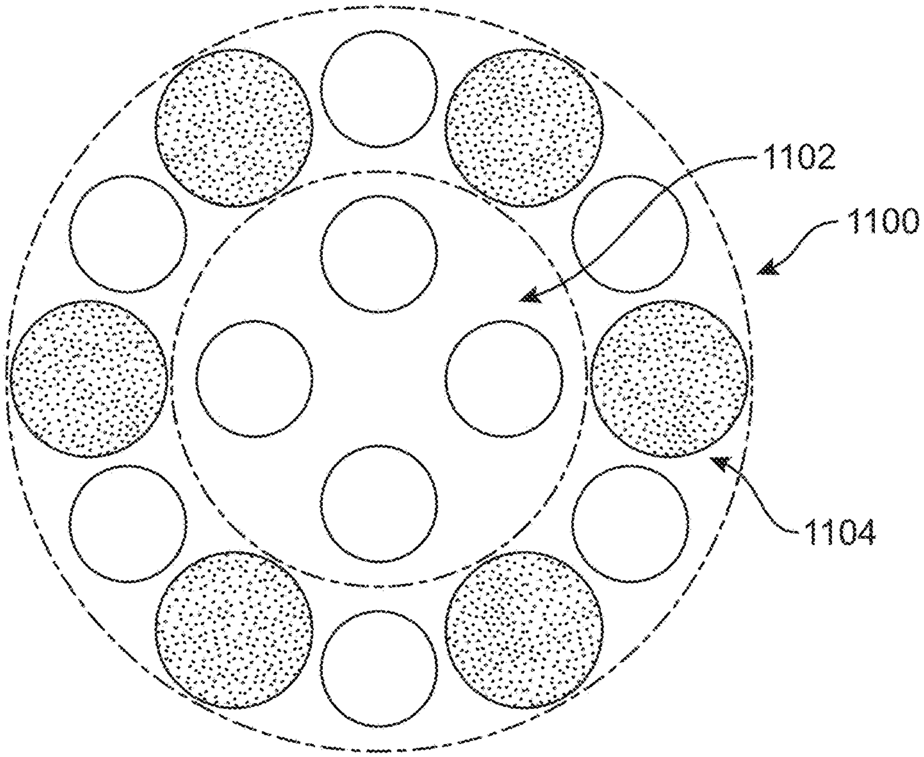
Figure 12:
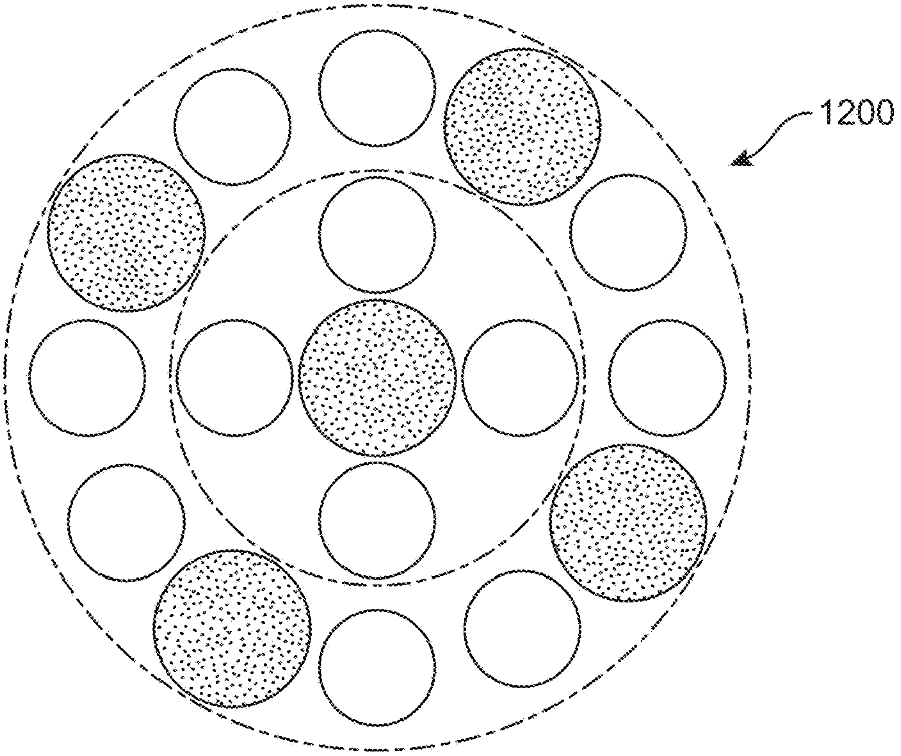

FIGS. 11-12 illustrate schematic views of braided configurations where more than half the fibers in each braided strand are collagen fibers. Specifically, FIG. 11 depicts a braided strand 1100 with six polymer fibers and ten collagen fibers. In this case, the core 1102 is comprised of four collagen fibers, while the outer layer 1104 include six collagen fibers alternating with six polymer fibers.

In FIG. 12, braided strand 1200 is comprised of five polymer fibers and twelve collagen fibers. Moreover, the core includes four collagen fibers surrounding a polymer fiber (for a total of 5 core fibers). The outer layer comprises eight collagen fibers and four polymer fibers. Braided strand 1200 retains approximately 75% of the tensile strength of a similar strand comprised solely of polymer fibers.

Figure 13:
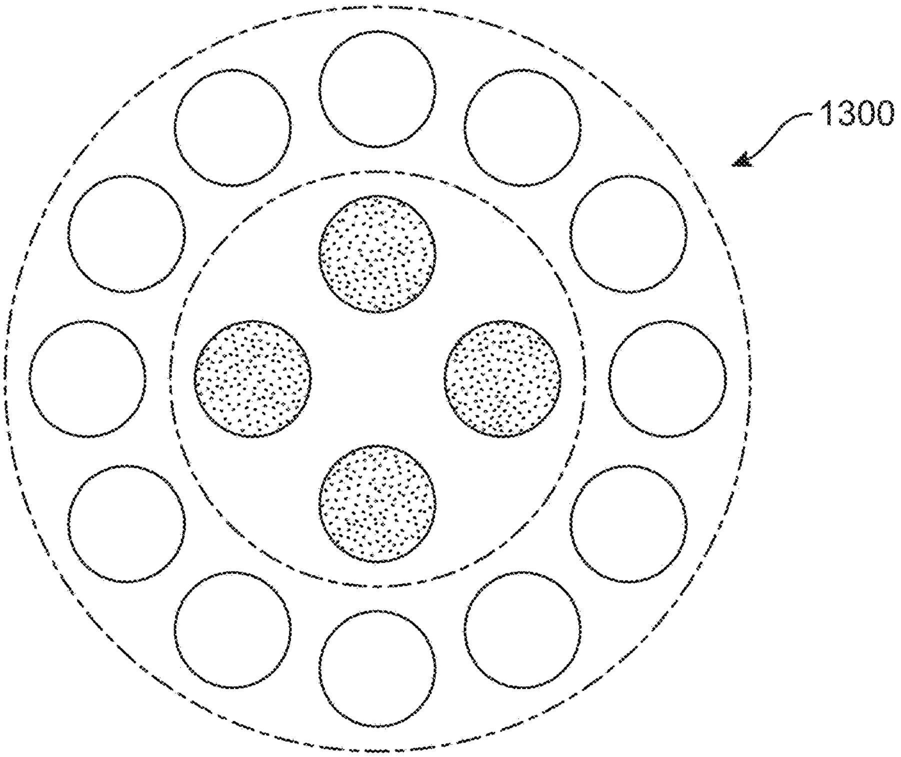

FIG. 13 is an exemplary embodiment of a strand 1300 comprised of a core consisting of only polymer fibers and an outer layer comprised of only collagen fibers braided together. Here, the core polymer fibers help provide a rounded shape for the strand and add tensile strength to the strand. But by using all collagen fibers along the outside, the strand can promote healing everywhere that the exterior of the strand comes into contact with damaged tissue.

Figure 14:
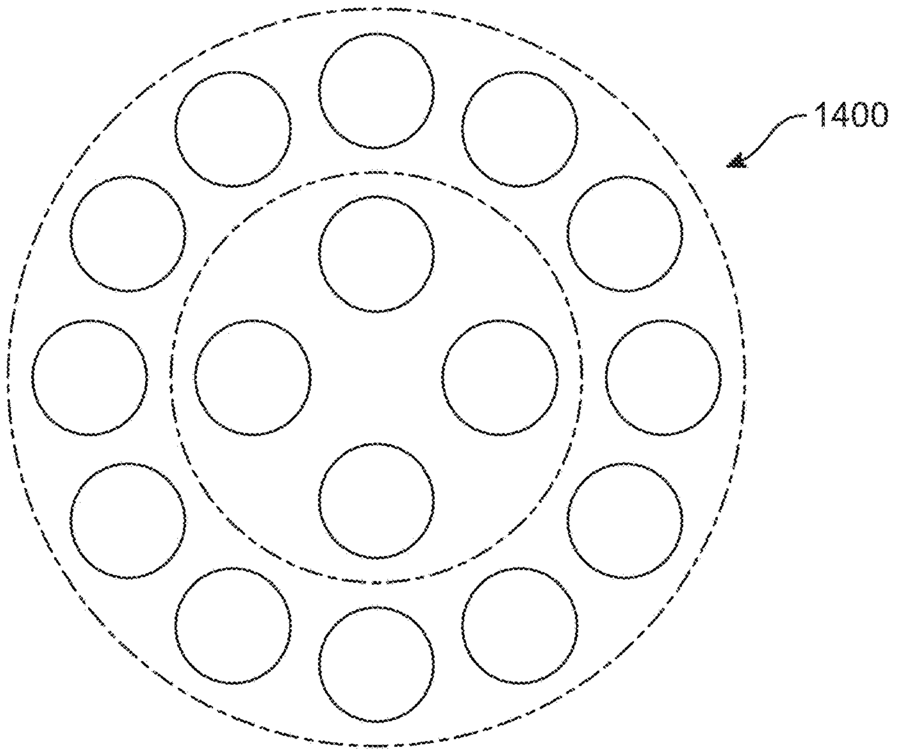

FIG. 14 is an exemplary embodiment of a strand 1400 consisting only of collagen fibers. In this case both the core and outer braided layer are comprised of only collagen strands. Using only collagen may maximize the potential of the strand to contribute to healing, by eliminating the presence of polymer fibers which may be non-bioabsorbable and which may not promote new tissue growth. Moreover, the use of high strength collagen strands as disclosed in the embodiments may provide a strand that has similar, or greater, ultimate tensile strength than an associated ligament or other tissue to be repaired using the strand.

As seen in FIGS. 5-14, various configurations of a braided strand may include one or more collagen strands on in the outer layer. This not only promotes healing, but also facilitates better tie down properties for sutures comprised of the braided strand, since the collagen strands are generally "stickier" than the UHMWPE strands. By providing configurations of braided strands where a significant fraction of the strands in the outer layer are collagen strands (e.g., more than 30% of the total strands), the embodiments eliminate any need for introducing another type of strand and/or coating for strands that might be required to ensure sutures comprised of the braided strands can be tied down.

The embodiments comprise strands formed by braiding high strength polyethylene fibers with collagen fibers having a relatively high tensile strength. For purposes of describing the tensile properties of various fibers, the embodiments make use of various terminology including ultimate tensile strength, yield strength, modulus of elasticity, and strain at break. As used herein, "ultimate tensile strength," or UTS, is the maximum stress that a material can withstand while being stretched or pulled before breaking. As used herein, the "yield strength" or "yield stress" is the stress corresponding to the yield point at which a material begins to deform plastically. As used herein, the "modulus of elasticity" is a measure of the stiffness of an elastic material. Specifically, it is a ratio of stress along an axis to strain along the same axis. As used herein, the term "strain at break" is a measure of the change in length of a material at the point where the material breaks under tension.

Figure 15:
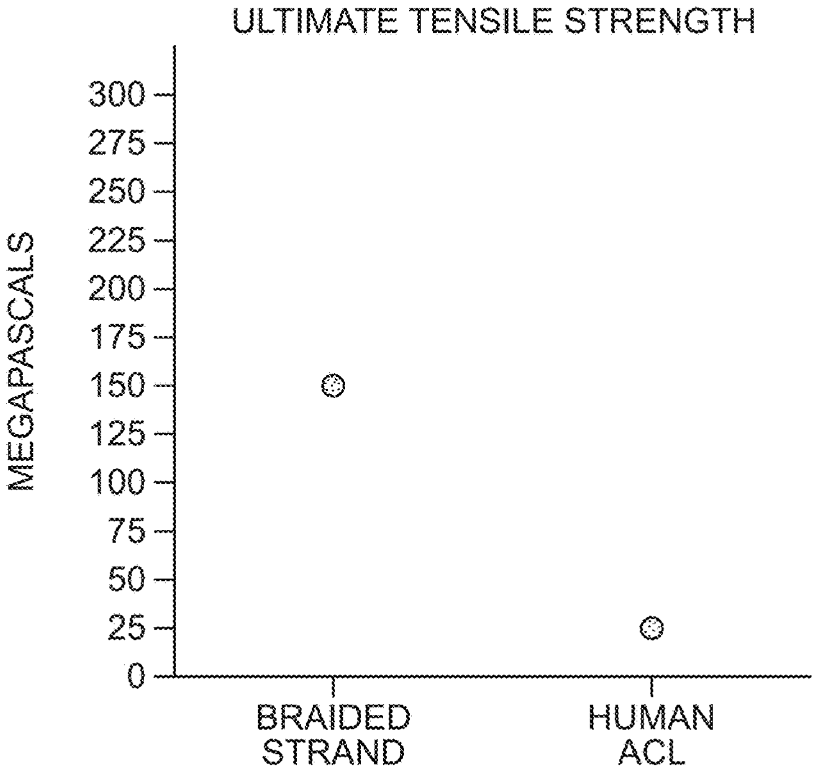
FIG. 15 is a schematic view of a chart showing the tensile properties of a braided strand of the embodiments and a human ACL.

The braided strands of the embodiments have sufficiently greater tensile strength than corresponding ligaments and tendons in the body, as seen in FIG. 15, which compares the tensile strength of an exemplary braided strand according to the embodiments with the tensile strength of a human ACL. In this example, an exemplary braided strand has an ultimate tensile strength of approximately 150 MPa, while a human ACL has a UTS between 25 and 50 MPa.

To achieve braided strands of the embodiments, collagen fibers with relatively high tensile strengths are used, as already discussed. FIG. 16 is a schematic table showing ultimate tensile strength for high strength collagen fibers employed in the embodiments disclosed herein and of UHMWPE fibers manufactured according to known processes. In particular, the values shown in the chart are for a high strength collagen fiber that is comprised of individual collagen filaments that have been bundled together to form a single continuous fiber with an average diameter approximately in a range between 90 μm and 180 μm.

The Table in FIG. 16 shows minimum and maximum values for ultimate tensile strength for the two listed types of fiber. As seen in the table of FIG. 16, the ultimate tensile strength (UTS) of the high strength collagen fibers varies approximately between 50 and 500 Megapascals (MPa), whereas the UHMWPE fibers have a UTS that varies approximately between 3000 MPa and 5000 MPa. Therefore, the UTS of the high strength collagen fibers varies approximately in a range between 1.0% and 16.7% of the UTS of the UHMWPE fibers.

The mechanical properties of the high strength collagen fibers described herein allow for the manipulation of the fibers and their production into the braided strands of the embodiments. While UHMWPE is stronger than these high strength collagen strands, the collagen strands are still strong enough to withstand the stresses imparted to the strands by high throughput and conventional braiding machines that allow the braided strands to be manufactured at scale. Moreover, the relatively high strength of the collagen fibers allows for greater flexibility in constructing a braided strand using both collagen and UHMWPE fibers. Because the high strength collagen fibers provide some strength to the braided strand, fewer UHMWPE fibers may be required to maintain a minimum desired tensile strength and other parameters for the braided strand. This allows for a greater ratio of collagen fibers to UHMWPE fibers, which is more suitable for healing damaged tissue.

In still other embodiments, collagen fibers can be manufactured with a range of different tensile strengths, by varying the cross-linking compounds used, collagen collection methods, and other suitable characteristics. It may be appreciated, therefore that the values given for various mechanical properties of high strength collagen fibers are only intended as examples and should not be construed as limiting.

Figure 17:
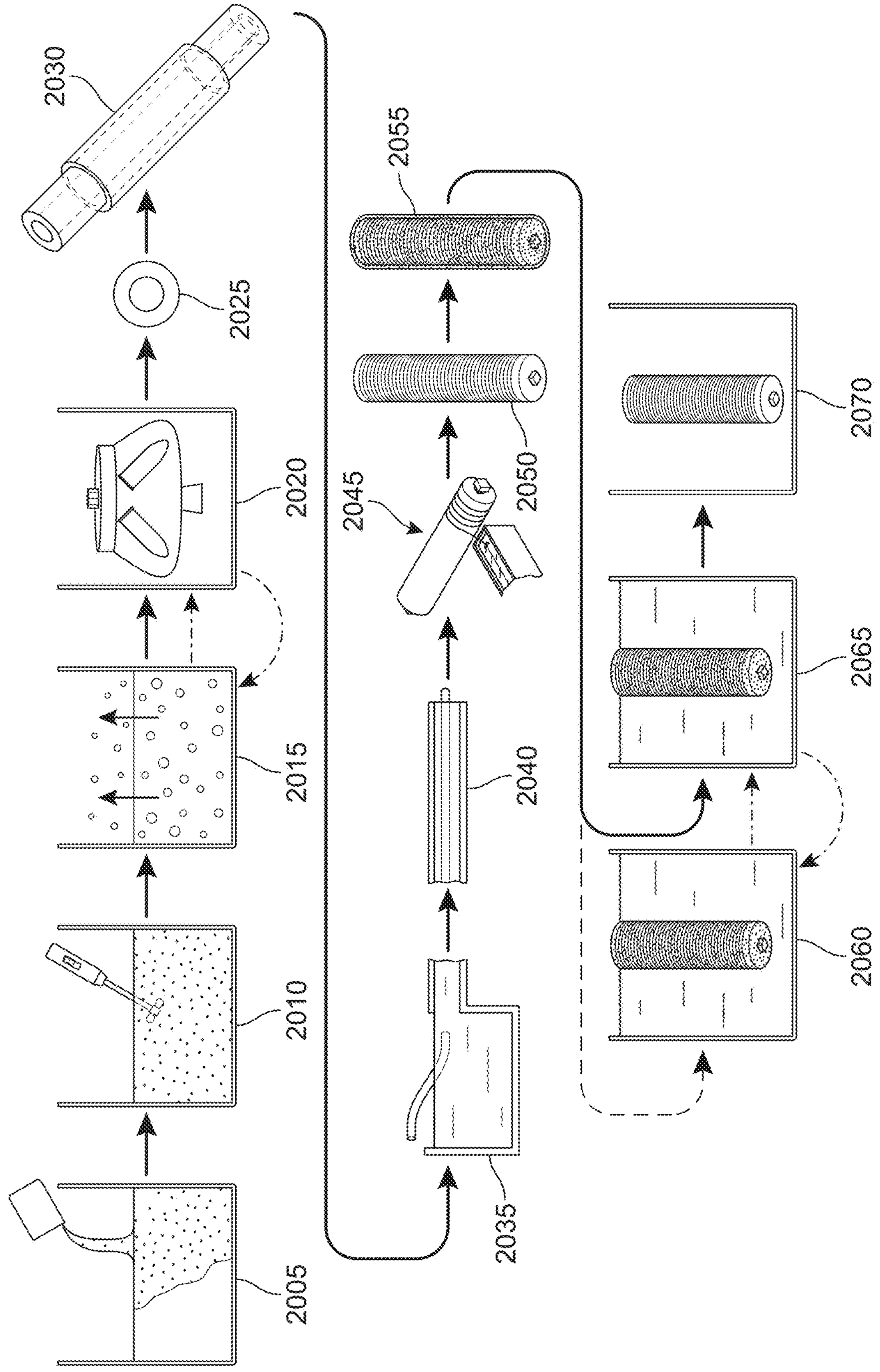
FIG. 17 is a schematic view of a multi-step process for creating collagen strands, according to an embodiment.

FIG. 17 illustrates a schematic multi-step process, and associated system, whereby high strength collagen fibers can be formed. That is, collagen fibers that have substantially greater tensile properties than conventionally manufactured collagen fibers. The system and method may be described as comprising four sections or manufacturing areas. A collagen solution is prepared in the first section, and collagen fiber is formed in the second section. The collagen fiber then is collected in the third section and then may be post-processed to yield wet or dry collagen fiber in the fourth section, post-treatments, or end of treatment.

The steps in the system and method illustrated in FIG. 17 may be grouped into four categories, as follows: (1) Preparing Collagen Solution, including step 2005 through step 2020; (2) Forming Collagen Fiber, including step 2025 through step 2030; (3) Collecting Collagen Fiber, including step 2035 through step 2050; and (4) Post-Treatment or End Treatment, including step 2055 through step 2070.

As seen at step 2005 of FIG. 17, collagen is combined with an acidic solution and stirred thoroughly at step 2010. In some embodiments, the acid is between about 0.01 M and about 0.50 M acetic acid. In other embodiments, the acid is between about 0.01 M and about 0.50 M hydrochloric acid. The solution may be degassed at step 2015, and then centrifuged at step 2020 to remove residual bubbles. It will be noted that, in some cases, the centrifuging step may be omitted. Resultant collagen solution is extruded from a needle (or spinneret), and there may be a second needle co-axial therewith that supplies a formation buffer solution in step 2025. The resultant forming fiber may continue in through a formation tube in step 2030. The resultant product is a formed collagen fiber.

The fiber then continues to a collection system, wherein the fiber is separated from the formation buffer solution at step 2035 and dehydrated at step 2040. The collagen fiber is recovered at step 2045 and air-dried at step 2050. Then, postprocessing may be carried out, as illustrated at step 2055, step 2060, step 2065, and step 2070. Air-dried collagen fiber on a spool is submerged in cross-linking solution at step 2055, optionally washed at step 2060, air-dried at step 2065, and desiccated to form dried fiber at step 2070. As illustrated in FIG. 17 by the dot-dash line, material may be optionally washed at step 2060, dried at step 2065, and returned to wash step 2060.

Alternatively, collagen is injected into a bath of formation solution to form a fiber. In this system, a second needle for coaxial injection of formation buffer is not necessary. Collagen thus injected is introduced to a collection system through dehydration at step 2040. The fiber then is processed in accordance with the remainder of the processing steps.

FIG. 17 provides a generalized view of a system and method for carrying out an embodiment of the disclosure. Additional details and disclosure are included in the Microfluidics Application.

Figure 18:
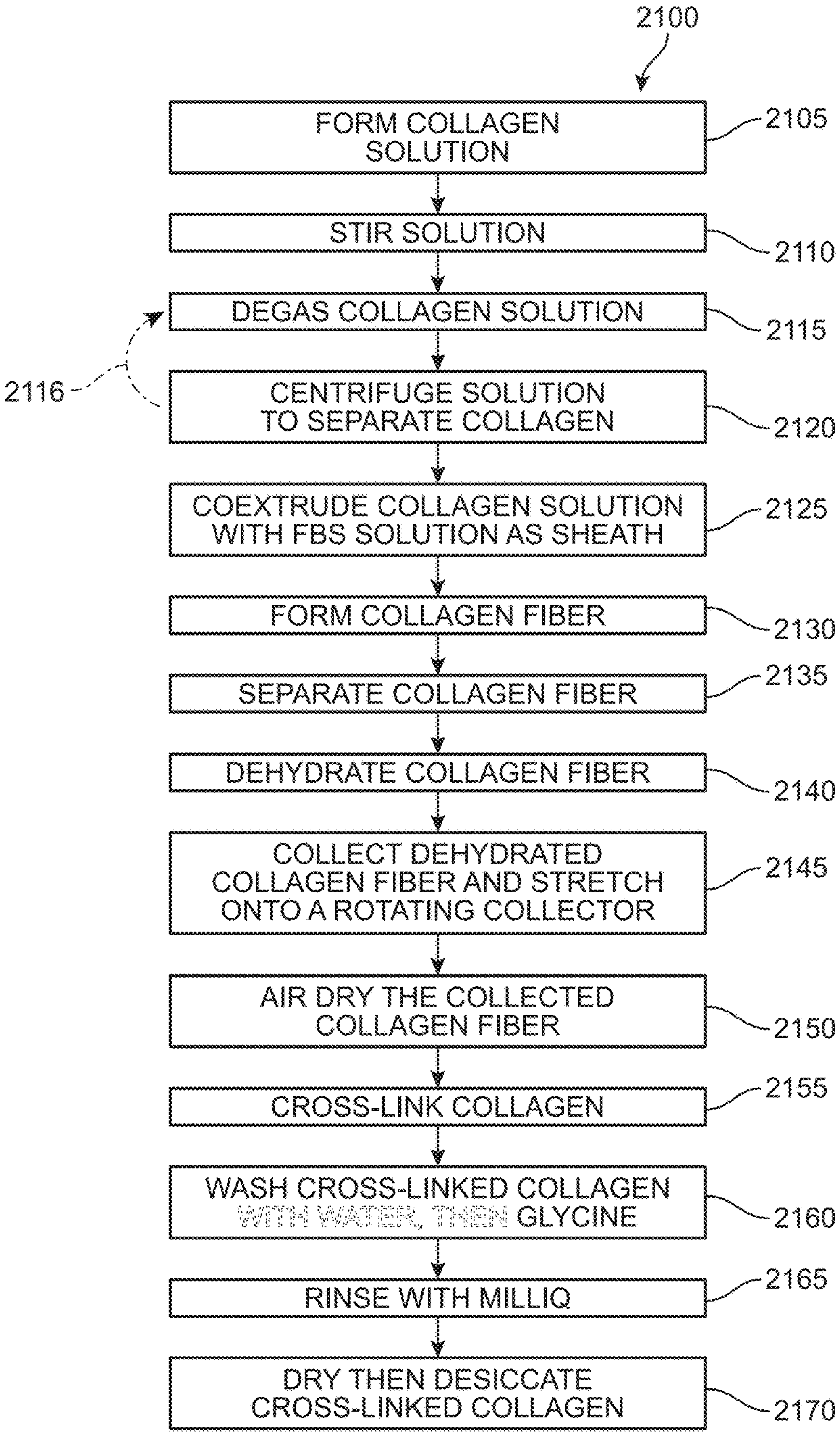
FIG. 18 is a schematic view of another process for creating collagen strands, according to an embodiment.

Another embodiment of the exemplary method is shown in FIG. 18. Method 2100 begins with step 2105, where a collagen solution is formed. A biopolymer may be mixed with the collagen. Collagen is dissolved in an acidic solution to form a viscous solution. The solution is stirred at step 2110 to ensure thorough mixing. The mixed solution may have entrapped gas, and so may be degassed one or more times in degasser step 2115. The collagen solution then may be centrifuged in step 2120. Optionally, the degas/centrifuge steps may be repeated, as shown by the dot-dash line 2116 on FIG. 18, to reduce the volume of gas entrapped in the solution. Thus-prepared collagen solution is formed into a collagen fiber by coaxial extrusion with a formation buffer solution that serves as a sheath for the fiber core in step 2125. The formation buffer solution volumetric flow rate typically is at least twice the volumetric flow rate of the forming collagen. This arrangement suppresses formation of individual fibrils; stretches and orients the fiber; and may smooth the surface of the fiber by imparting flow-induced crystallization to the fiber.

The collagen fiber then is collected. As formation of the collagen fiber is completed at step 2130, the collagen then is separated from the formation buffer solution at step 2135 and dehydrated in a dehydrating solution at step 2140.

The dehydrated collagen then is collected on a rotating spool in step 2145, which further stretches the fiber by rotating at a rate greater than, and typically about twice, the rate at which the fiber is supplied from dehydrating solution step 2140. Thus, collected fiber then is air-dried on the spool in step 2150.

In an alternative embodiment, collagen solution is formed into a collagen fiber by direct injection into formation buffer solution. Thus, step 2125 is skipped. The fiber is collected, separated from formation buffer solution, and dehydrated in a dehydrating solution at step 2140. The fiber is collected on a rotating spool in step 2145, which collects fiber at a speed of between about 2 times the formation speed and about 4 times the formation speed.

Fiber that has been air-dried on the spool then may be postprocessed. Fiber may be cross-linked in a cross-linking solution at step 2155, and then may be rinsed at step 2160. The fiber then is air dried at step 2165 and desiccated at step 2170 to yield dry cross-linked collagen fiber.

The equipment used in making collagen fiber is made of conventional materials of construction suitable for resisting attack by any of the raw materials used to make collagen fiber in accordance with embodiments of the disclosure. Metals, plastics, and other materials have properties and characteristics suitable to resist attack by raw materials, intermediates, solvents, and products during manufacture of collagen fiber.

The process described herein is used to form a collagen fiber that has substantially better tensile properties than other collagen fibers that may be available commercially. Specifically, the collagen fibers may have one or more of the following characteristics: (1) an ultimate tensile strength of at least 80 MPa; (2) a modulus of elasticity of at least 1200 MPa; (3) a strain at break of between about 4 percent and about 12 percent elongation; and (4) an average fiber diameter between about 90 μm and about 180 μm. Moreover, the collagen fiber at least maintains 20-30% of its dry strength after soaking in biological fluid for about 1 hour.

Still further, the fiber exhibits an ordered, longitudinally-oriented structure, and the fiber allows infiltration of cellular growth.

As described above, the disclosed scaffold or suture construct is intended to be implanted into or along the normal anatomical tract of various ligaments or other suitable tissues, to aid in the repair of type 1 and 2 ruptures/tears. Performance testing has demonstrated that the device will have the required mechanical and physical properties to function as a useful construct in ACL and PCL surgical repairs with the product having average yield loads exceeding those of native ligaments. Preferably, such devices will be terminally sterilized using electron beam sterilization (or ethylene oxide sterilization) and will be intended for single use only.

The device will provide load share and strain relief on the primary ACL, MCL, or PCL surgical repair. The device will remodel in vivo into dense regularly oriented connective tissue and exhibit resorption over 8-16 weeks post implantation. As with other suture constructs used for ACL and PCL repairs, the device will be implanted, using conventional arthroscopic techniques, into the normal ACL or PCL anatomical tract using specialized tools, fixation devices and guides that have already been developed and are currently in use by surgeons today.

An exemplary product which may be manufactured using the braiding techniques described above is surgical sutures. Round, flat, and/or hollow sutures may be formed using the braiding techniques disclosed herein. In some embodiments, such braided sutures may be formed of a combination of high strength collagen (e.g., Type I bovine collagen fibers) and a synthetic fiber, such as UHMWPE (e.g., Dyneema®). In some embodiments, collagen-UHMWPE co-braided sutures may be formed of approximately 50% collagen and 50% UHMWPE fibers. Testing has shown these 50/50 configurations to be as strong as conventional fully synthetic high-strength sutures. Such sutures may be suitable for orthopedic use, for example tendon/ligament approximation and ligation.

Figure 19:
FIG. 19 is a fluorescence image of a braided #2 suture in green channel, artificially colored to black and white.

FIG. 19 is a fluorescence image of a braided #2 suture in green channel, artificially colored to black and white. The collagen fibers appear light colored, and the UHMWPE fibers appear dark.

Figure 20:
FIG. 20 is a fluorescence image of a braided 2.5 mm suture tape in green channel, artificially colored to black and white.

FIG. 20 is a fluorescence image of a braided 2.5 mm suture tape (i.e., flat) in green channel, artificially colored to black and white. Again, the collagen appears light and the UHMWPE appears dark. Notably, the dark color in the middle of the image indicates the presence of a UHMWPE core within the braided structure.

Figure 21:
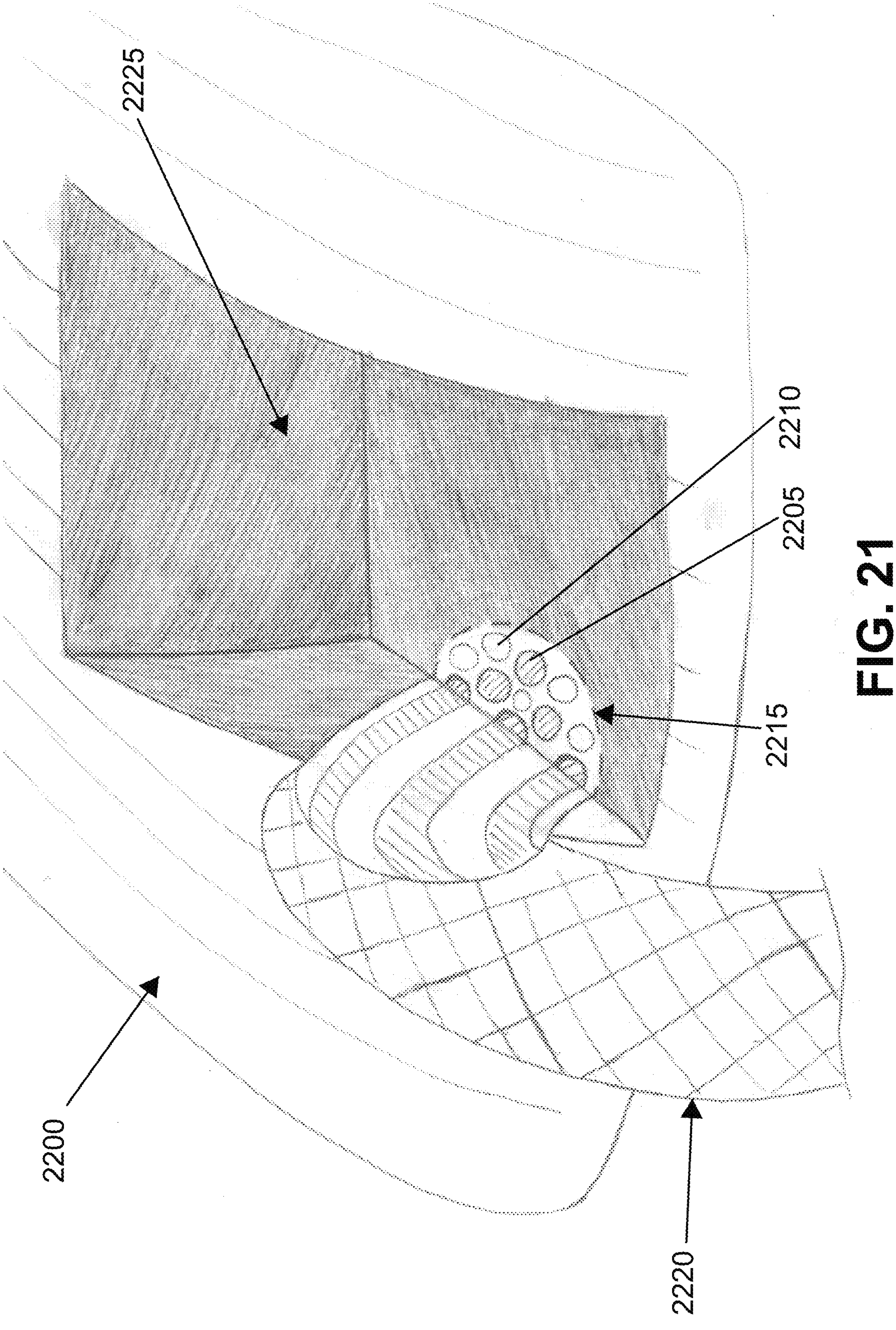
FIG. 21 is a schematic cutaway cross-sectional view of a collagen-UHMWPE co-braid at implantation.
Figure 22:
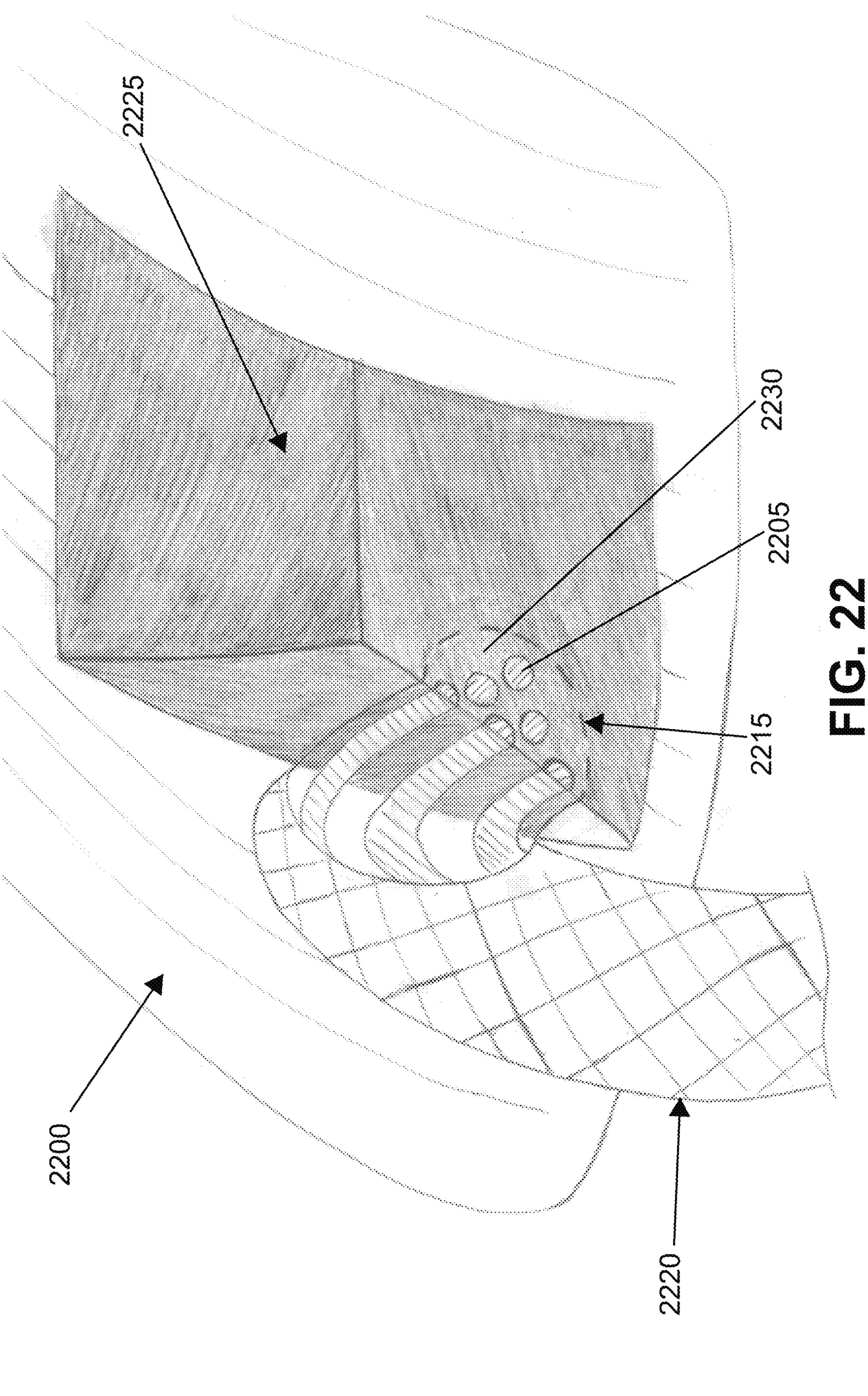
FIG. 22 is a schematic cutaway cross-sectional view of a collagen-UHMWPE co-braid 8 to 16 weeks following implantation.

As mentioned above, with time following implantation, the collagen fibers are resorbed and replaced with native tissue, resulting in an integration of the synthetic fibers into the tissue (e.g., ligament or tendon). Complete resorption is achieved within 8-16 weeks following implantation. Because the collagen is fully replaced with native tissue, the amount of suture material that remains implanted is minimized. FIGS. 21 and 22 illustrate cross-sections of an implanted collagen-UHMWPE co-braid suture at implantation and post collagen resorption.

FIG. 21 is a schematic cutaway cross-sectional view of a collagen-UHMWPE co-braid at implantation. As shown in FIG. 21, connective tissue (e.g., ligament or tendon) 2200 has a collagen-cobraid suture 2220 passing through it. A three-dimensional cutaway cross-sectional view is provided by removing material in a wedge-shaped area 2225. This reveals both longitudinal and lateral cross-sectional views of suture 2220.

A dashed line 2215 illustrates an approximate boundary between the fibers of suture 2220 and connective tissue 2200. Within this boundary, multiple circular fiber cross-sections are shown. The shaded circles are synthetic fibers 2205, whereas the unshaded circles are collagen fibers 2210. It will be understood that the arrangement of fibers in FIGS. 21 and 22 are schematic only with the intention being to illustrate the resorption of collagen fibers conceptually. That is, the concept of collagen resorption is independent of the fiber configuration of a collagen-UHMWPE co-braid.

FIG. 22 is a schematic cutaway cross-sectional view of a collagen-UHMWPE co-braid 8 to 16 weeks following implantation. As shown in FIG. 22, dashed line 2215 has been included again for reference. As further shown, the area 2230 within dashed line 2215 and surrounding the synthetic fibers 2205 is now filled with native tissue, shown with different shading than the synthetic fibers.

Accordingly, the collagen fibers of the co-braid are configured to be replaced with native tissue with time following implantation. In particular, the collagen fibers are configured to be replaced with native tissue within 8 to 16 weeks after implantation.

Figure 23:
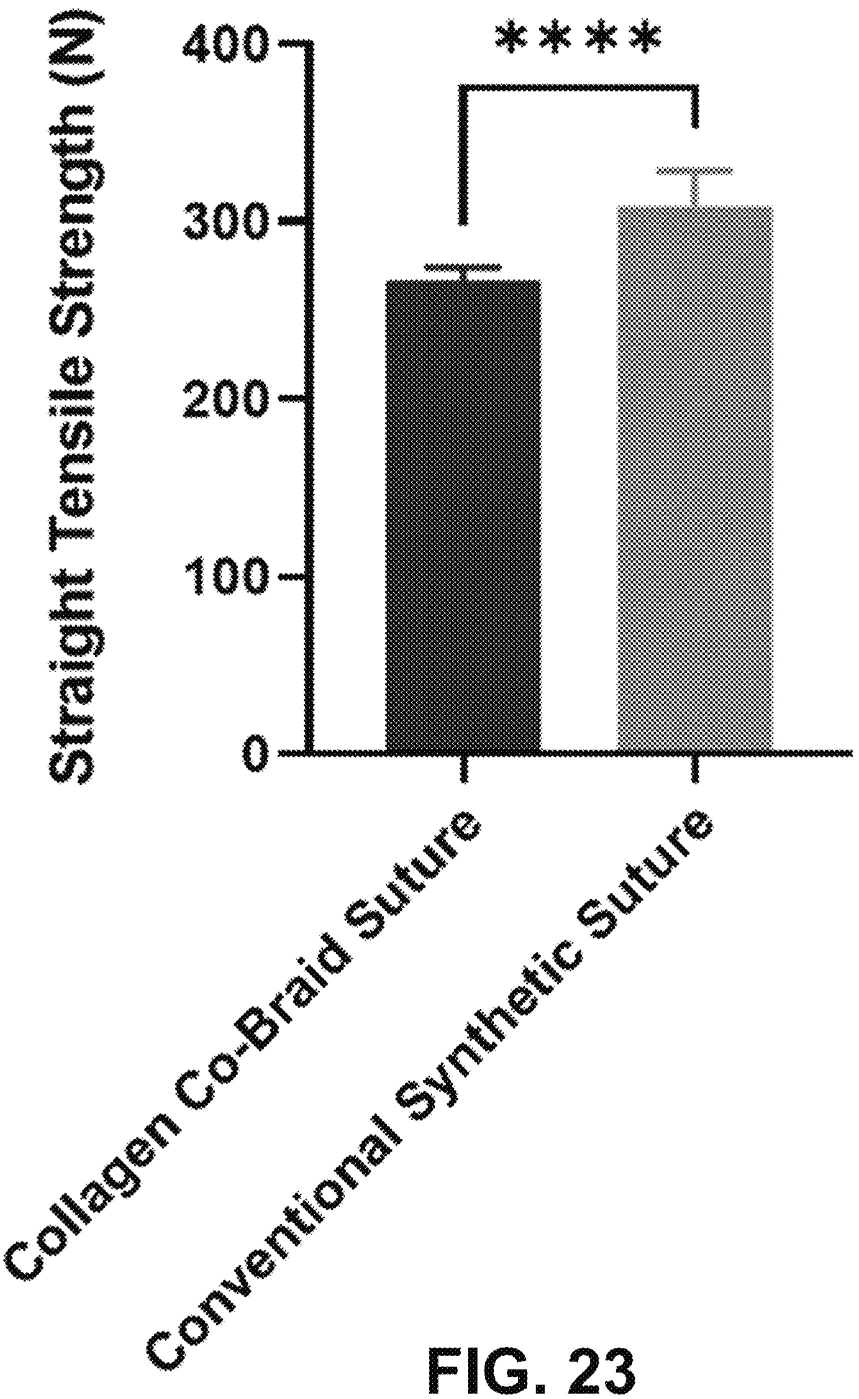
FIG. 23 is a graph illustrating the straight tensile strength of a braided #2 suture constructed in accordance with the present disclosure in comparison to a conventional fully synthetic braided #2 suture.

FIG. 23 is a graph illustrating the straight tensile strength of a braided #2 suture constructed of collagen and UHMWPE in accordance with the present disclosure in comparison with a conventional fully synthetic braided suture of the same size. As shown in FIG. 23, unexpectedly, the tensile strength of a collagen-UHMWPE suture approaches that of conventional fully synthetic braided suture of the same size, despite having approximately half as much of the synthetic material by weight (see FIG. 32). At least one factor that is believed to contribute to the unexpected strength of the collagen co-braid is that more smaller synthetic fibers are used than in conventional fully synthetic braided sutures. These smaller fibers increase the surface area of contact between fibers and may result in load sharing between fibers.

Not only does the tensile strength of the collagen co-braid approach that of conventional fully synthetic braided suture, but other mechanical parameters even more closely approximate those of the conventional suture. Additional testing results are discussed below.

The asterisks in the accompanying graphs (including FIG. 23 discussed above) indicate statistical confidence in the differences between the measured values. Where appropriate, data sets were analyzed for statistical differences in mean using unpaired parametric t tests with Welch's correction. Results are plotted showing mean with error bars representing SD and statistical significance is determined as follows: *$p<0.05$, $p<0.01$, *$p<0.001$, ****$p<0.0001$.

A significant parameter for sutures, including braided sutures, is knot tensile strength. Knots tend to reduce the strength of textile strands, like braided sutures, because the knots create an imbalance of loading on the fibers that form the strand. Since surgical sutures are knotted as part of most surgical uses, the knot strength of surgical sutures is relevant. At least one advantage/benefit of the collagen-UHMWPE co-braided sutures is a high knot tensile strength.

Figure 24:
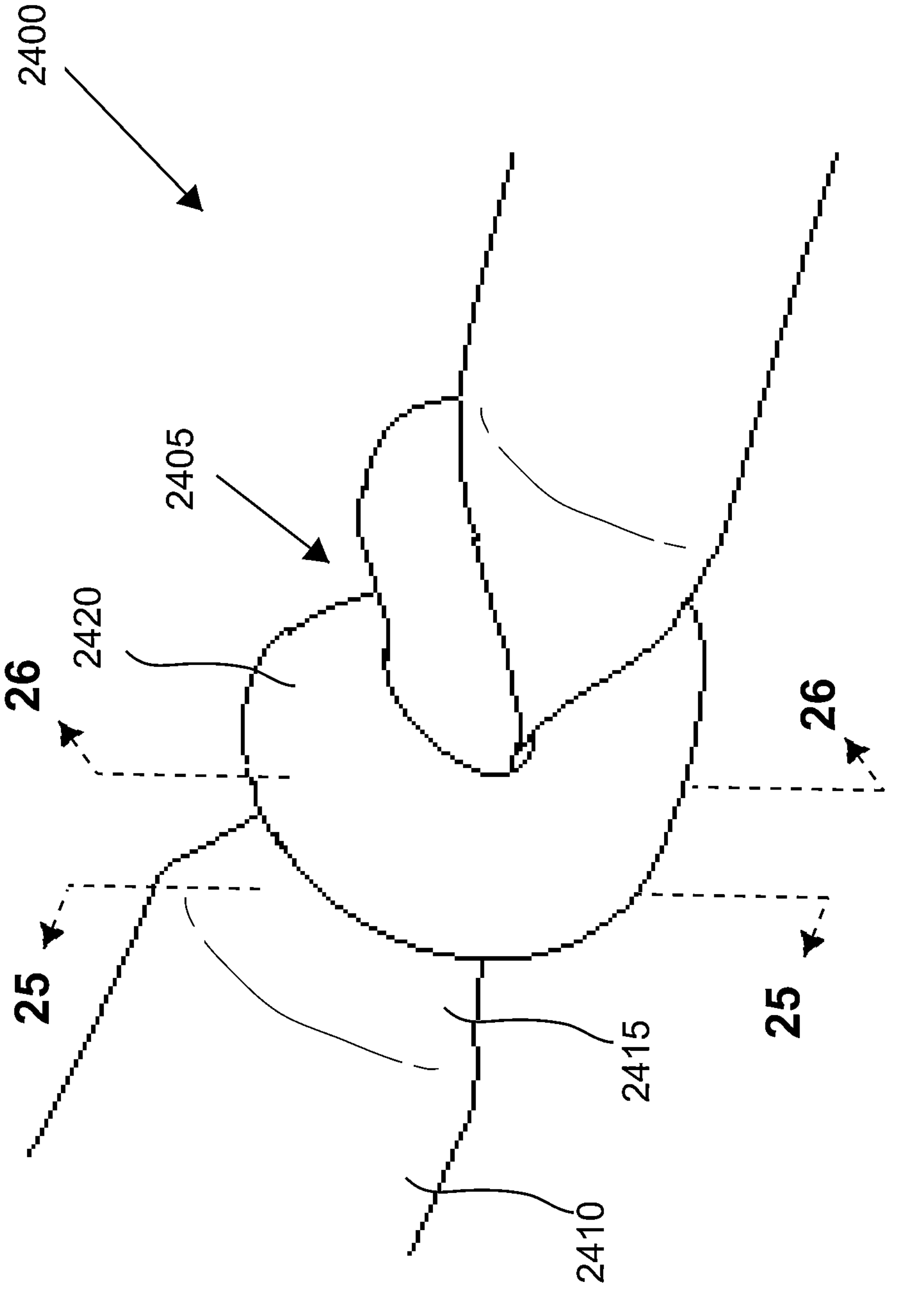
FIG. 24 is a schematic illustration of a knot tied in a braided strand having a substantially circular cross-section.
Figure 25:
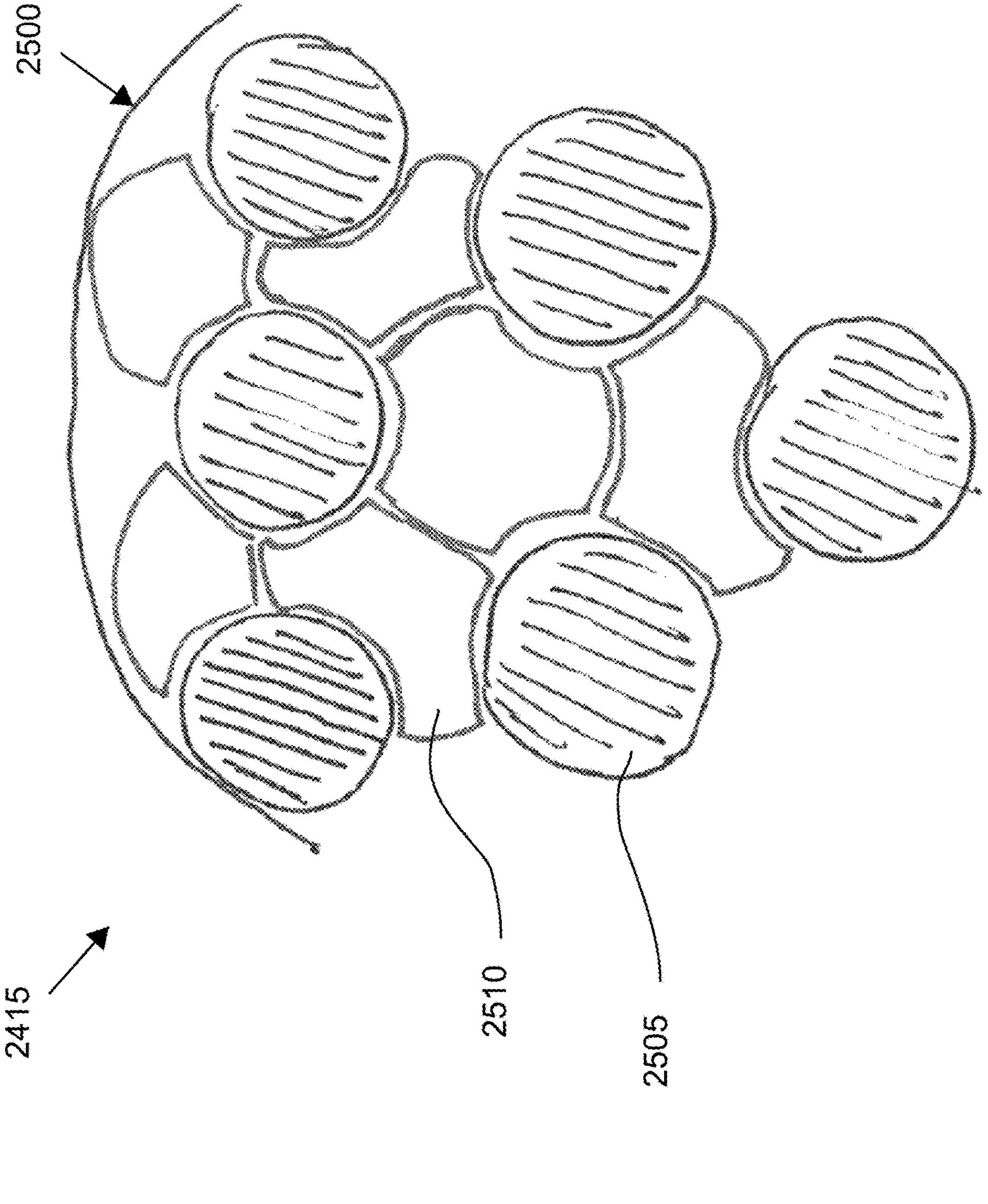
FIG. 25 is a first schematic cross-sectional view taken at line 25-25 in FIG. 24.
Figure 26:
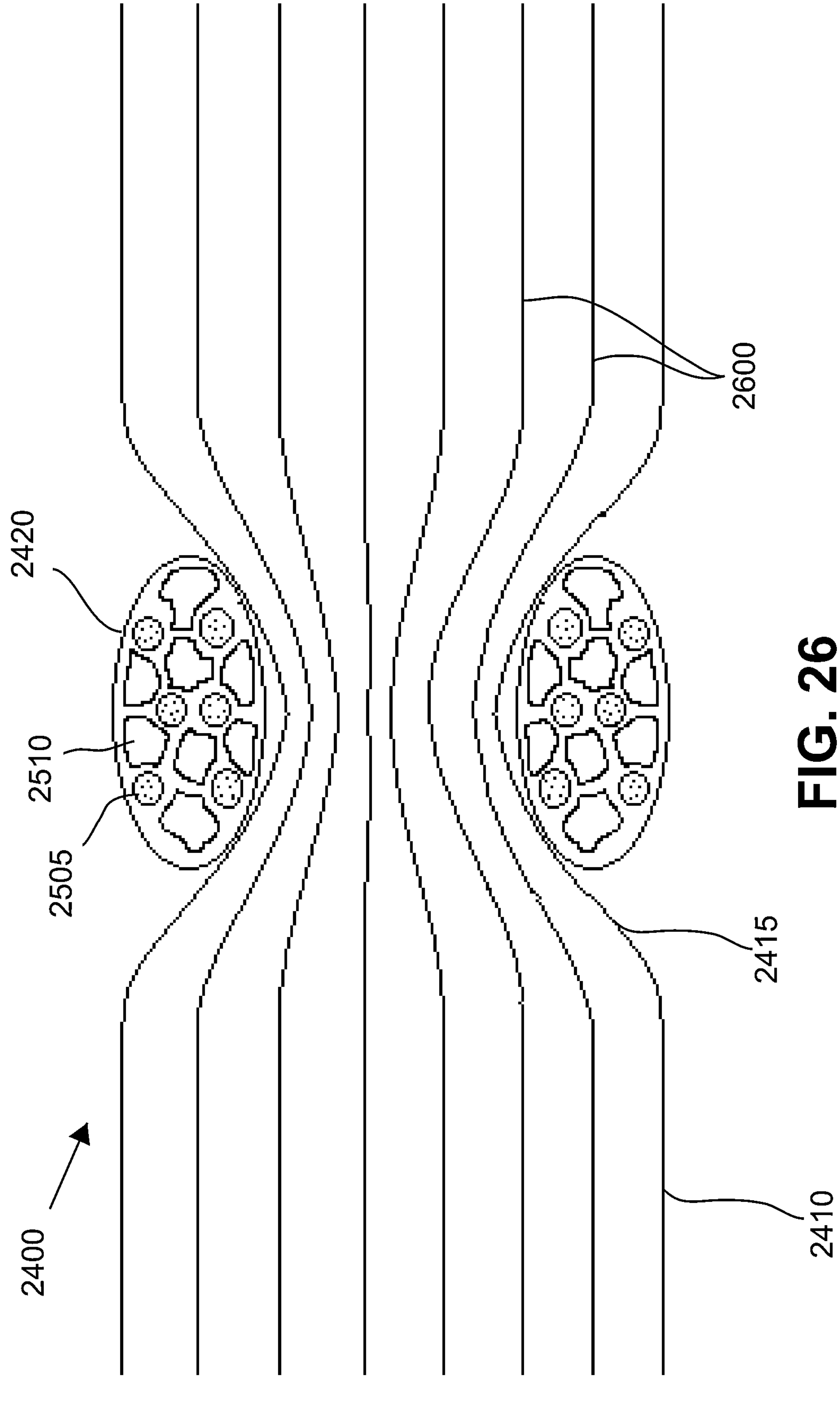
FIG. 26 is a second schematic cross-sectional view taken at line 26-26 in FIG. 24.

FIGS. 24-26 illustrate at least one mechanism that may contribute to improved knot strength of collagen-UHMWPE co-braided sutures. FIG. 24 is a schematic illustration of a knot tied in a braided suture, where the braided suture has a substantially circular cross-section. As shown, a braided suture 2400 includes a knot 2405 tied in it. It will be understood that knot 2405 is schematic only and intended to be generic. Those of ordinary skill in the art will understand that various types of knots may be used for surgical sutures. Most knots will reduce the tensile strength of the braided suture to some extent. The construction of the collagen-UHMWPE co-braid improves knot tensile strength generally, and thus, will provide a high knot tensile strength for most, or possibly all, knots used in surgical suturing.

The collagen fibers are generally more deformable than the synthetic UHMWPE fibers. Accordingly, when tied in a knot, the collagen fibers deform, and thereby conform to the surrounding UHMWPE fibers. In doing so, the collagen fibers fill the interstitial spaces between the UHMWPE fibers resulting in a greater surface area of contact between the collagen fibers and the synthetic fibers. The binding between fibers creates additional friction forces between the collagen fibers and the UHMWPE fibers, essentially providing for longitudinal load sharing between the fibers, thereby evening out the imbalance in fiber loading that is otherwise created by the knot.

In some embodiments, the collagen fibers of a knotted collagen-UHMWPE co-braid may deform to an irregular cross-section, yet retain their overall cross-sectional area. In other embodiments, the collagen fibers may compress radially, and thus deform to a geometry with not only an irregular cross-section but also reduced cross-sectional area.

As shown in FIG. 24, knot 2405 includes a knotted portion 2420 where the suture is wrapped around itself. As further shown in FIG. 24, knot 2405 compresses braided suture 2400. For example, while braided suture 2400 has an uncompressed region 2410 having a first, uncompressed diameter, braided suture 2400 has a compressed region 2415 in and around the knot, the compressed region having a second, compressed diameter that is smaller than the uncompressed diameter.

FIG. 25 is a first schematic cross-sectional view taken at line 25-25 in FIG. 24. FIG. 25 is a truncated view showing a wedge-shaped portion of braided suture 2400 taken through compressed region 2415. An outer surface 2500 of the braided suture is shown schematically with a truncated curved line. The UHMWPE fibers 2505 are shown with shading. The collagen fibers 2510 are shown without shading. As shown in FIG. 25, although the collagen fibers 2510 originate with a substantially circular cross-sectional shape, they may deform, thereby conforming to the relatively (comparatively) non-deformable UHMWPE fibers. Thus, in FIG. 25, collagen fibers 2510 are shown having irregular cross-sectional shapes, conforming to the surrounding UHMWPE fibers and filling in the interstitial spaces. It will be understood that, although small spaces are shown between the collagen fibers and the synthetic fibers, this is only for purposes of illustration, with the intention being to show the fibers in contact with one another, filling in almost all of the interstitial spaces. It will also be understood that FIG. 25 is schematic only and that the deformation of the collagen fibers may occur in various ways and to various degrees. For example, the extent to which the cross-sections of the collagen fibers deviate from a circular shape may be considerably less than that shown in FIG. 25, which exaggerates the effect for purposes of illustration.

FIG. 26 is a second schematic cross-sectional view taken at line 26-26 in FIG. 24. The cross-section of FIG. 26 is taken at 90 degrees with respect to that of FIG. 25. In FIG. 26, the portion of the knot that wraps around the long aspect of the braided suture is shown in cross-section, illustrating the deformation of collagen fibers 2510. It will be understood that the configuration of the knot outline in FIG. 26 is schematic in nature and would likely be asymmetrical in reality. Those of ordinary skill in the art will readily recognize that, schematically, FIG. 26 illustrates the deformation of the collagen fibers. FIG. 26 also shows the overall compression of the braided suture 2400 with curved lines 2600 schematically illustrating the compression of the strands passing through the knot. It will be understood that not all of the strands will compress the same amount, with the UHMWPE strands deforming very little, if at all.

Figure 27:
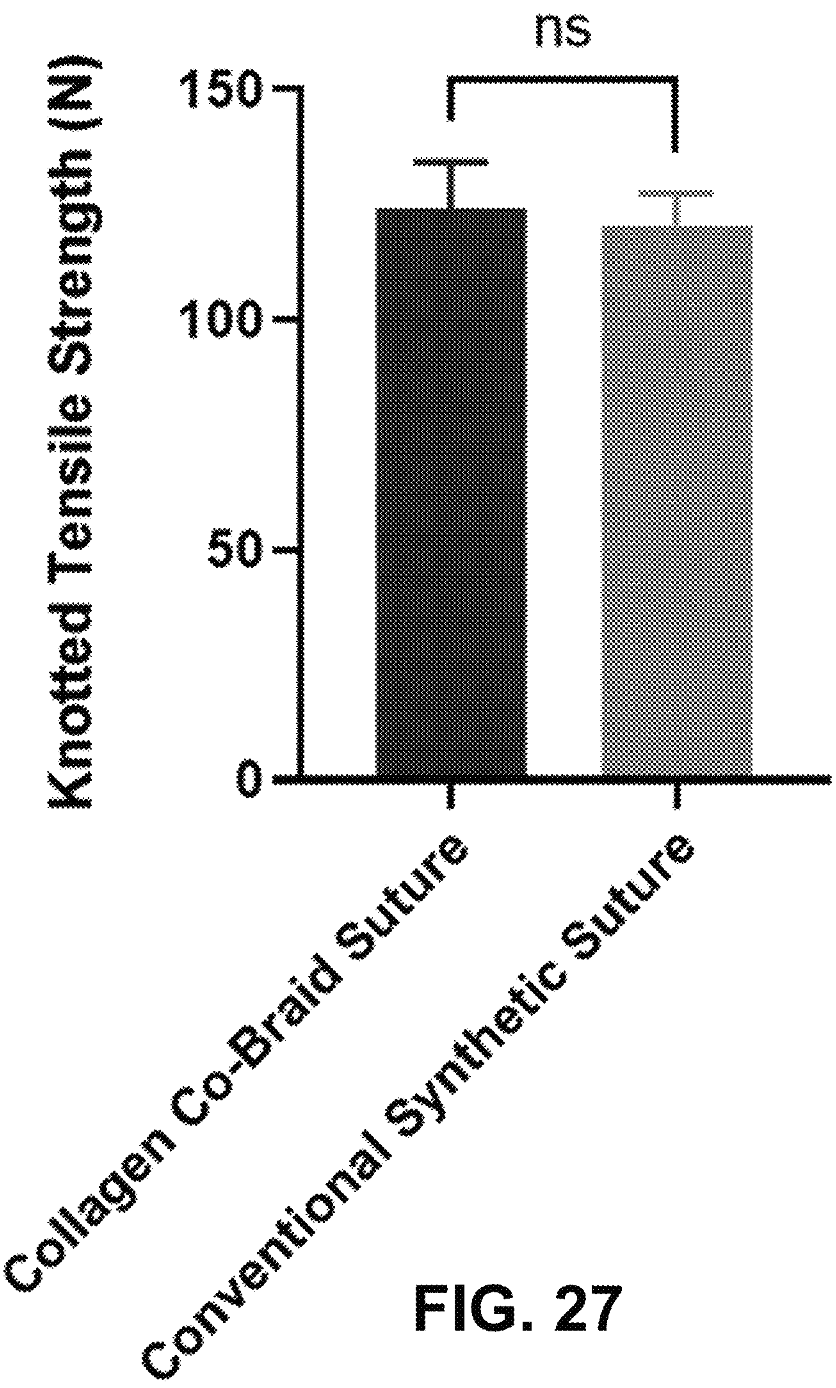
FIG. 27 is a graph showing knot tensile strength of a braided #2 suture formed in accordance with the present disclosure in comparison to a conventional fully synthetic braided #2 suture.

FIG. 27 is a graph showing knot tensile strength of a braided #2 suture formed in accordance with the present disclosure in comparison to a conventional fully synthetic suture of the same size. The measured knot tensile strength of this suture approximates that of a conventional fully synthetic braided suture of the same size, with no statistical difference between the co-braid and the synthetic suture.

Figure 28:
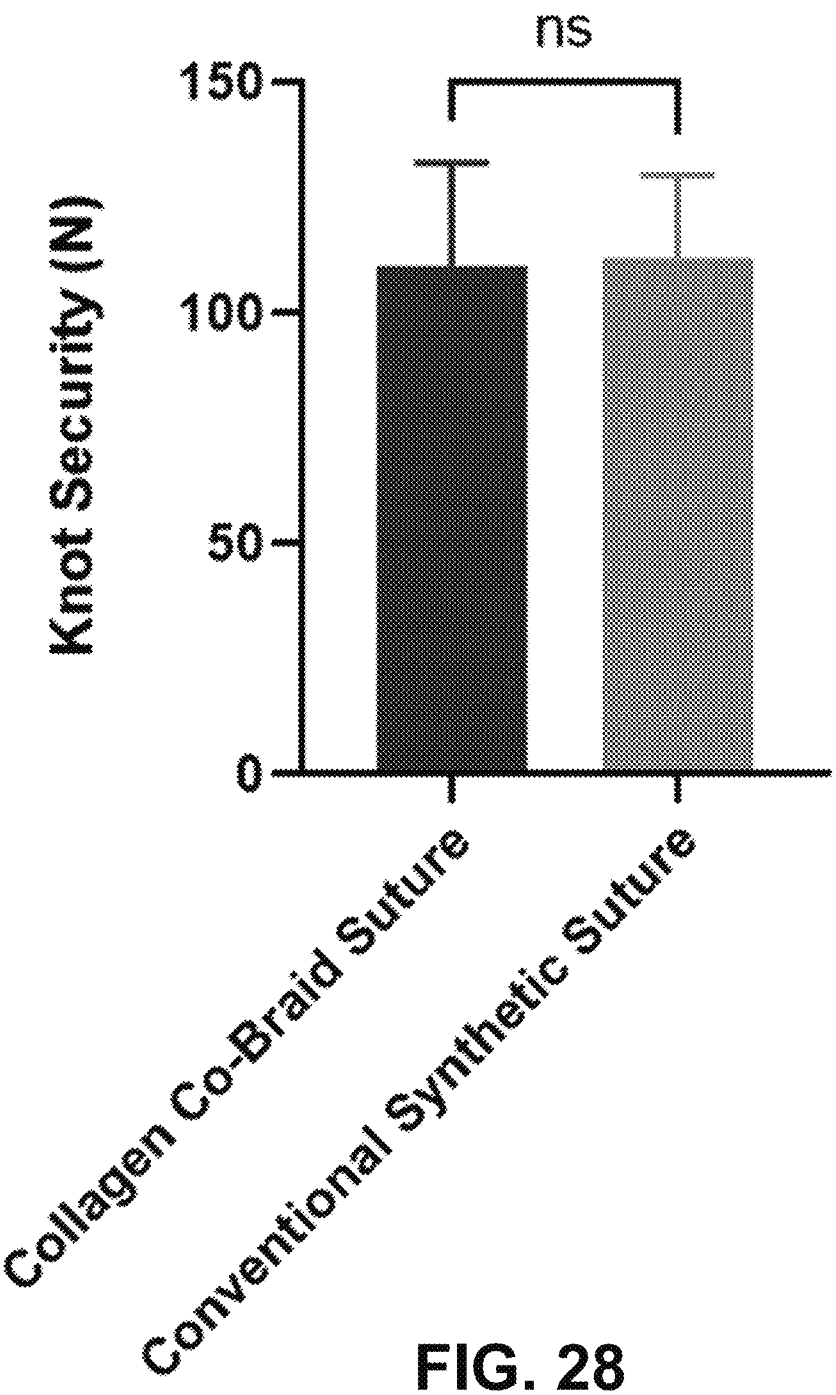
FIG. 28 is a graph showing knot security of a braided #2 suture formed in accordance with the present disclosure in comparison to a conventional fully synthetic braided #2 suture.

In addition to bolstering knot tensile strength, the deformability of the collagen fibers discussed above also contributes to resistance to knot slippage, which is an element of knot security. FIG. 28 is a graph showing knot security of a braided #2 suture formed in accordance with the present disclosure in comparison to a conventional fully synthetic braided #2 suture. As shown in FIG. 28, there was no statistical difference between the knot security of the collagen co-braid and the fully synthetic suture.

Knot profile is a parameter that evaluates the size of the knot when tied. This is a significant factor for surgical sutures because typically multiple knots are stacked on top of one another, creating a bulky mass of suture material. This mass can lead to irritation and/or damage to surrounding tissue. It has been found that the collagen-UHMWPE co-braid has a smaller knot profile than conventional fully synthetic braided suture of the same size. This provides less irritation and/or damage to surrounding tissue.

Figure 29:
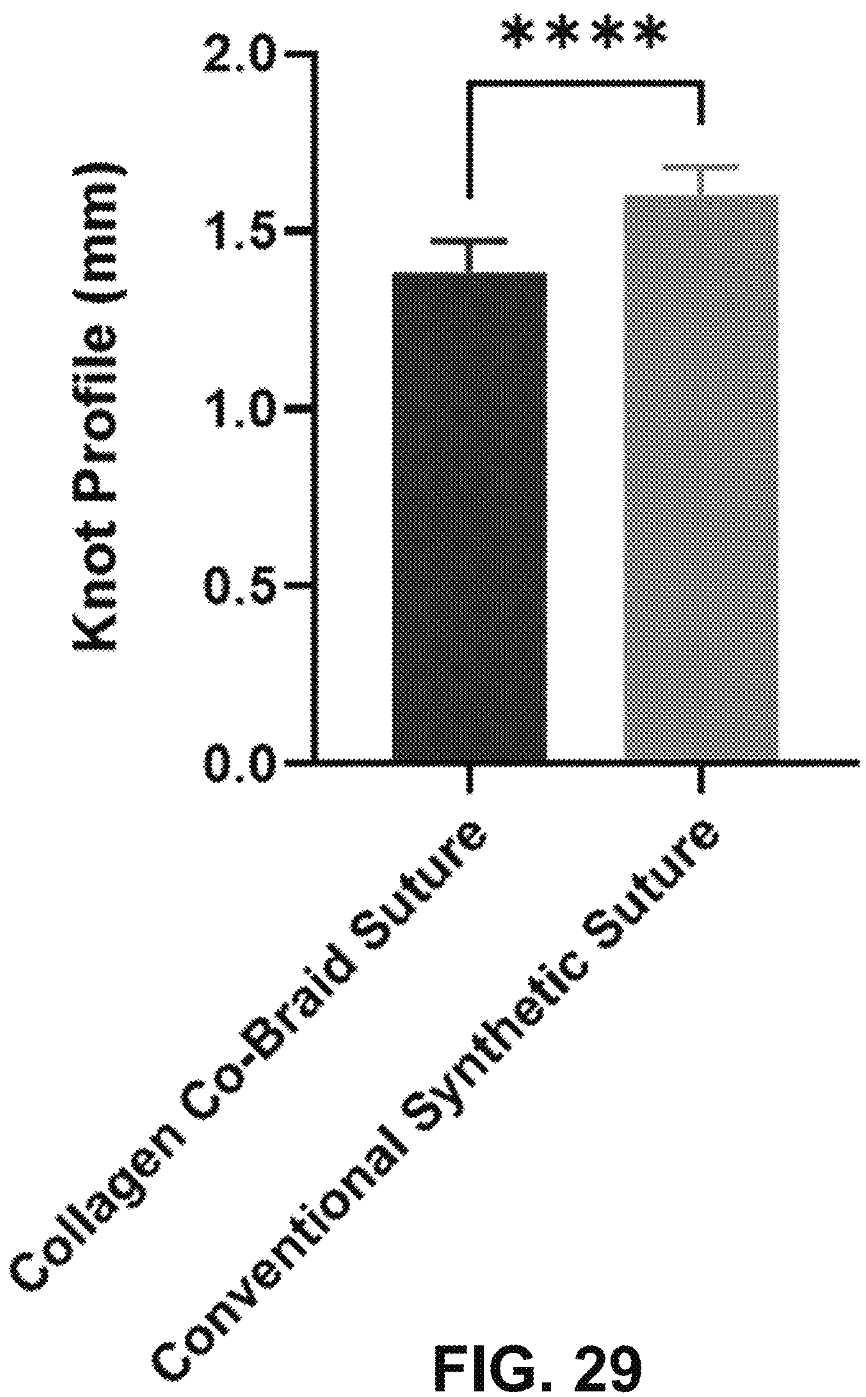
FIG. 29 is a graph showing the knot profile of a braided #2 suture formed in accordance with the present disclosure in comparison to a conventional fully synthetic braided #2 suture.

FIG. 29 is a graph showing the knot profile of a braided #2 suture formed in accordance with the present disclosure in comparison to a conventional fully synthetic braided suture of the same size. As shown in FIG. 29, the knot profile of the collagen-UHMWPE co-braid was tested to be smaller than conventional fully synthetic braided suture of the same size.

Another relevant property of sutures is abrasiveness to tissue. The collagen-UHMWPE co-braid is considerably less abrasive to tissue than conventional fully synthetic braided suture.

Figure 30:
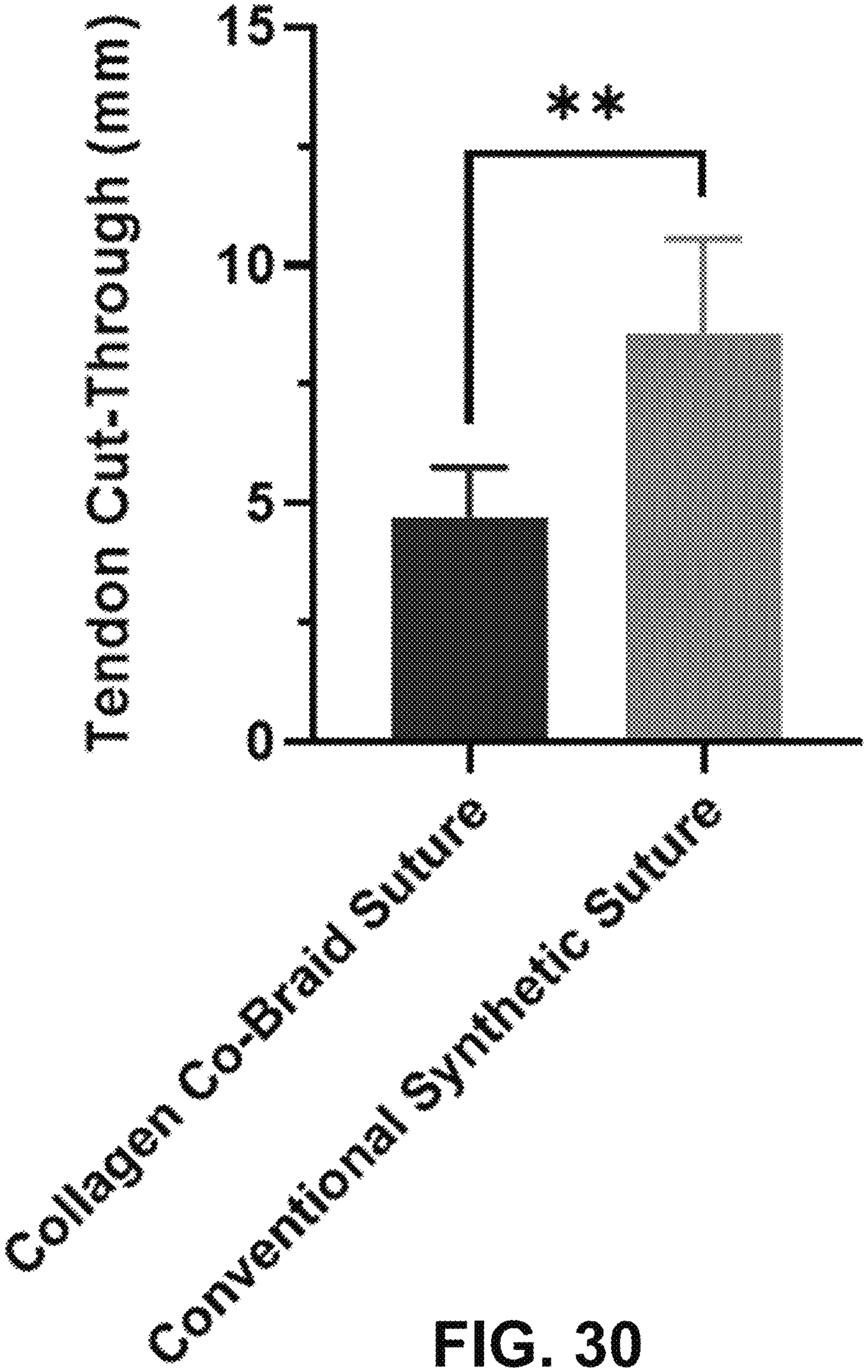
FIG. 30 is a graph showing the abrasiveness to tissue (a.k.a. tendon cut-through) for a #2 braided suture constructed in accordance with the present disclosure in comparison to a conventional fully synthetic braided #2 suture.

FIG. 30 is a graph showing the abrasiveness (a.k.a. tendon cut-through) to tissue for a #2 braided suture constructed in accordance with the present disclosure. It is shown to be considerably less abrasive to tissue than #2 conventional fully synthetic braided suture.

FIG. 31 is a table showing properties of four different braided sutures constructed in accordance with the present disclosure.

FIG. 32 is a table showing the composition/ratios of collagen to UHMWPE of four exemplary braided sutures constructed in accordance with the present disclosure. While size 2-0 round collagen-UHMWPE co-braided suture may have a 50/50 collagen/UHMWPE composition, other size sutures may have slightly varying compositions/ratios, as illustrated in FIG. 28.

Cell attachment is another relevant property of sutures, particularly sutures with collagen. The collagen-UHMWPE co-braided suture results in the collagen strands being resorbed and replaced with native tissue. This translates directly to the healing of connective tissues, such as ligaments and tendons. Cell attachment to the sutures greatly facilitates the replacement of collagen with native tissue, making the integration of the suture with native tissue much stronger. The collagen-UHMWPE co-braided suture has been found to be considerably better with respect to cell attachment than a conventional fully synthetic braided suture. In addition, the collagen-UHMWPE co-braided suture has also been found to be considerably better with respect to cell attachment than a conventional fully synthetic braided suture that is coated with collagen.

Figure 33:
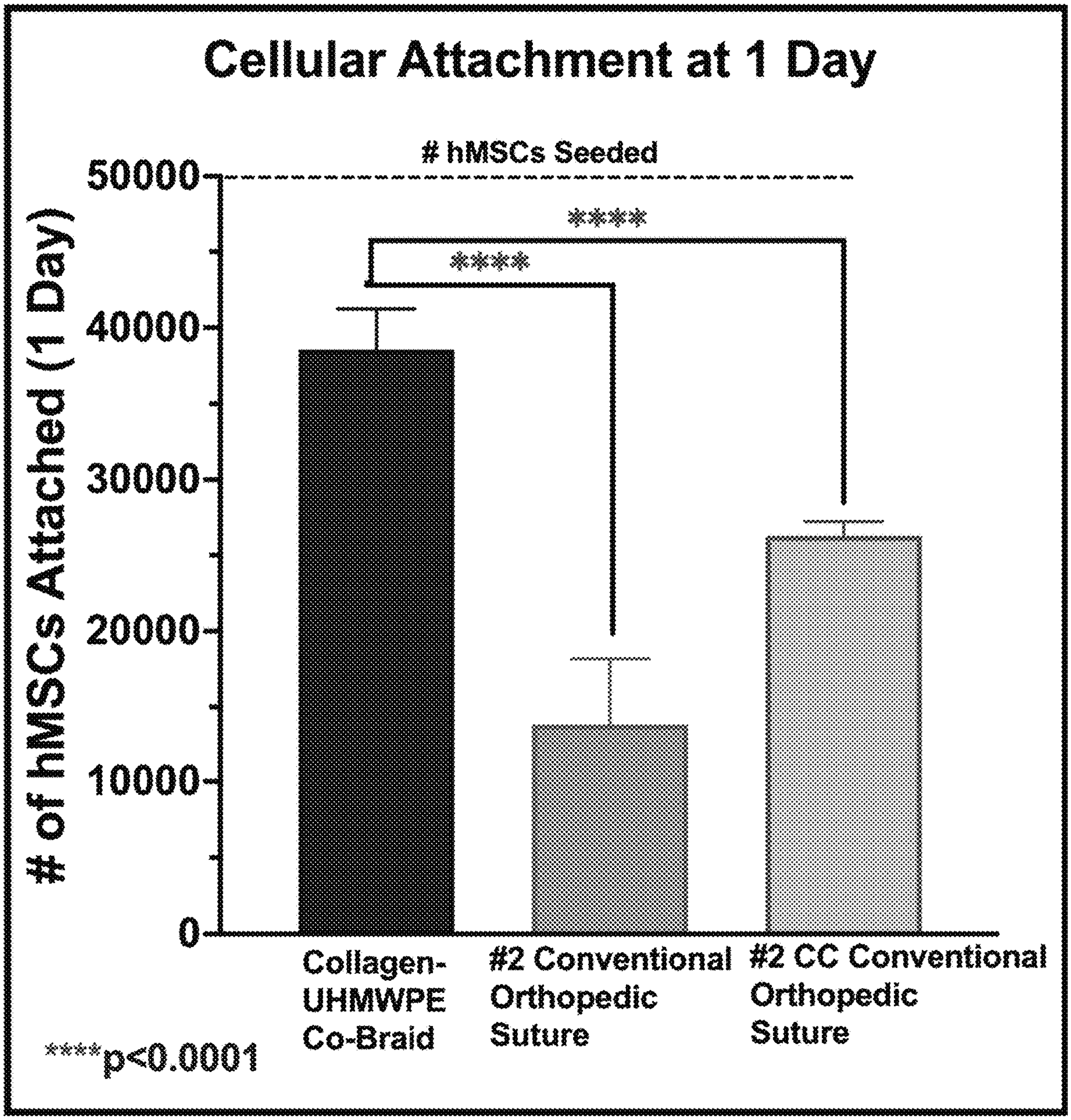
FIG. 33 is a graph illustrating cell attachment to braided suture at one day after seeding as a comparison between a collagen-UHMWPE co-braid and conventional orthopedic sutures.

FIG. 33 is a graph illustrating cell attachment to a braided suture at one day as a comparison between a collagen-UHMWPE co-braid, conventional synthetic braided suture, and collagen-coated (CC) synthetic braided suture. As shown in FIG. 33, the attachment of human mesenchymal stem cells (hMSCs) is already considerably higher on day 1 for the collagen-UHMWPE co-braid than for the conventional and collagen-coated synthetic braided sutures.

Figure 34:
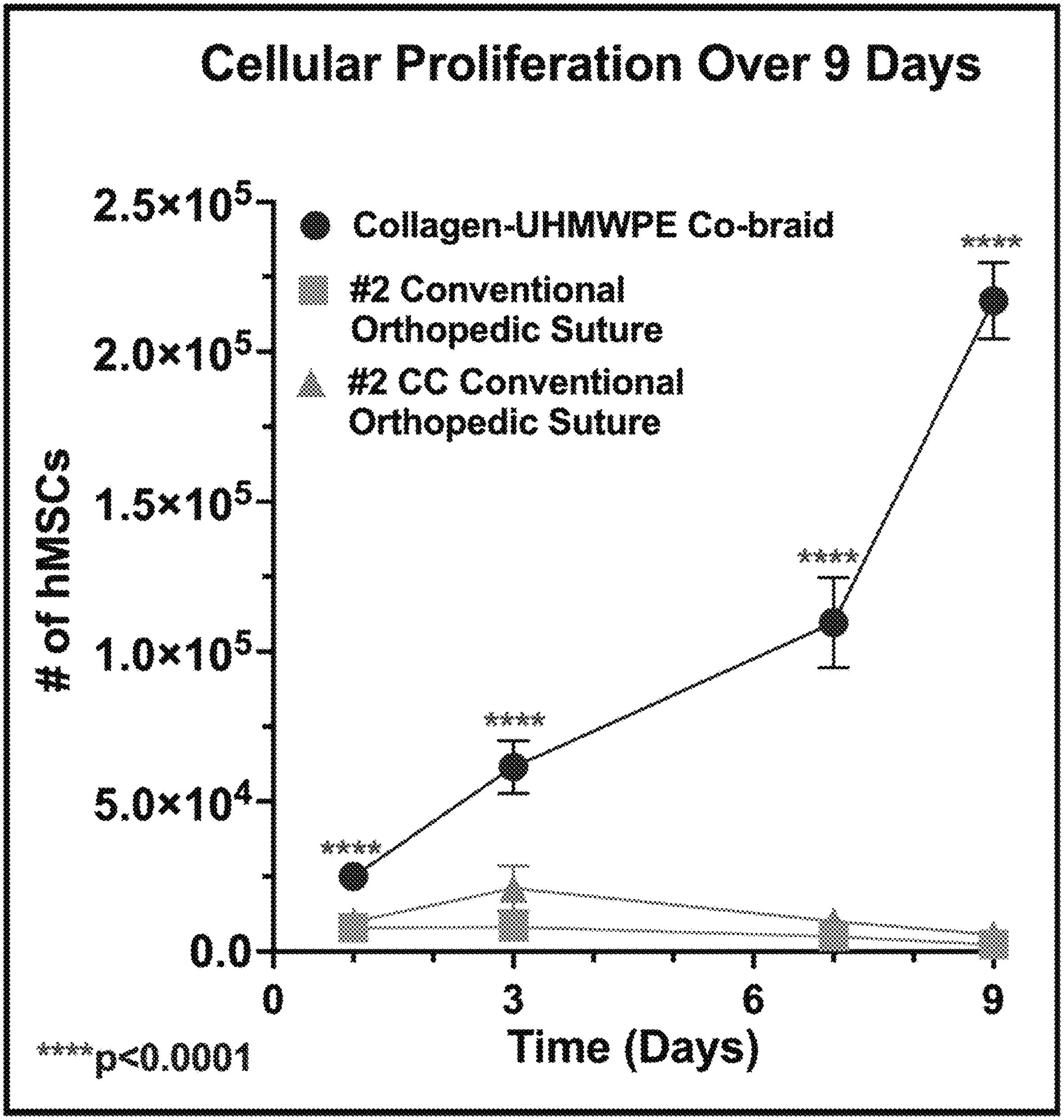
FIG. 34 is a graph illustrating cell attachment to braided suture over 9 days after seeding as a comparison between a collagen-UHMWPE co-braid and conventional orthopedic sutures.

FIG. 34 is a graph illustrating cell attachment to braided suture over 9 days after seeding as a comparison between a collagen-UHMWPE co-braid and conventional orthopedic sutures. As shown in FIG. 34, the cell attachment is even more dramatic as time passes. While the cell attachment remains minimal for the conventional synthetic braided sutures over this time period, the cell attachment to the collagen-UHMWPE co-braid continues to increase. As shown in FIG. 34, the cell attachment is non-linear for the collagen-UHMWPE co-braid. While cell attachment is generally linear over the first 7 days for the collagen-UHMWPE co-braid (albeit at a faster rate of increase than the conventional sutures), cell attachment increases dramatically over the next two days.

Figure 35:
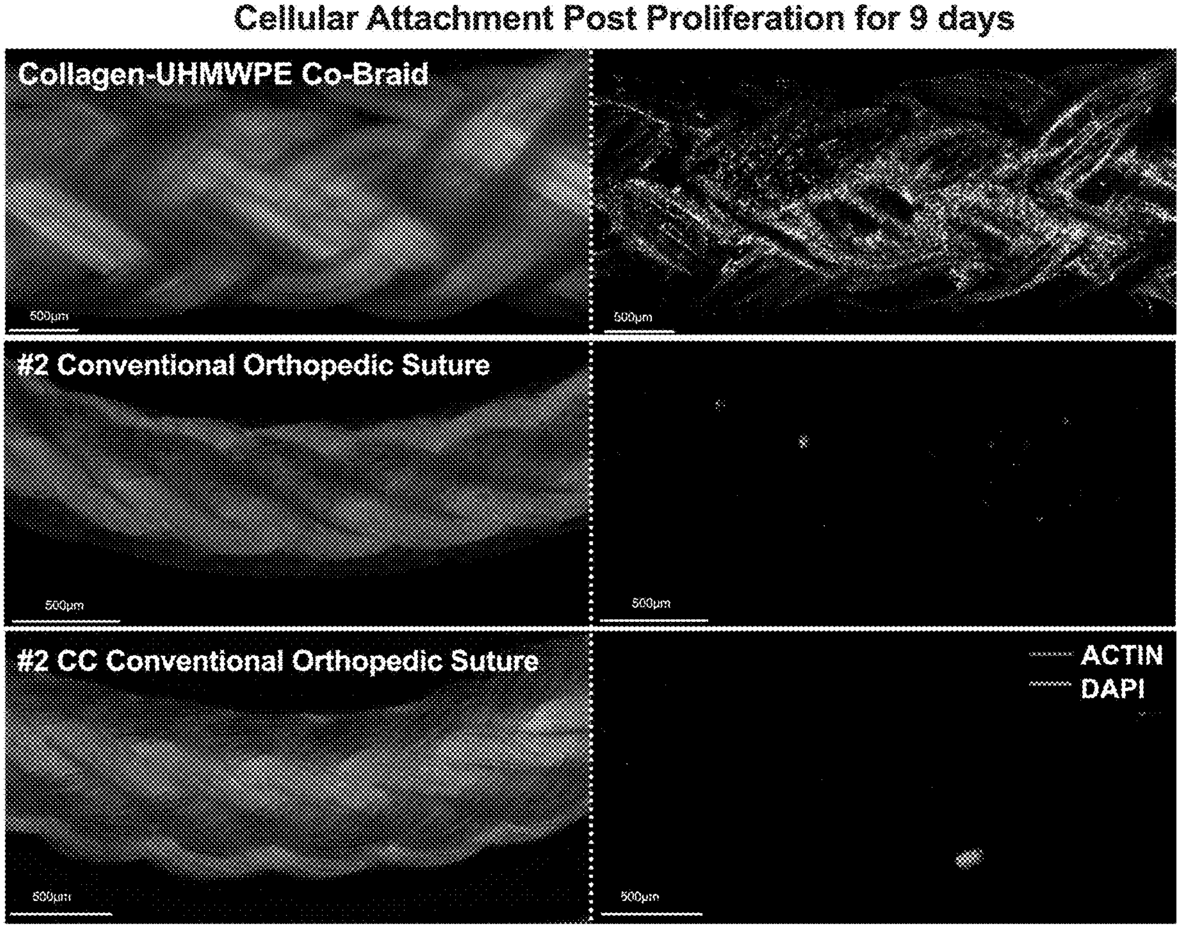
FIG. 35 shows images of a collagen-UHMWPE co-braid and conventional braided sutures showing cell attachment at 9 days after seeding.

FIG. 35 shows images of a collagen-UHMWPE co-braid and conventional sutures showing cell attachment at 9 days. The images on the left show fluorescence images of the collagen-UHMWPE co-braid, fully synthetic sutures, and collagen coated synthetic sutures, and the images on the right show the presence of attached cells. As shown, the cells are widely present on the collagen-UHMWPE co-braid and hardly present at all on the fully synthetic sutures and the collagen coated synthetic sutures.

Diameter and knot strength were measured for exemplary collagen-UHMWPE co-braided sutures of various sizes and braiding techniques.

Figure 36:
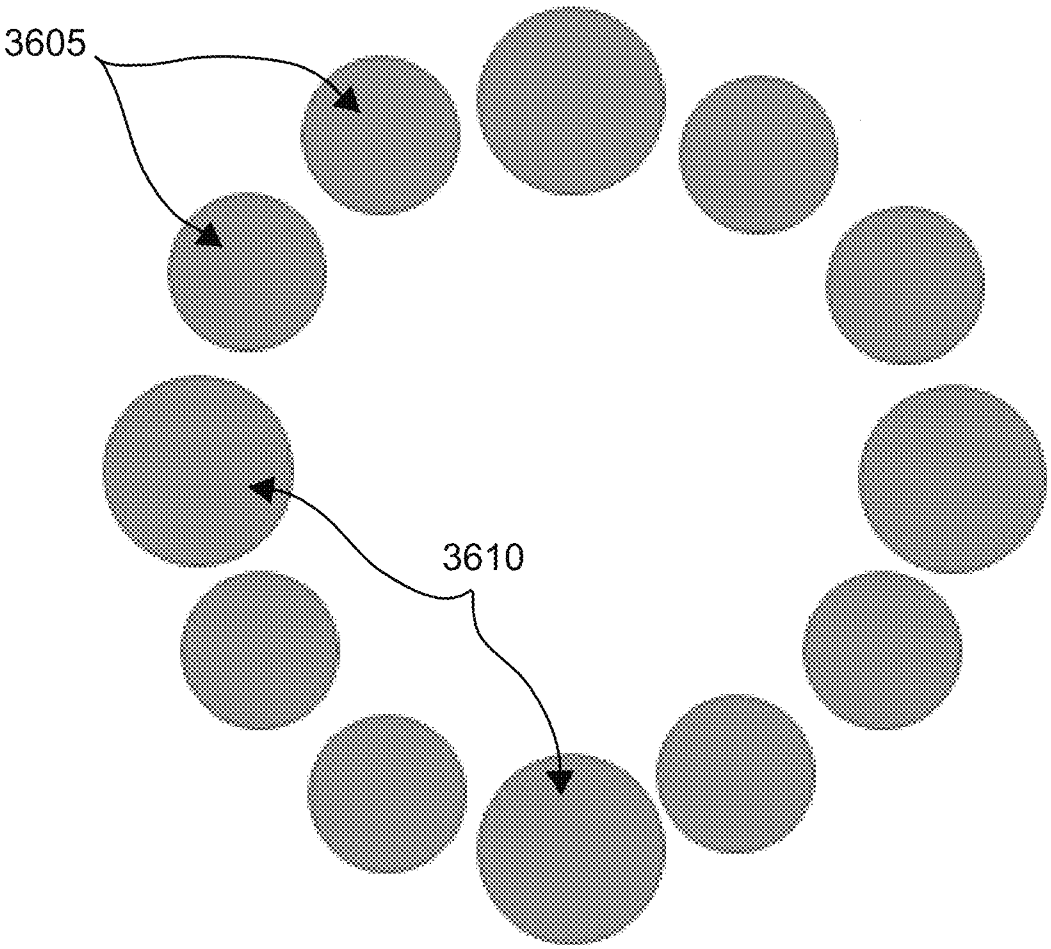
FIG. 36 is a schematic cross-sectional view of the fiber arrangement of a 2-0 suture formed of collagen-UHMWPE co-braid.

FIG. 36 is a schematic cross-sectional view of the fiber arrangement of a 2-0 suture formed of collagen-UHMWPE co-braid. It will be noted that this cross section generally illustrates the arrangement of fibers during manufacturing right before the fibers are wound about one another. The smaller diameter fibers are synthetic fibers 3605. The larger diameter fibers are collagen fibers 3610. In particular, the tested 2-0 round braid was a 12 carrier braid using 4 ends of 16FB (fiber bundle) collagen and 8 ends of 55 dTex UHMWPE fiber Notably, there is no core of fibers within the central portion of the co-braid radially inward of the outer fiber arrangement.

Testing was performed on 30 pieces produced at each PPI setting. All pieces underwent diameter testing. Only 10 pieces at each PPI setting were tested for knot tensile strength. Normality of data was checked and 10 pieces worth of data was deemed sufficient for any statistical analysis regarding knot tensile strength.

Figure 37:
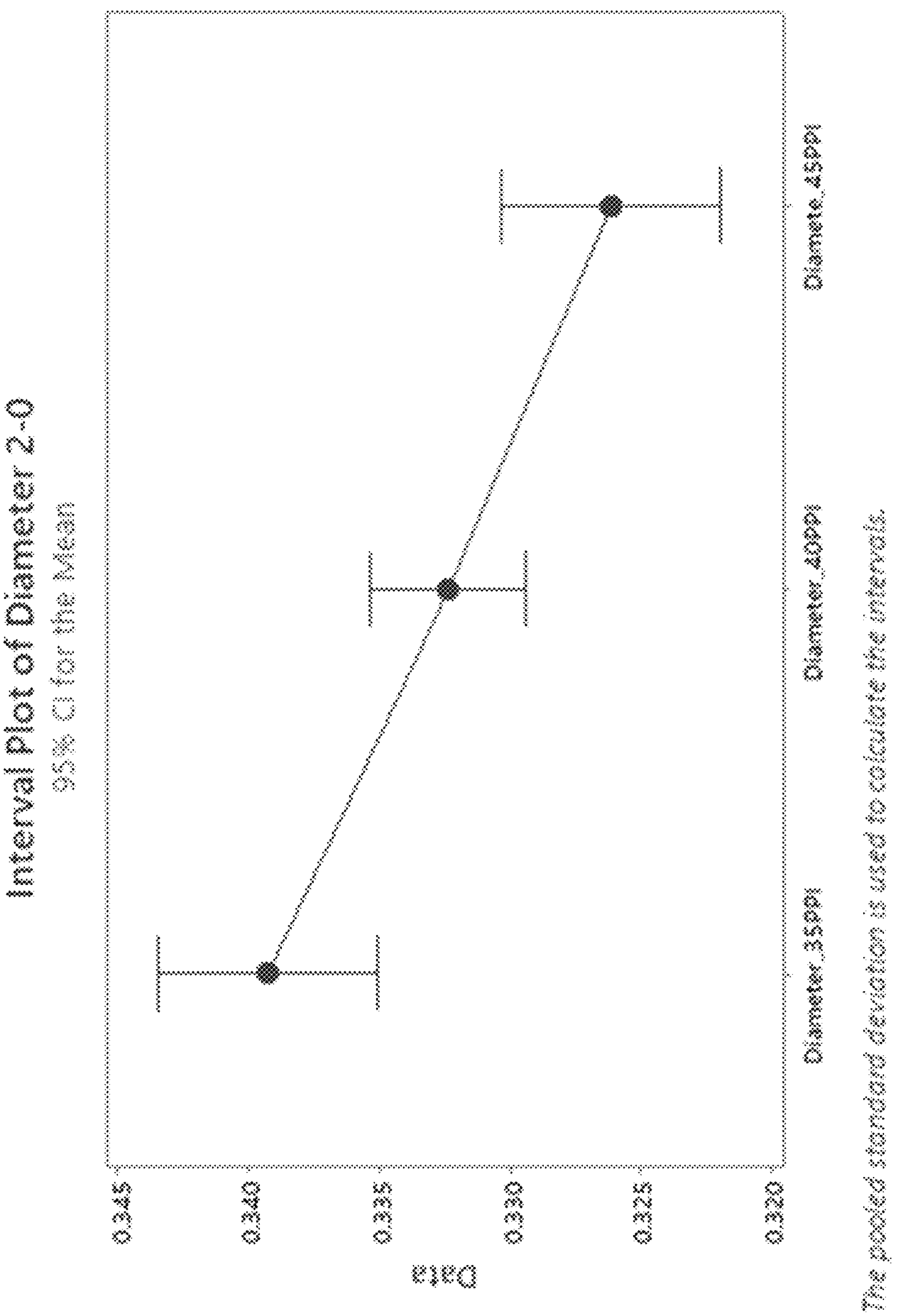
FIG. 37 is a graph showing a confidence interval plot of the diameters of a 2-0 sutures braided at different picks per inch (PPI)

FIGS. 37-44 reflect data from testing of size 2-0 round collagen-UHMWPE co-braided sutures braided at varying PPI. In particular, FIG. 37 is a graph showing a confidence interval plot of the diameters of a 2-0 sutures braided at different picks per inch (PPI).

Figure 38:
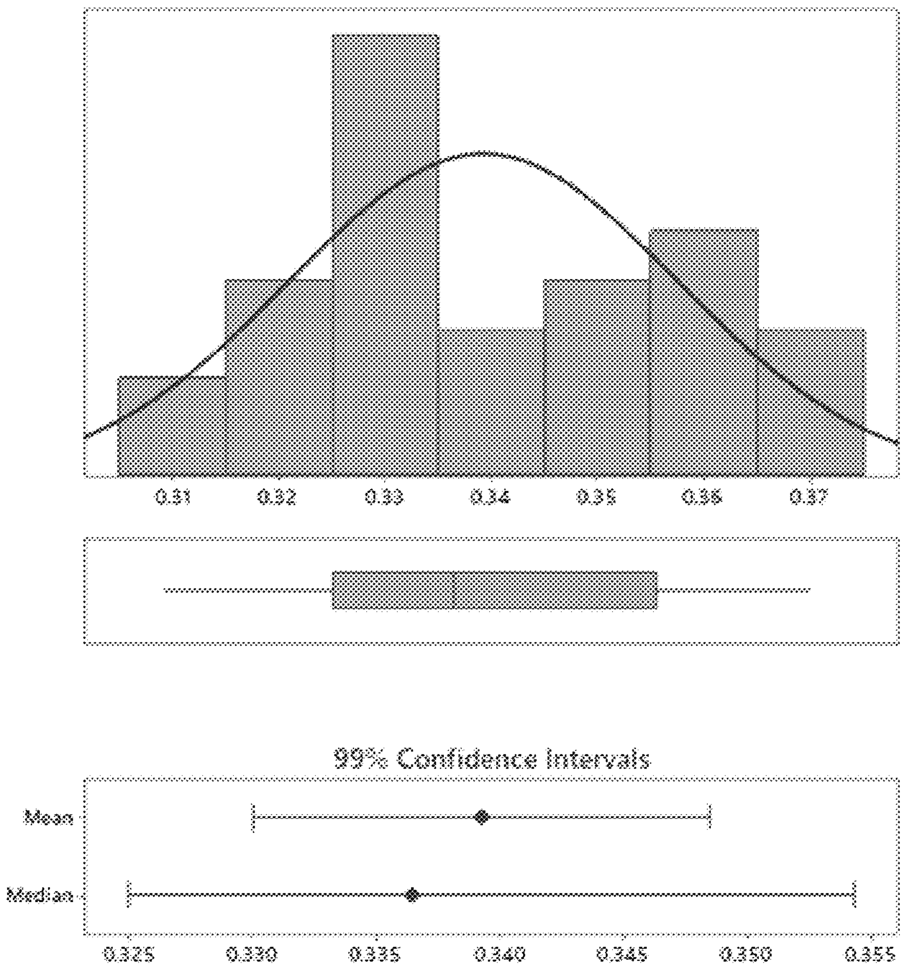
FIG. 38 is a summary report of diameter testing for a 2-0 suture braided at 35 PPI.

FIG. 38 is a summary report of diameter testing for a 2-0 suture braided at 35 PPI. The summary report indicates the results of an Anderson-Darling Normality Test for the diameter of the suture.

Figure 39:
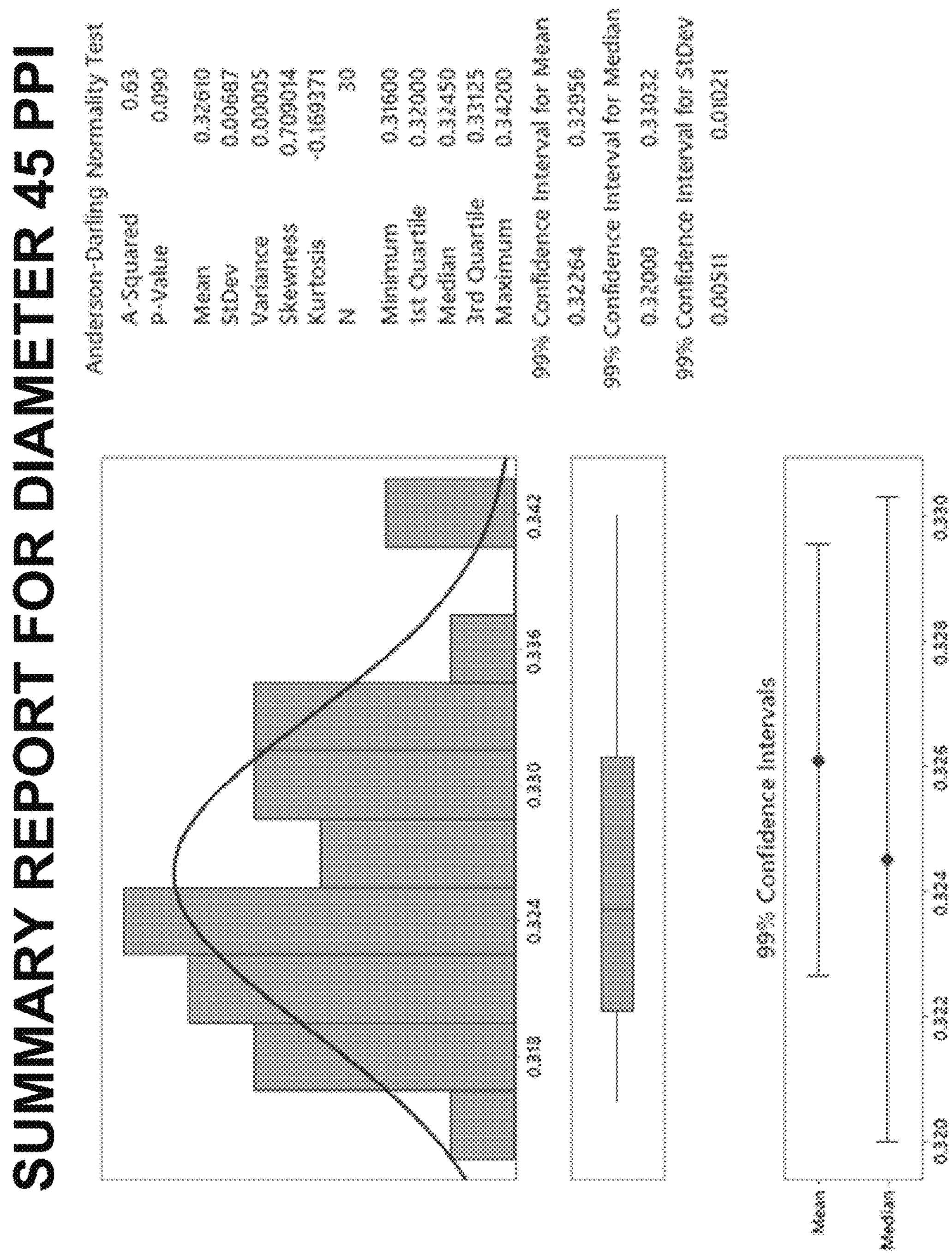
FIG. 39 is a summary report of diameter testing for a 2-0 suture braided at 45 PPI.

FIG. 39 is a summary report of diameter testing for a 2-0 suture braided at 45 PPI. The summary report indicates the results of an Anderson-Darling Normality Test for the diameter of the suture.

Figure 40:
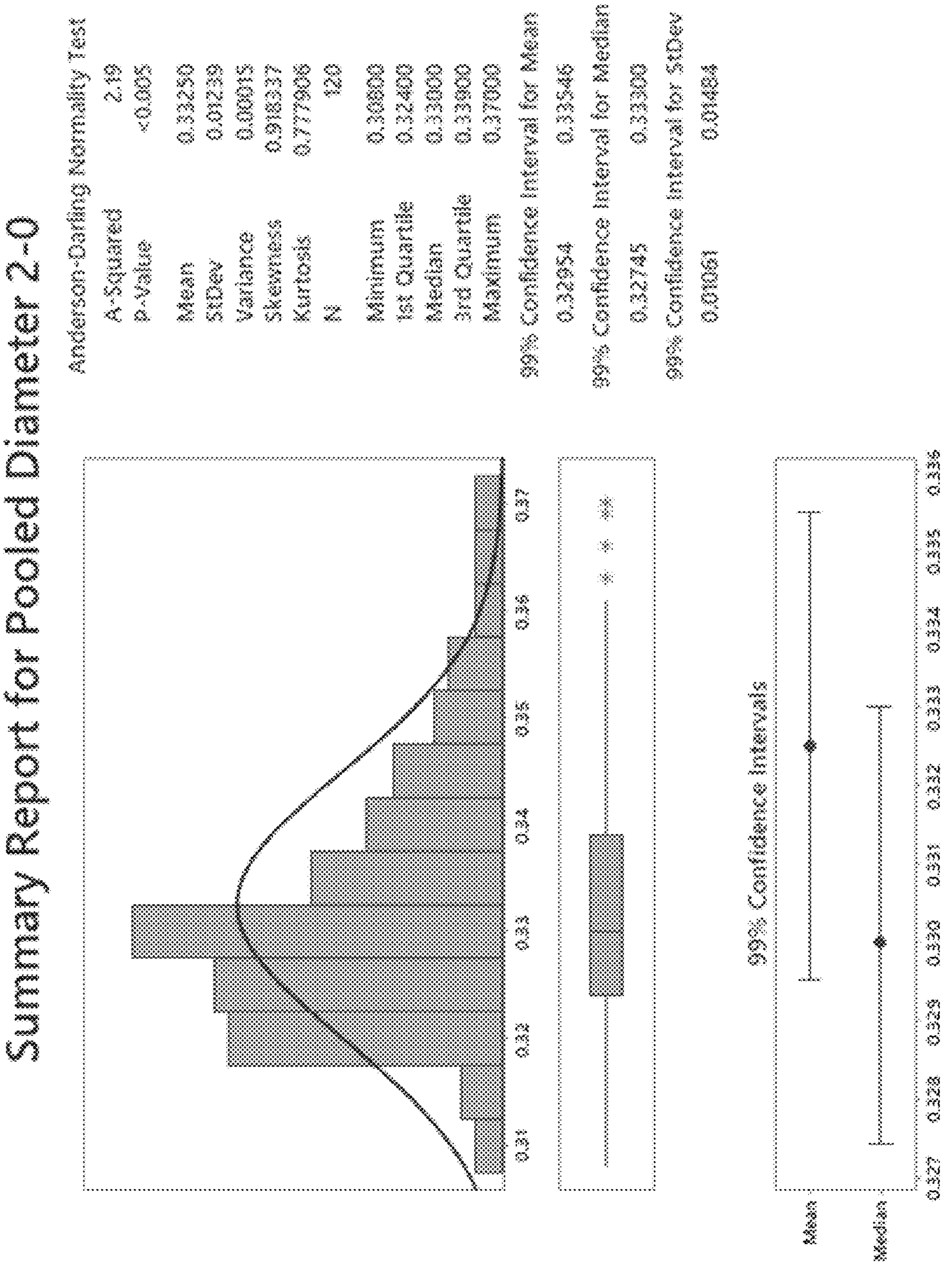
FIG. 40 is a summary report of pooled diameter for 2-0 sutures braided at various PPI.

FIG. 40 is a summary report of pooled diameter for 2-0 sutures braided at various PPI. The summary report indicates the results of an Anderson-Darling Normality Test for the diameter of the suture.

Figure 41:
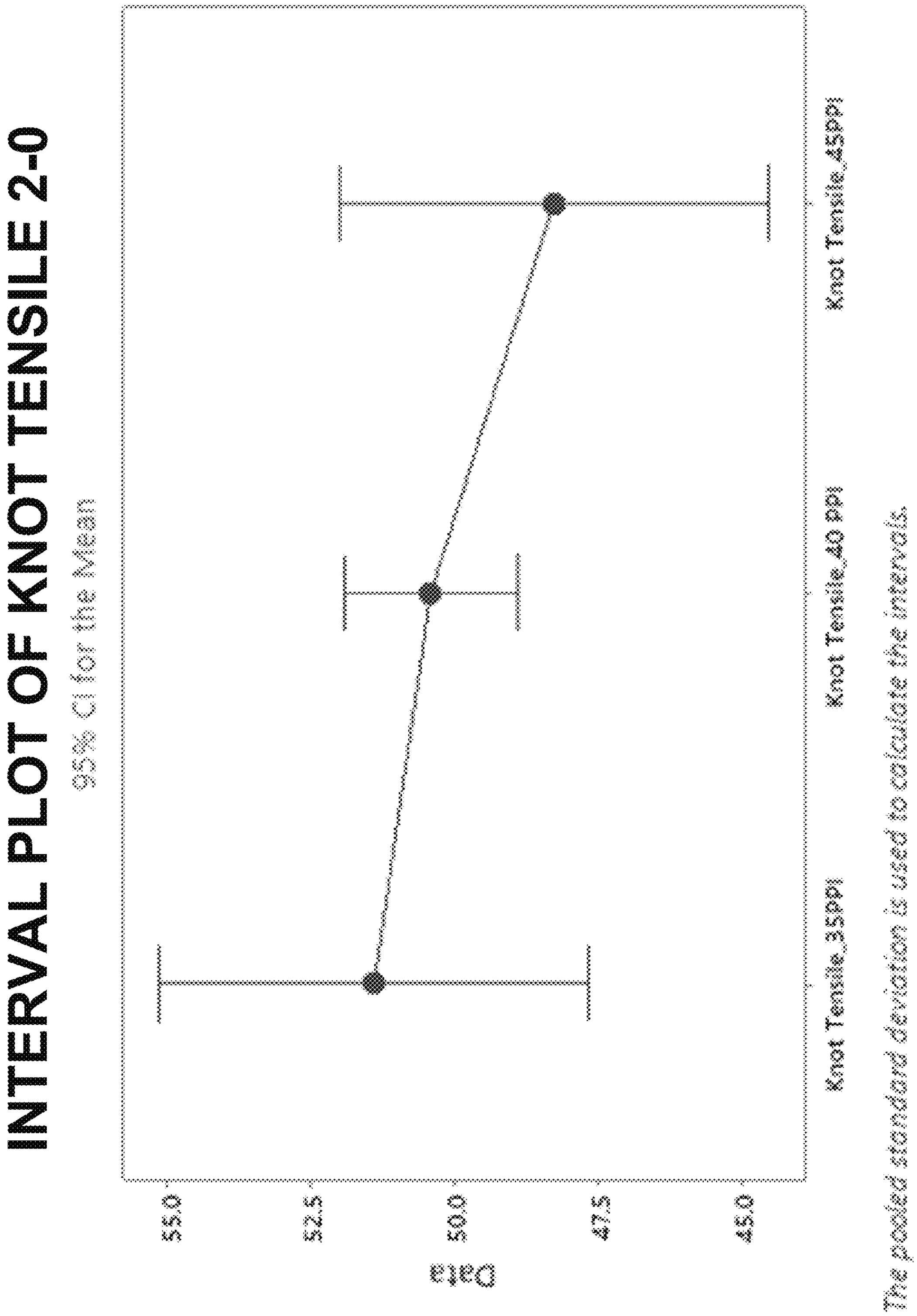
FIG. 41 is a confidence interval plot of knot tensile strength for 2-0 sutures braided at various PPI.

FIG. 41 is a confidence interval plot of knot tensile strength for 2-0 sutures braided at various PPI.

Figure 42:
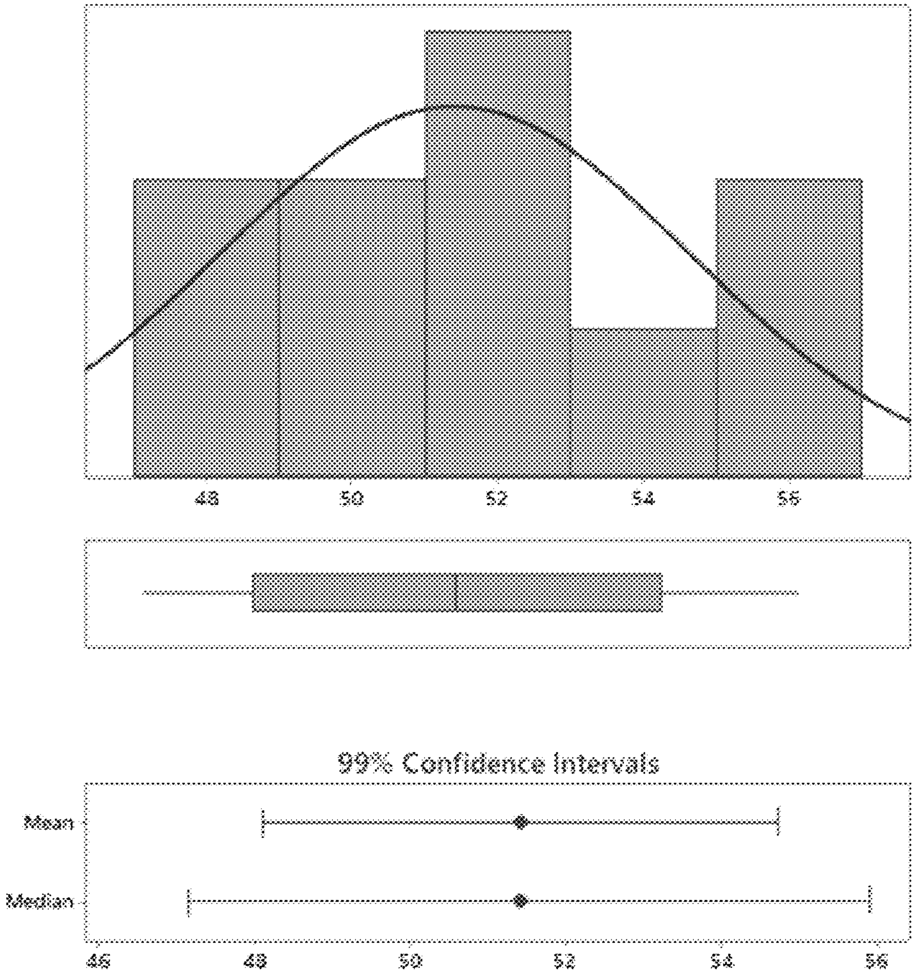
FIG. 42 is a summary report of knot tensile strength for a 2-0 suture braided at 35 PPI.

FIG. 42 is a summary report of knot tensile strength for a 2-0 suture braided at 35 PPI. The summary report indicates the results of an Anderson-Darling Normality Test for the knot tensile strength of the suture.

Figure 43:
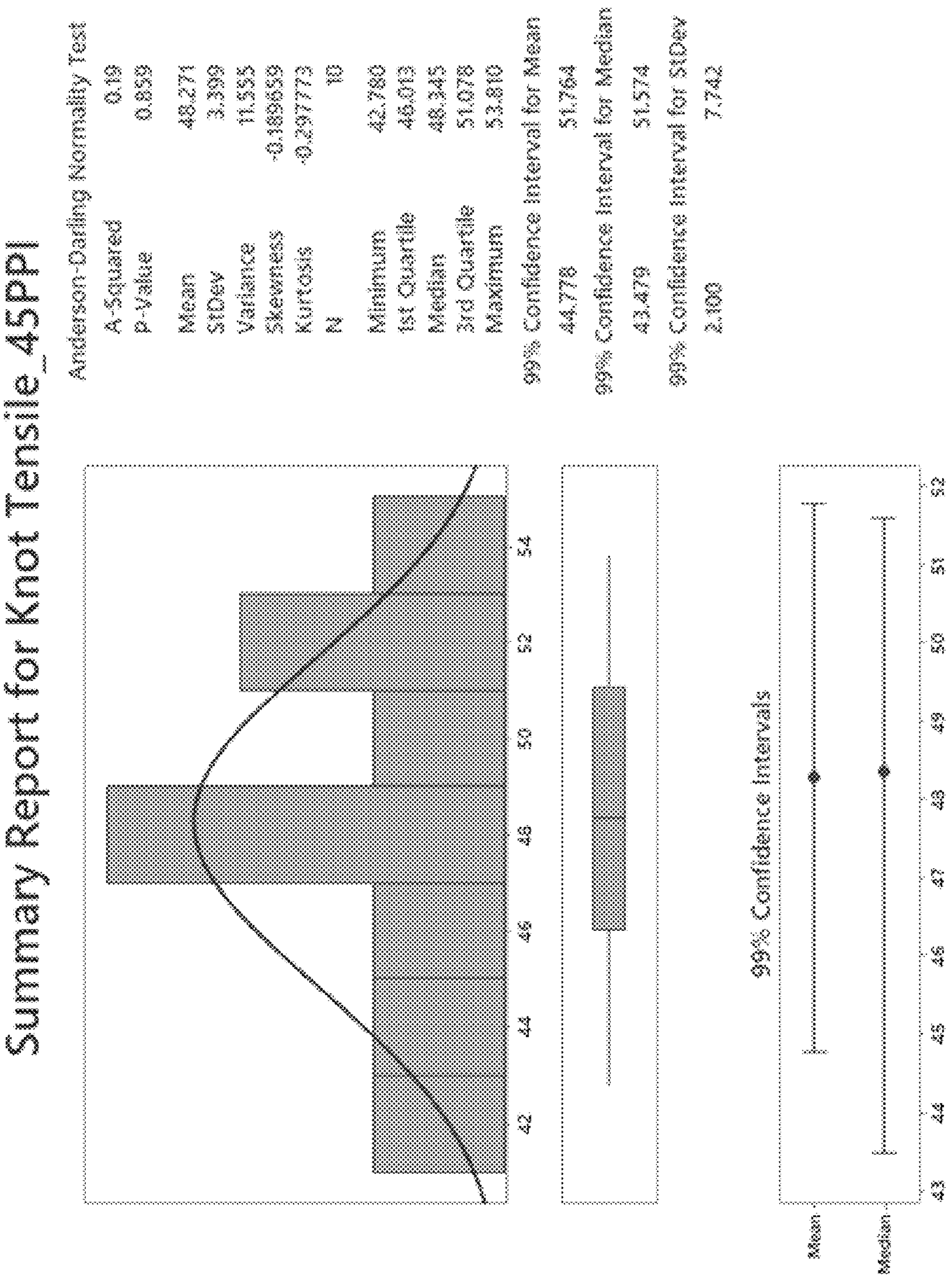
FIG. 43 is a summary report of knot tensile strength for a 2-0 suture braided at 45 PPI.

FIG. 43 is a summary report of knot tensile strength for a 2-0 suture braided at 45 PPI. The summary report indicates the results of an Anderson-Darling Normality Test for the diameter of the suture.

Figure 44:
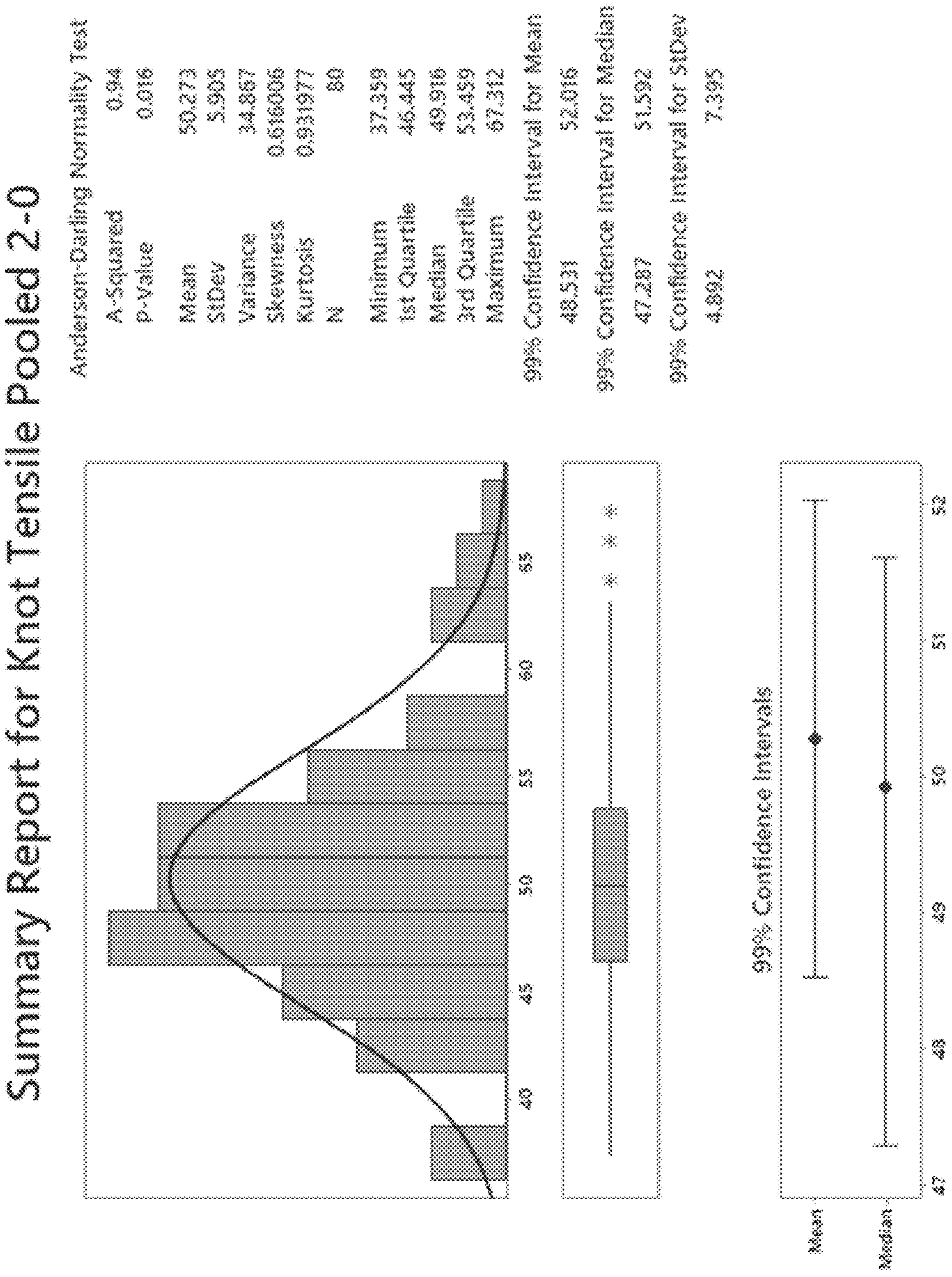
FIG. 44 is a summary report of knot tensile strength pooled for 2-0 suture braided at various PPI.

FIG. 44 is a summary report of knot tensile strength pooled for 2-0 suture braided at various PPI. The summary report indicates the results of an Anderson-Darling Normality Test for the diameter of the suture.

Figure 45:
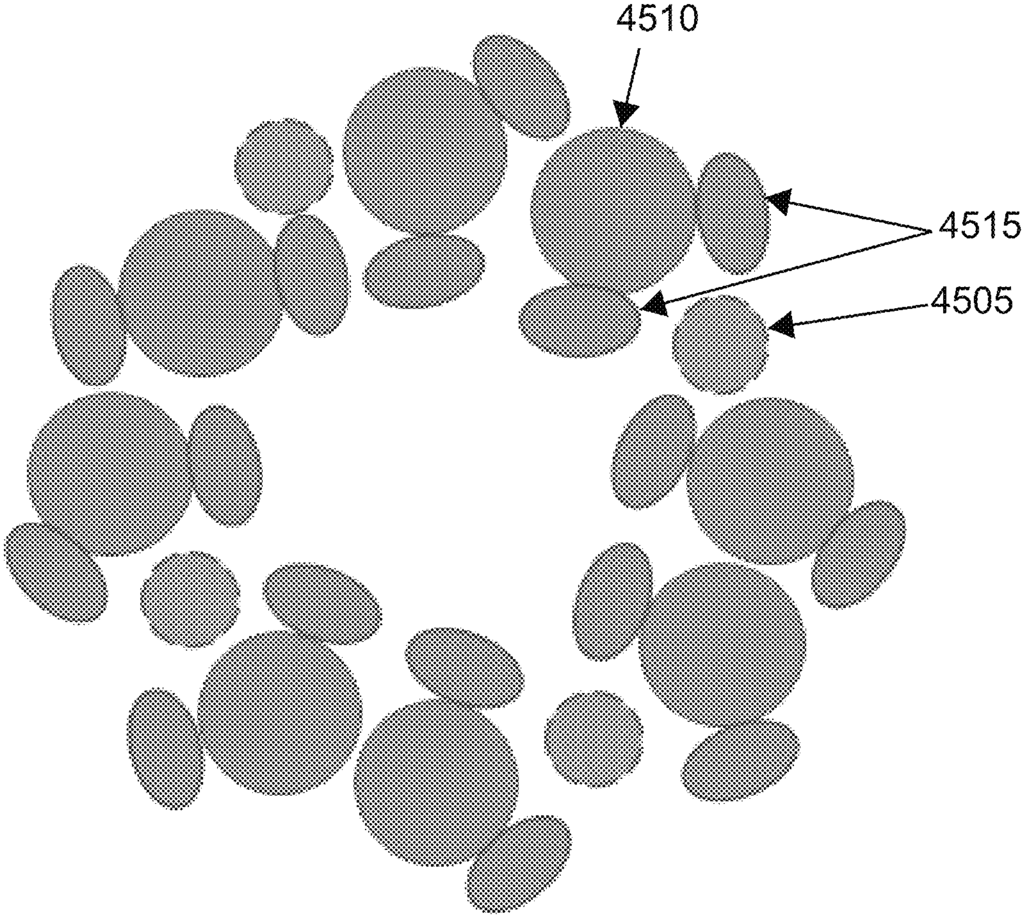
FIG. 45 is a schematic cross-sectional view of the fiber arrangement of a #2 suture formed of collagen-UHMWPE co-braid.

In addition, #2 round collagen-UHMWPE co-braided sutures were tested. FIG. 45 is a schematic cross-sectional view of the fiber arrangement of a #2 suture formed of collagen-UHMWPE co-braid. Again, it will be noted that this cross section generally illustrates the arrangement of fibers during manufacturing right before the fibers are wound about one another. As shown in FIG. 45, the co-braid includes a plurality of collagen fibers 4510, each wrapped with two smaller synthetic fibers 4515. In addition, separate smaller synthetic fibers 4505 are also part of the overall braid. It will be noted that this suture does not include a fiber core.

Thus, the tested #2 round braid was a 12-carrier braid, including 8 ends of 26FB collagen wrapped 2× with 55 dTex UHMWPE fibers, and including 4 ends of 55 dTex UHMWPE fibers. FIGS. 47-56 present the data obtained from testing of these sutures.

In some embodiments, some of the fibers may be prewound around other fibers prior to the braiding process. This enables more fibers to be incorporated into the braid without the need for an increased number of bobbins on the braiding machine. By increasing the number of fibers (and the overall linear length of fibers), greater strength of the braided material may be achieved. In addition, a greater number of fibers provides an increased variability in the properties achievable in manufacturing the braided material, particularly when one considers that the added prewound fibers may vary in size and/or material.

In some embodiments, synthetic fibers may be prewound around the collagen fibers before braiding forming subassemblies. This prewinding of synthetic fibers about the collagen fibers may reduce or prevent fraying of the collagen fibers during the braiding process. In some cases, the prewound synthetic fibers may have a smaller cross-sectional area (e.g., a smaller diameter) than the collagen fibers about which they are prewound. In addition, the synthetic fibers may be wound at approximately 4 turns per inch. The smaller size of the prewound synthetic fibers and the 4 turns per inch winding may leave a considerable surface area of the collagen fiber exposed for purposes of cell attachment, since cells attach much better to the collagen fibers than to the synthetic fibers. The addition of prewound synthetic fibers in a spaced apart winding pitch may strike a balance between adding strength, preventing fraying, and providing collagen exposure for cell attachment.

In some embodiments, the prewinding may be reversed, with one or more collagen fibers wrapped around a synthetic fiber. This provides an increase in collagen material in the braid, which facilitates cell attachment and ultimately adds strength without increasing the amount of material that stays behind beyond the resorption of the collagen fibers.

Figure 46:
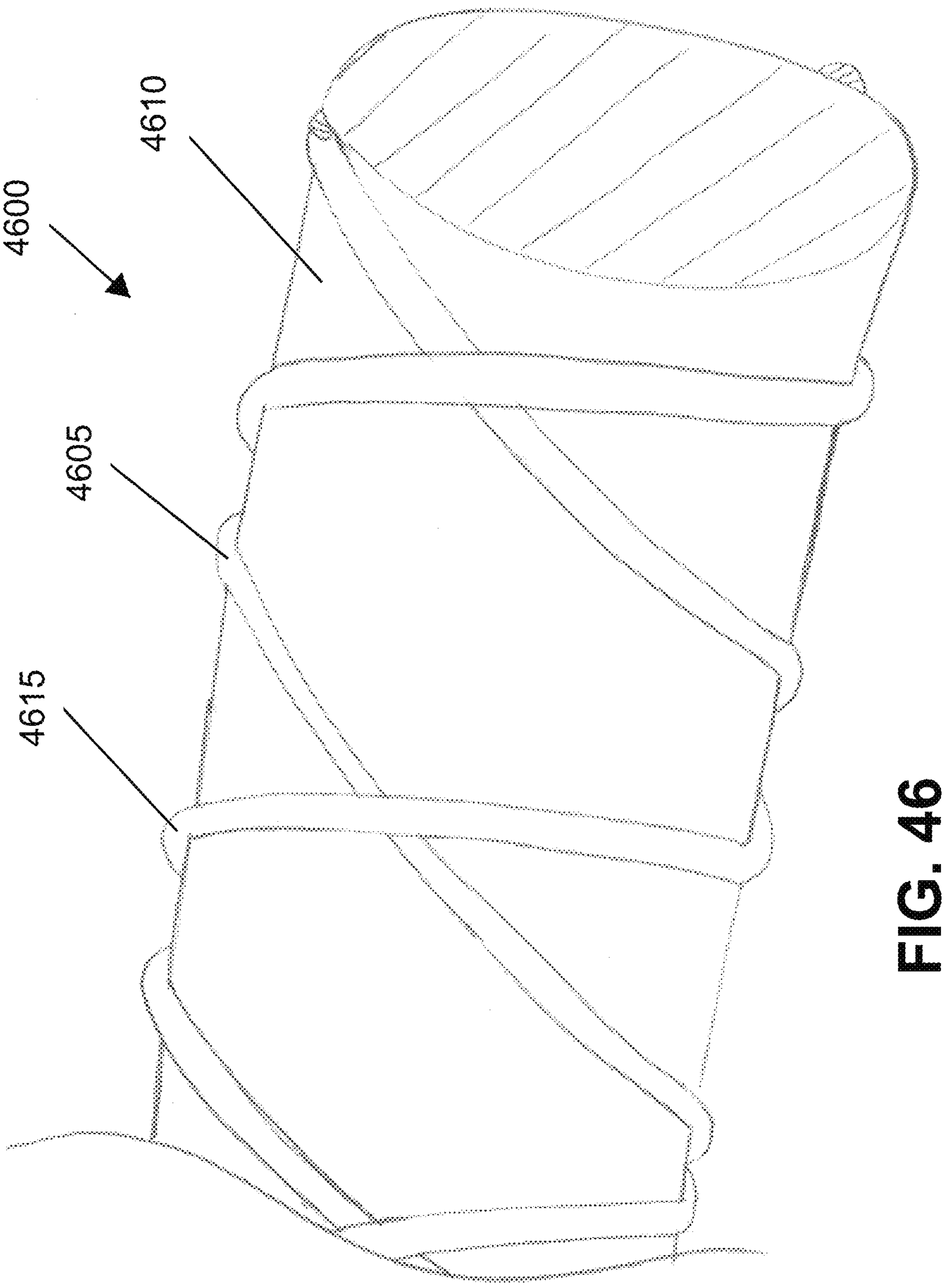
FIG. 46 is a schematic perspective view of a collagen fiber wrapped with two smaller synthetic fibers, the assembly being a subcomponent of a collagen-UHMWPE co-braid forming a #2 suture.

FIG. 46 is a schematic perspective view of a collagen fiber wrapped with two smaller synthetic fibers, the assembly being a subcomponent of a collagen-UHMWPE co-braid forming a #2 suture. As shown in FIG. 46, a subassembly 4600 includes a larger sized collagen fiber 4610 wrapped with a first smaller synthetic fiber 4605 and a second smaller synthetic fiber 4615. It will be understood that the components of FIG. 46 drawn schematically and that the size differential between the fibers may vary. In some embodiments, the smaller synthetic fibers may be wrapped at 4 turns per inch, thus leaving a large portion of the surface area of the collagen fiber 4610 exposed for cell attachment. It will be understood, however, that other pitches (besides 4 turns per inch) may be utilized that leave portions of the collagen fiber exposed.

Accordingly, the present disclosure is directed to a method of braiding a biopolymer scaffold. The method may include winding one or more synthetic fibers around a first high strength collagen fiber to form a first wound subassembly, and braiding the subassembly with two or more synthetic fibers. The method may further include winding one or more synthetic fibers around a second high strength collagen fiber to form a second subassembly, and braiding the first and second subassemblies with two or more synthetic fibers. In some embodiments, the method may include winding the one or more synthetic fibers around the first high strength collagen fiber at approximately 4 turns per inch.

Although the collagen fibers are suitably strong to withstand the braiding process, in some cases, the braiding technique can result in visual defects on some of the collagen fibers of a co-braid. Various braiding techniques were tested, revealing that certain braiding techniques result in fewer visual defects in the carbon strands.

FIG. 47 is a table showing Tukey pairwise comparisons of visual defects in #2 round sutures formed at various braiding settings. As shown, counterclockwise (CCW) winding and mixed winding was used to produce the different test samples. The mixed winding produced significantly fewer defects than the counterclockwise winding.

Figure 48:
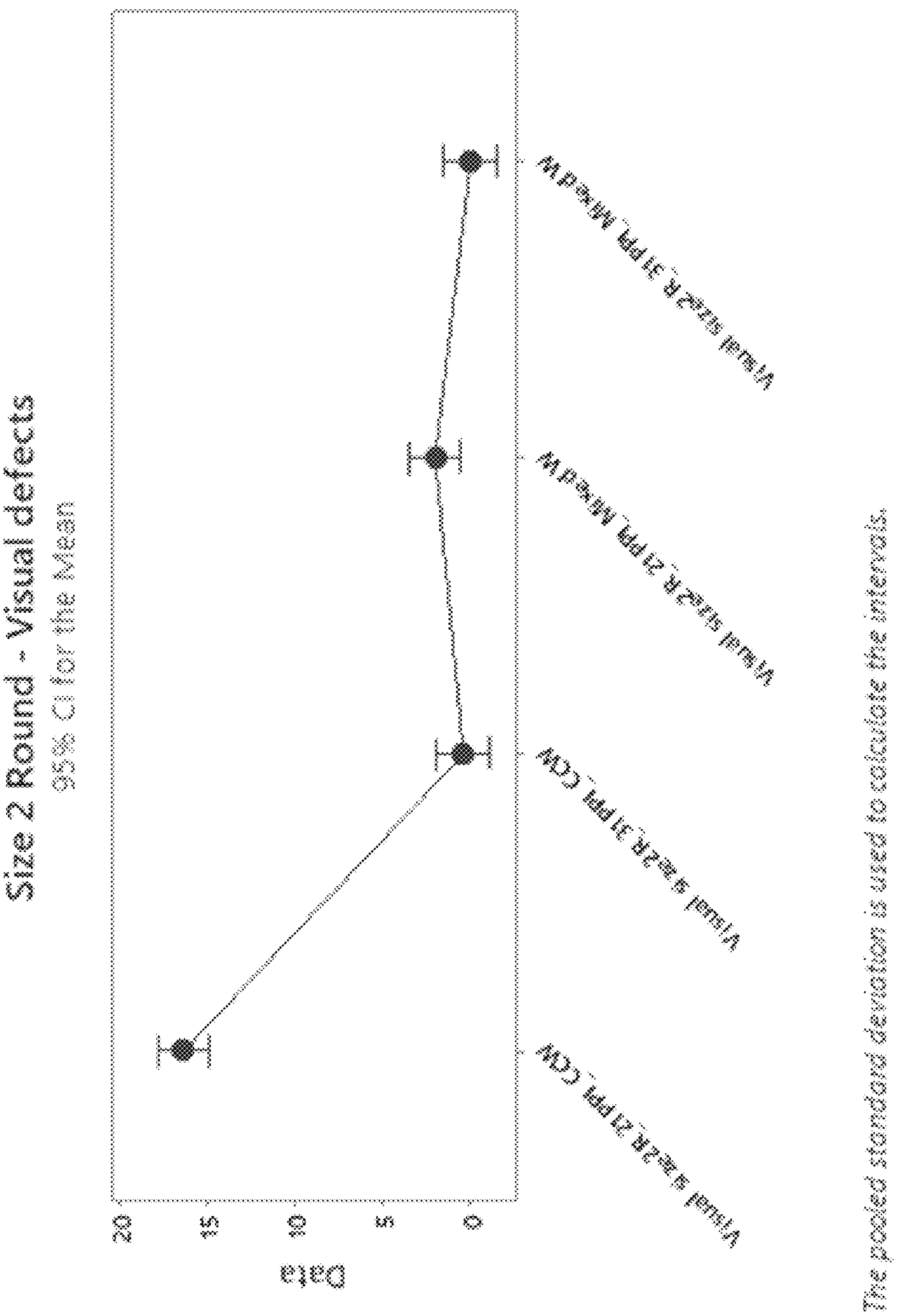
FIG. 48 is a graph plotting the data shown in the table of FIG. 41 with confidence intervals.

FIG. 48 is a graph plotting the data shown in the table of FIG. 47 with confidence intervals.

Figure 49:
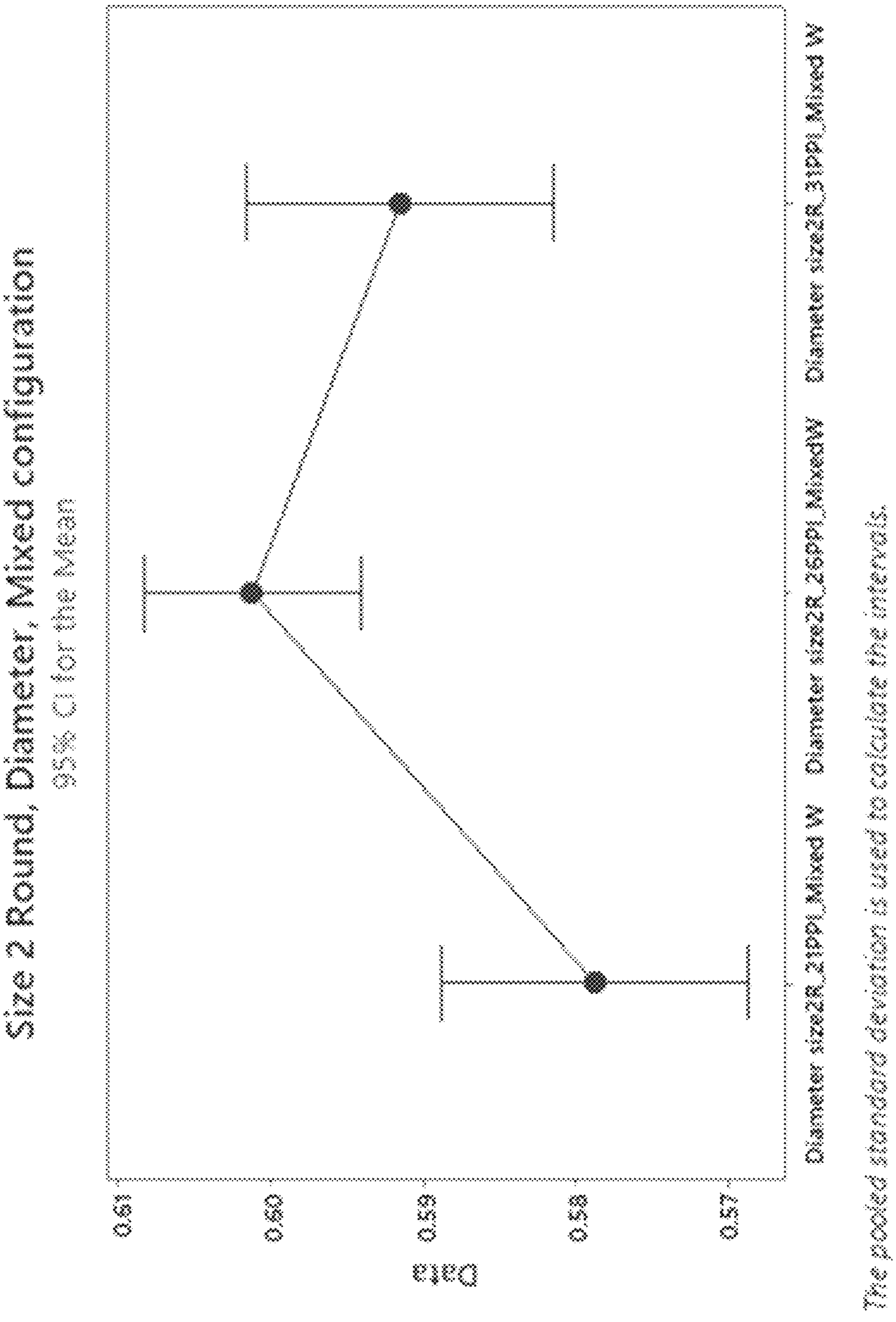
FIG. 49 is a graph showing the diameters of #2 round sutures braided at various settings.

FIG. 49 is a graph showing the diameters of #2 round sutures braided at various settings.

Figure 50:
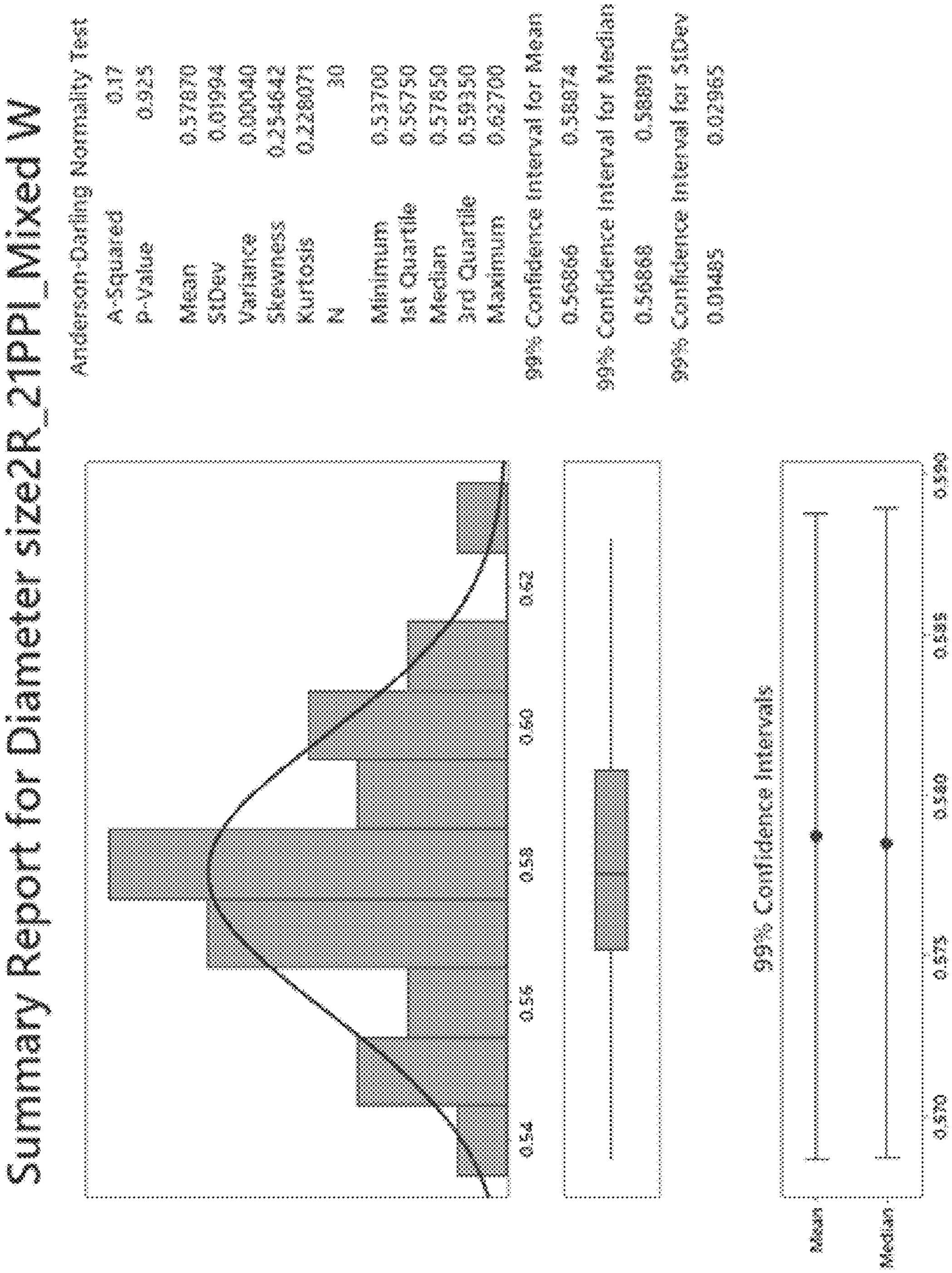
FIG. 50 is a summary report for the diameter of #2 round sutures braided at 21 PPI with mixed winding.

FIG. 50 is a summary report for the diameter of #2 round sutures braided at 21 PPI with mixed winding.

Figure 51:
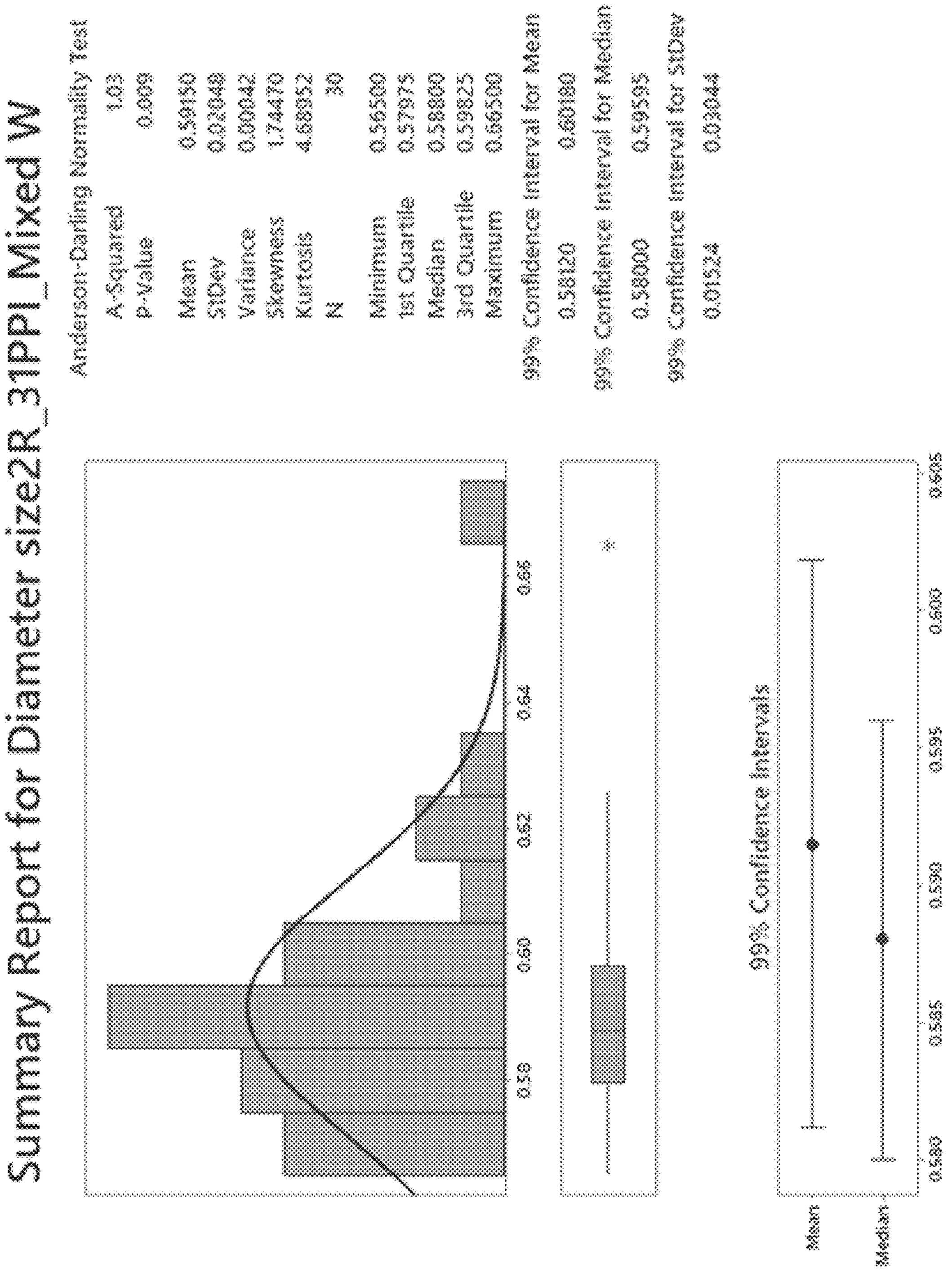
FIG. 51 is a summary report for the diameter of #2 round sutures braided at 31 PPI with mixed winding.

FIG. 51 is a summary report for the diameter of #2 round sutures braided at 31 PPI with mixed winding.

Figure 52:
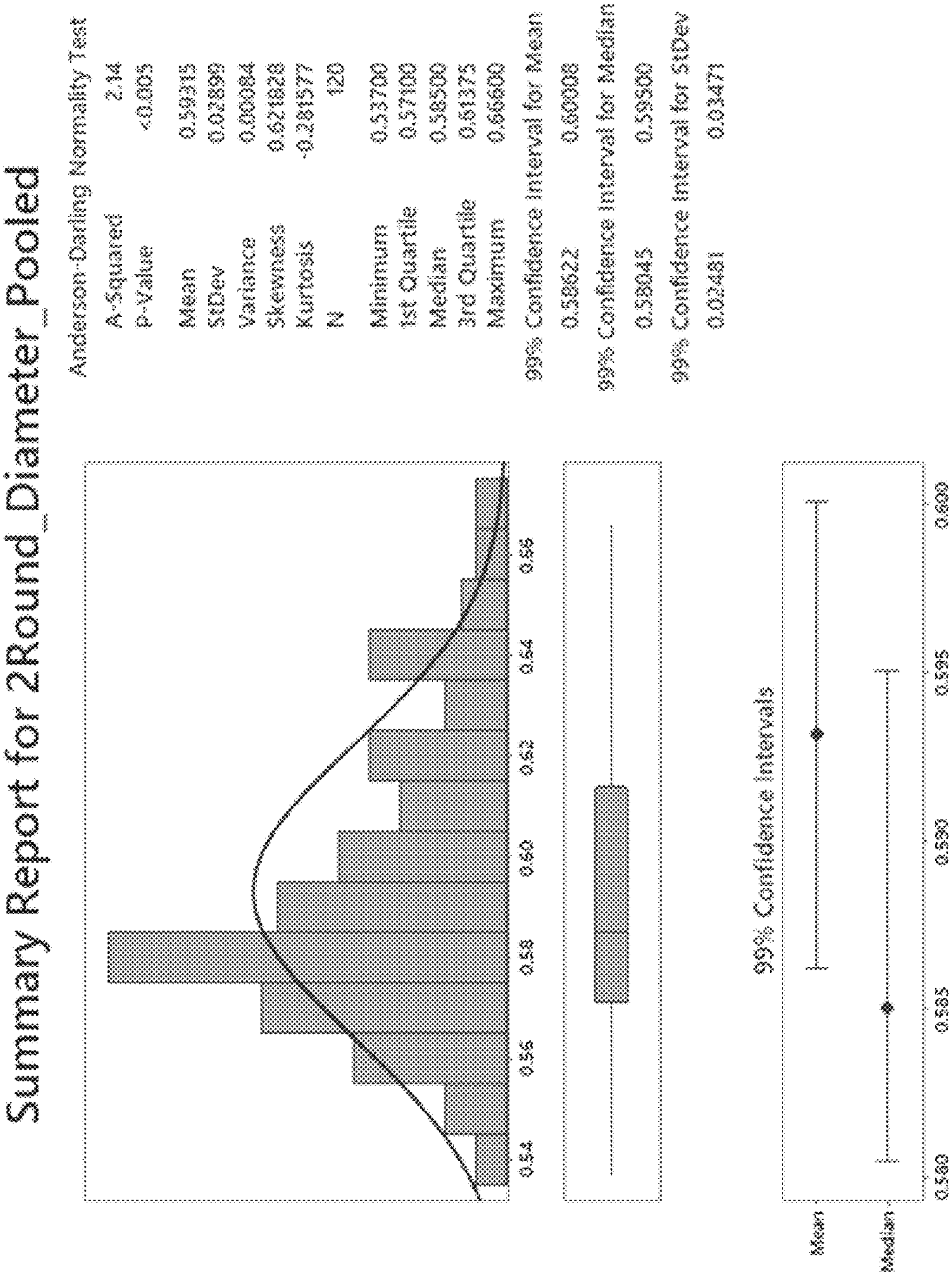
FIG. 52 is a summary report for the pooled diameter of #2 round sutures braided at various braiding settings.

FIG. 52 is a summary report for the pooled diameter of #2 round sutures braided at various braiding settings.

Figure 53:
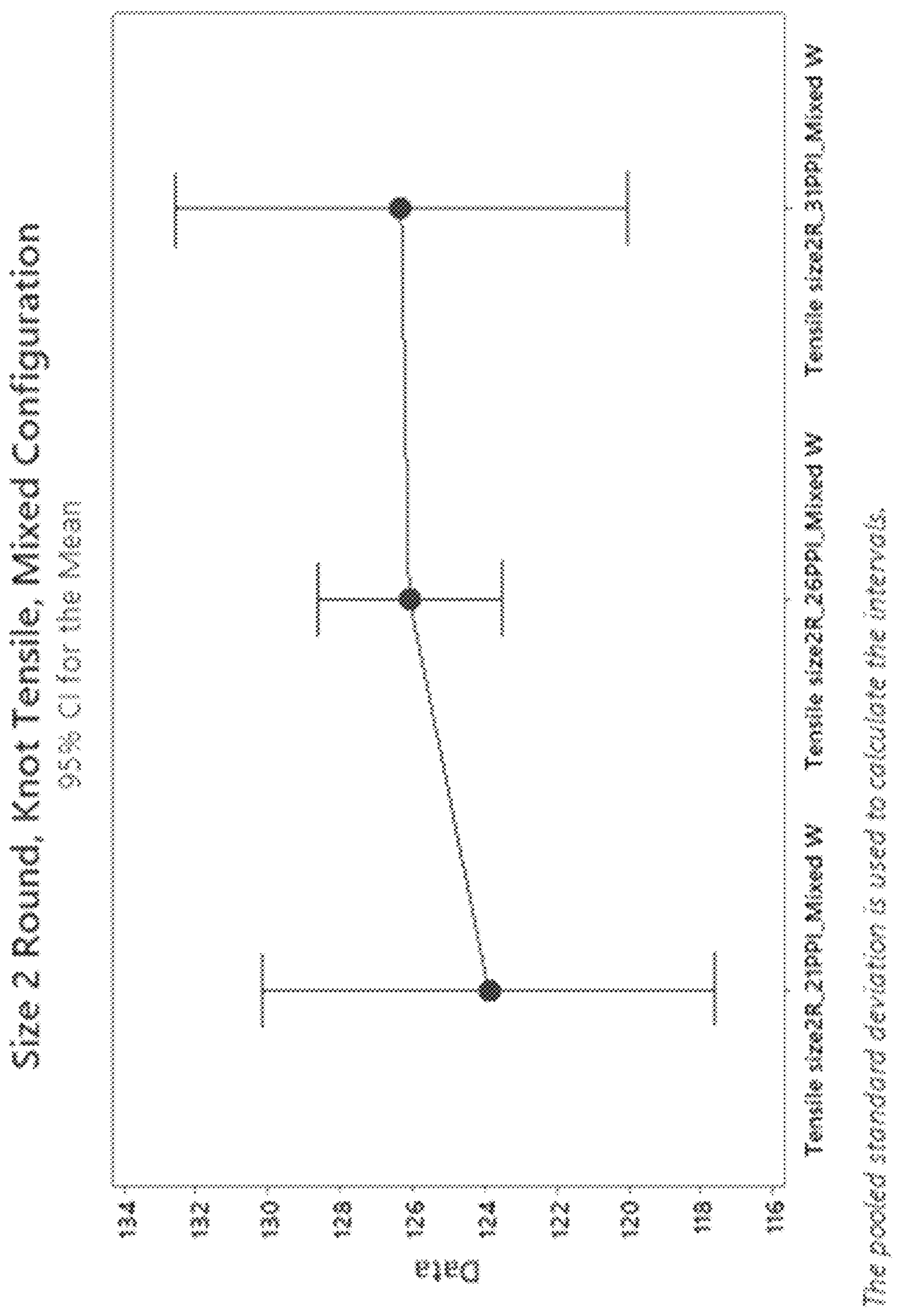
FIG. 53 is a confidence interval plot of knot tensile strength for #2 round sutures braided at various PPI.

FIG. 53 is a confidence interval plot of knot tensile strength for #2 round sutures braided at various PPI.

Figure 54:
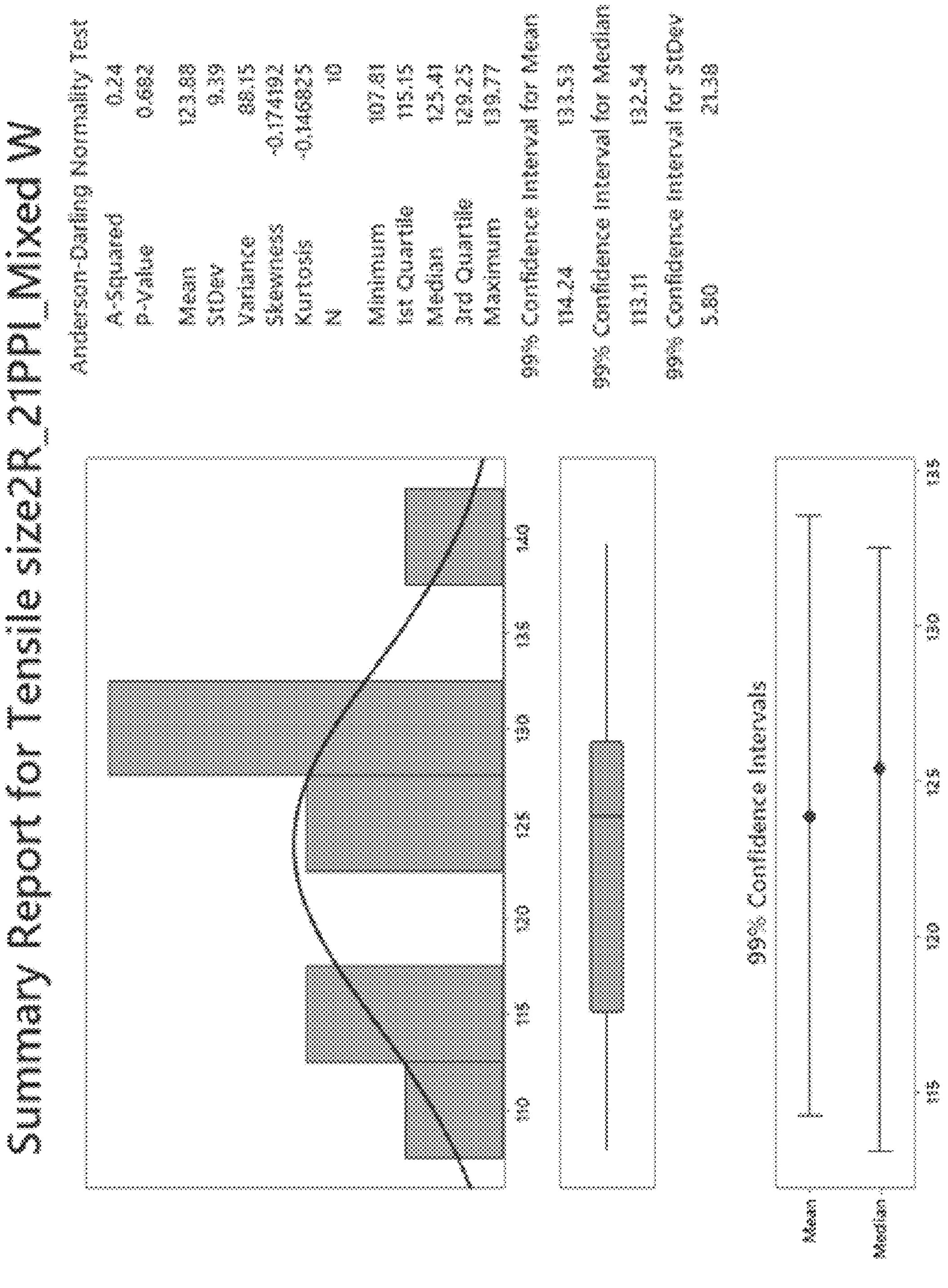
FIG. 54 is a summary report of knot tensile strength for a #2 round suture braided at 21 PPI with mixed winding.

FIG. 54 is a summary report of knot tensile strength for a #2 round suture braided at 21 PPI with mixed winding.

Figure 55:
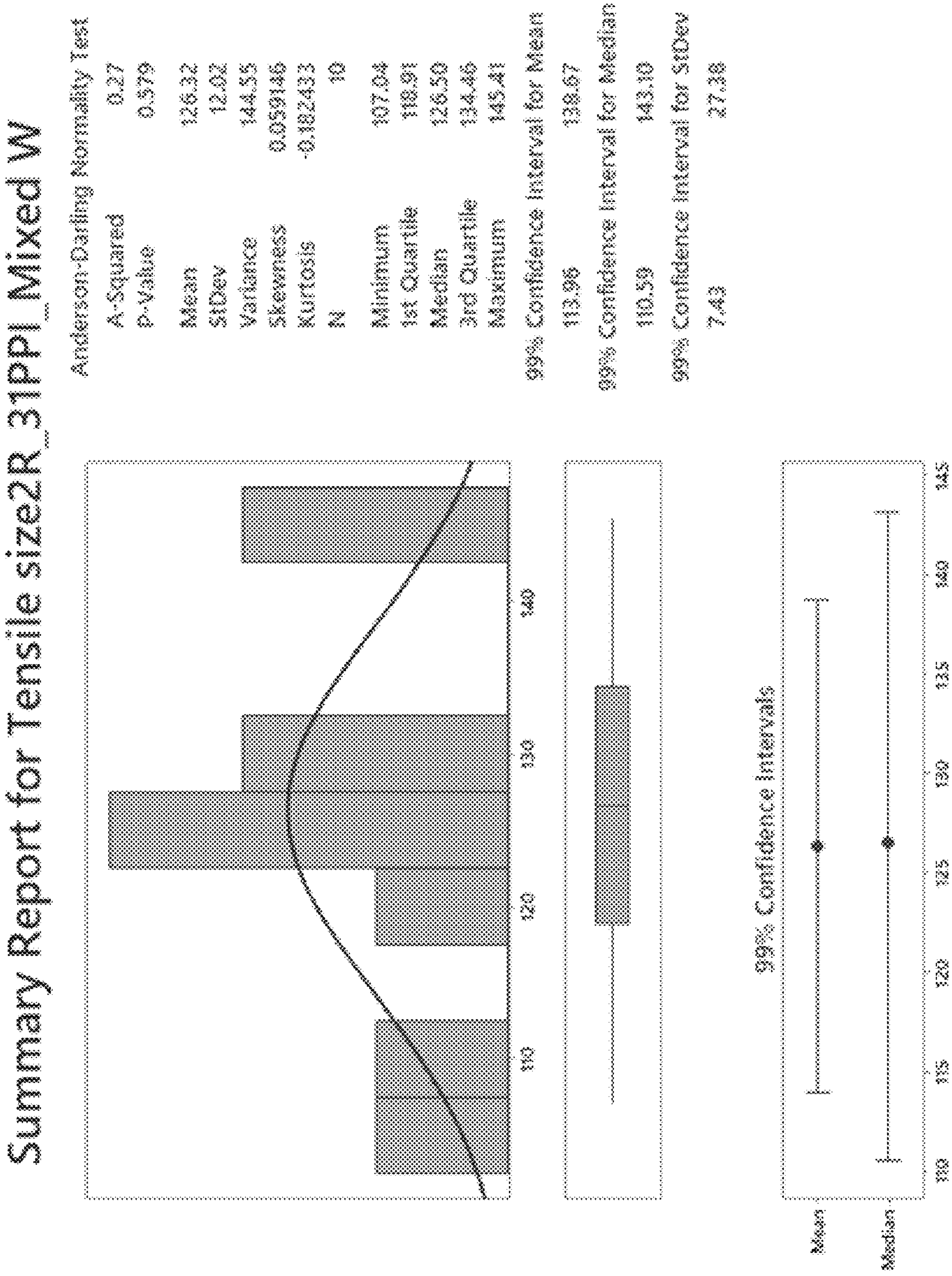
FIG. 55 is a summary report of knot tensile strength for a #2 round suture braided at 31 PPI with mixed winding.

FIG. 55 is a summary report of knot tensile strength for a #2 round suture braided at 31 PPI with mixed winding.

Figure 56:
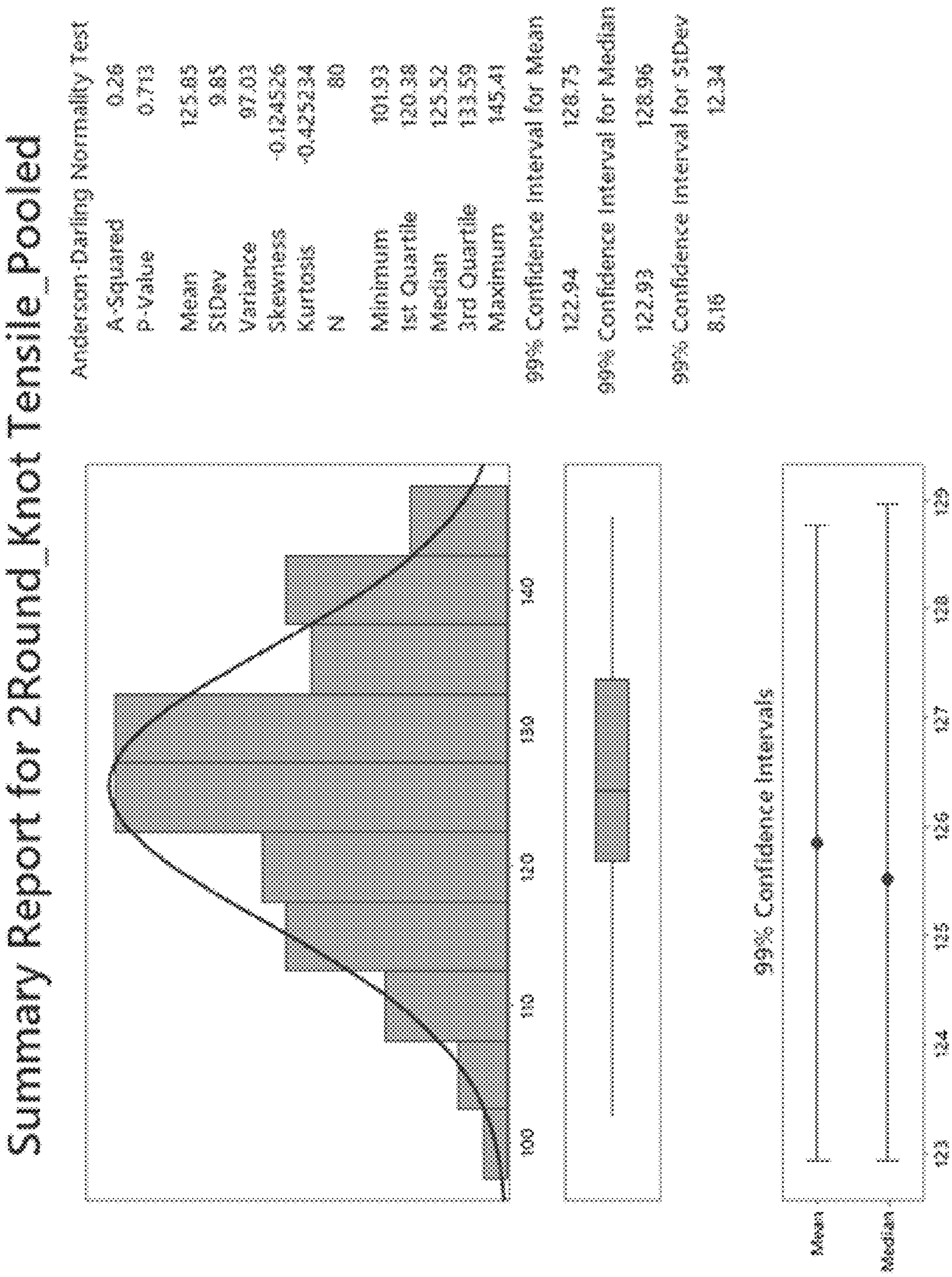
FIG. 56 is a summary report for the pooled knot tensile strength of #2 round sutures braided at various braiding settings.

FIG. 56 is a summary report for the pooled knot tensile strength of #2 round sutures braided at various braiding settings.

Figure 57:
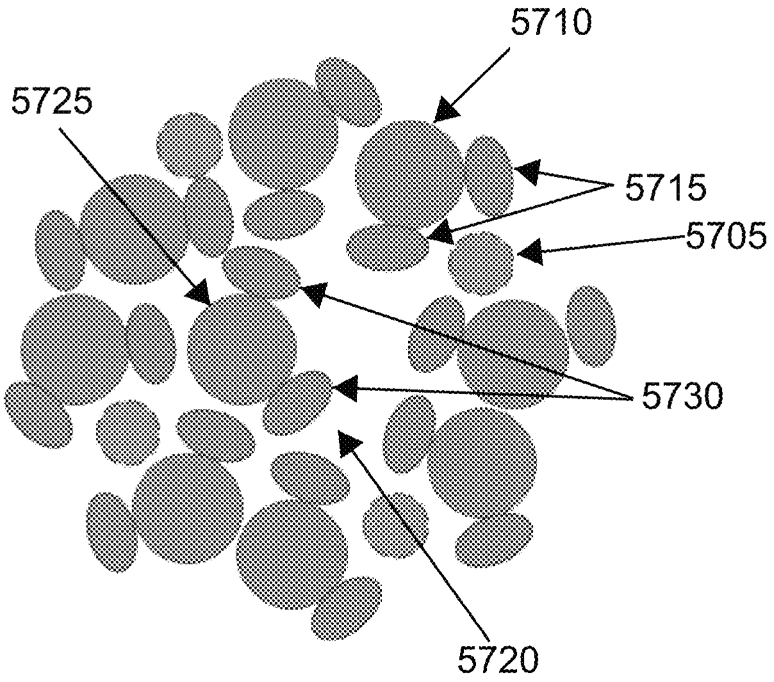
FIG. 57 is a schematic cross-sectional view of the fiber arrangement of the round end portion of a size 1.5 mm Suture Tape formed of collagen-UHMWPE co-braid.

Also, 1.5 mm Suture Tape collagen-UHMWPE co-braided sutures were tested. FIG. 57 is a schematic cross-sectional view of the fiber arrangement of the round end portion(s) of 1.5 mm Suture Tape formed of collagen-UHMWPE co-braid. As shown in FIG. 57, a plurality of collagen fibers 5710 are each wound with two synthetic fibers 5715 (see FIG. 46). In addition, separate synthetic fibers 5705 are also part of the braided arrangement. In addition, this co-braid includes a core structure 5720 formed of a collagen core fiber 5725 and two synthetic fibers 5730.

Figure 58:
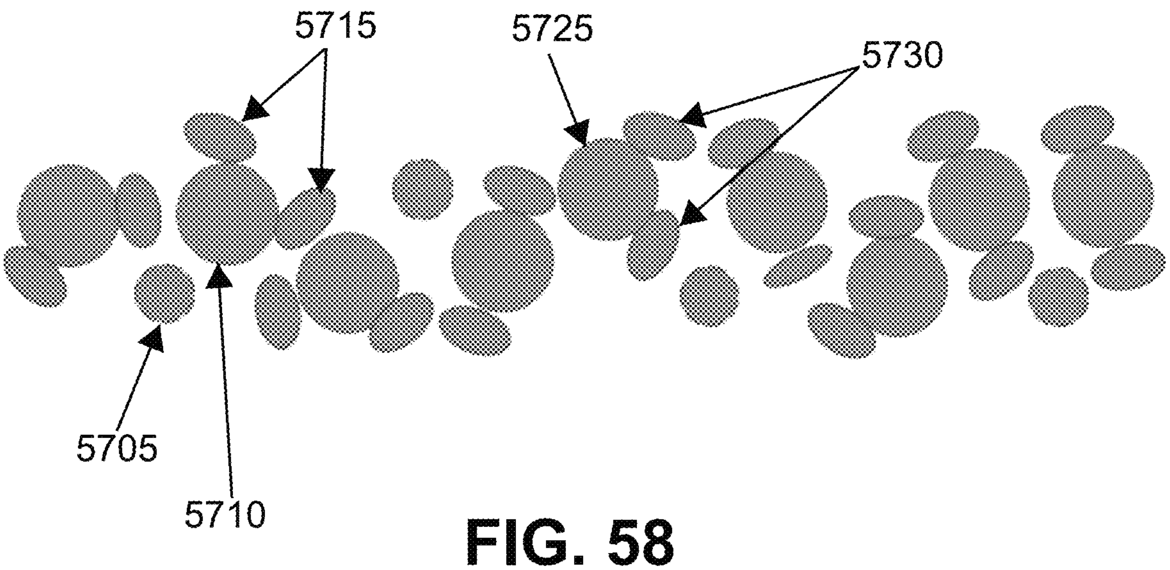
FIG. 58 is a schematic cross-sectional view of the fiber arrangement of the flat central portion of a size 1.5 mm Suture Tape formed of collagen-UHMWPE co-braid.

FIG. 58 is a schematic cross-sectional view of the fiber arrangement of the flat central portion of a 1.5 mm Suture Tape formed of collagen-UHMWPE co-braid.

Figure 59:
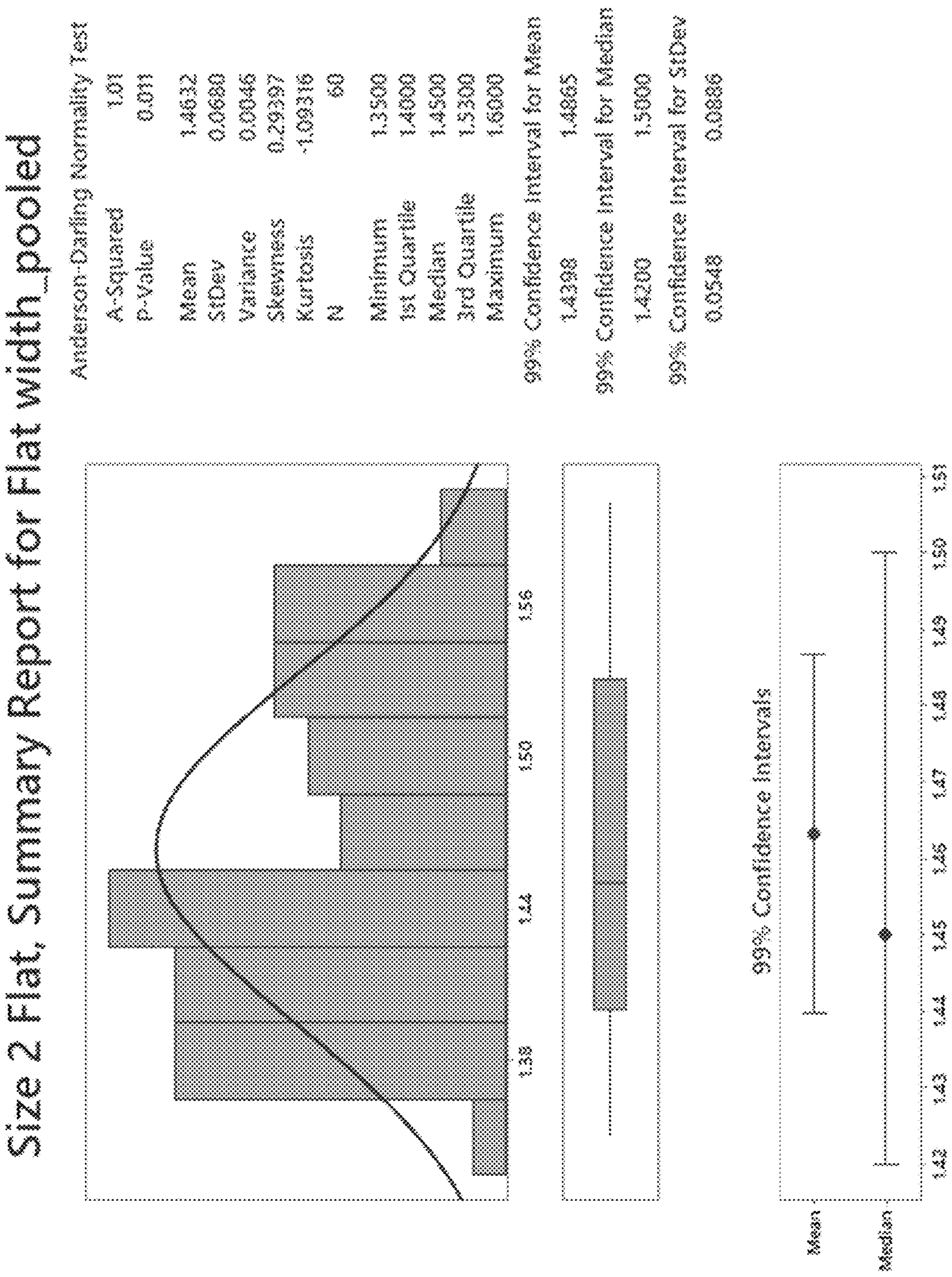
FIG. 59 is a summary report for the pooled width of size 1.5 mm Suture Tape braided at various braiding settings.
Figure 60:
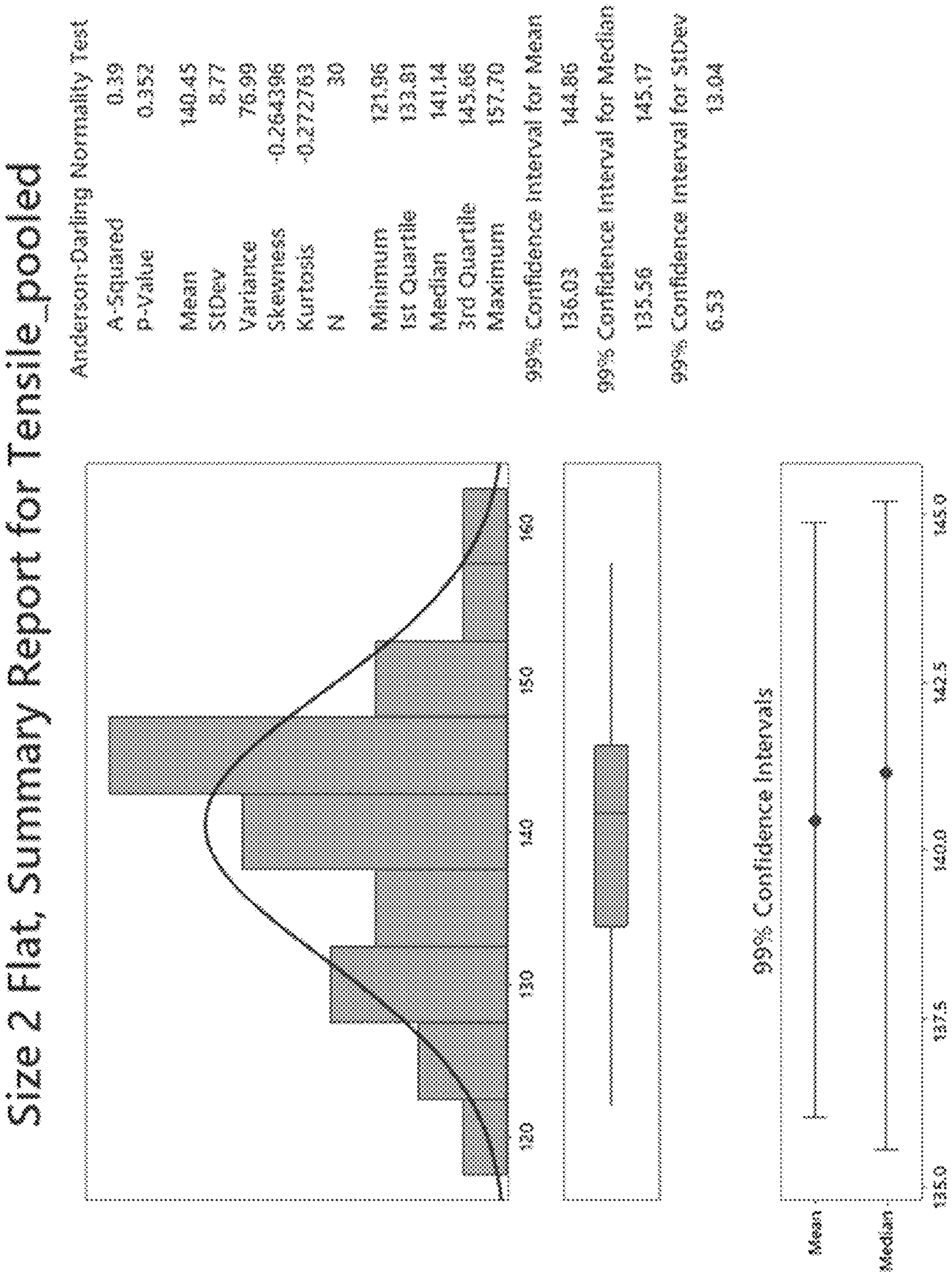
FIG. 60 is a summary report for the pooled knot tensile strength of size 1.5 mm Suture Tape braided with various braiding settings.

The tested 1.5 mm Suture Tape was a 13-carrier braid including 9 ends of 26FB collagen wrapped with 2× dTex UHMWPE fibers, and including 4 ends of 55 dTex UHMWPE fibers. FIGS. 59-60 present the data obtained from diameter and knot tensile strength testing of these sutures.

FIG. 59 is a summary report for the pooled width of size 1.5 mm Suture Tape braided at various braiding settings.

FIG. 60 is a summary report for the pooled knot tensile strength of 1.5 mm Suture Tape braided with various braiding settings.

Figure 61:
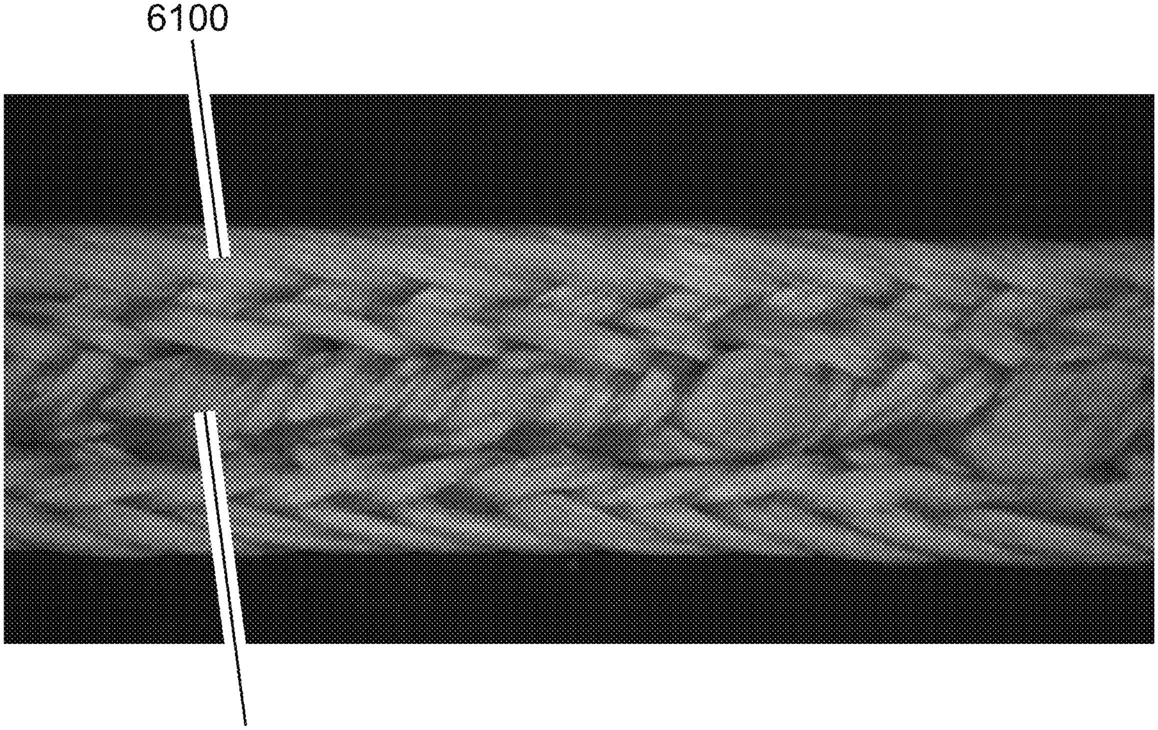
FIG. 61 is an image of a 2.5 mm Suture Tape formed of collagen-UHMWPE co-braid.

In addition, 2.5 mm Suture Tape collagen-UHMWPE co-braided suture was tested. FIG. 61 is an image of a 2.5 mm Suture Tape formed of collagen-UHMWPE co-braid. As shown in FIG. 61, this suture may include collagen fibers wrapped with synthetic fibers. This blend 6100 forms the periphery of the Tape suture. In addition, as also shown in FIG. 61, this suture may include a core 6105 that forms an axial braid.

The tested 2.5 mm Suture Tape was a 17-carrier braid plus 16-carrier braid core. The 17 carriers included 11 ends of 26FB collagen wrapped 1× with 55 dTex UHMWPE fibers, and 6 ends of 26FB collagen wrapped 2× with 55 dTex UHMWPE fibers. FIGS. 53 and 54 illustrate the findings of this testing. In particular, width testing and knot tensile strength testing was performed.

Figure 62:
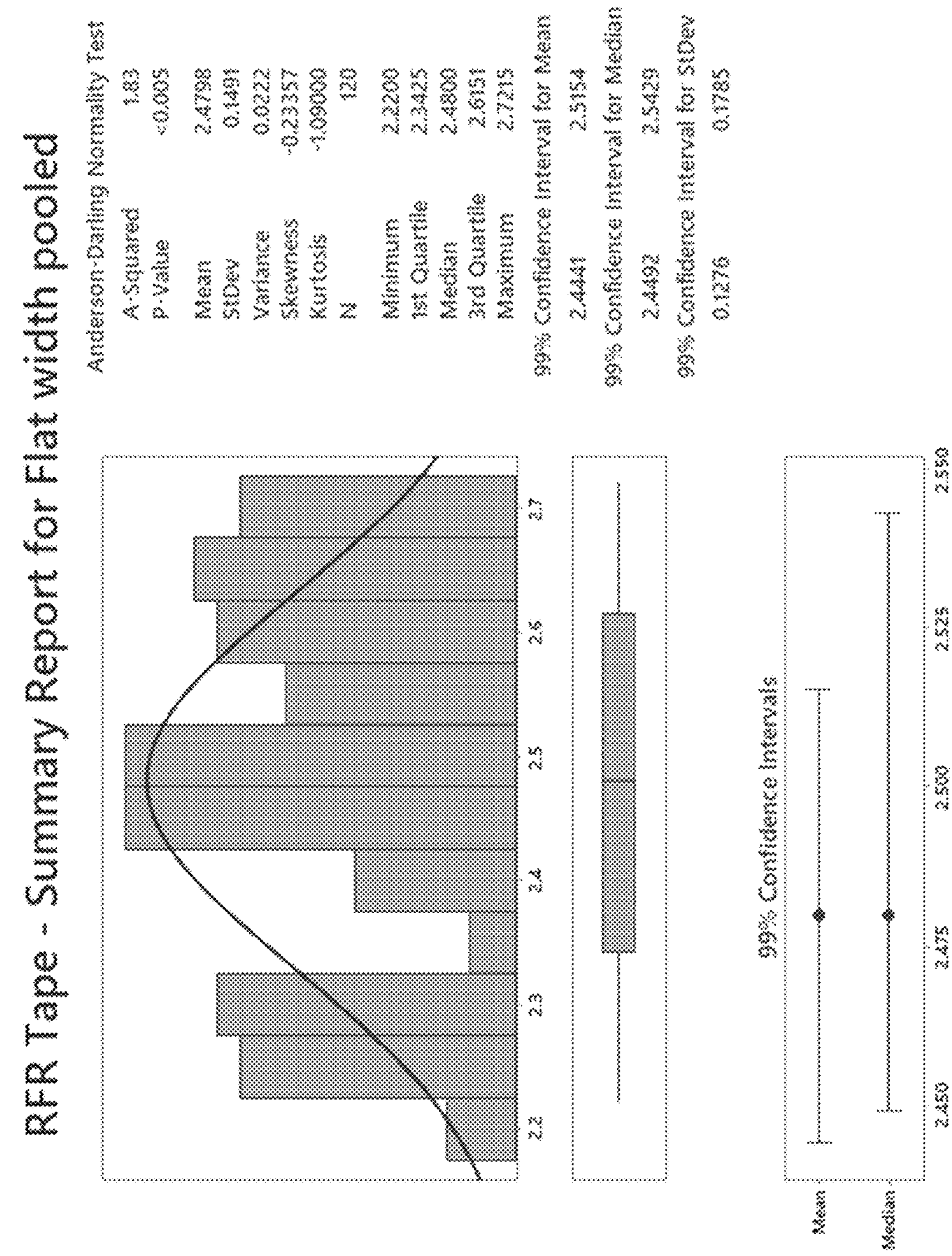
FIG. 62 is a summary report for pooled with of 2.5 mm Suture Tape braided at various braiding settings.

FIG. 62 is a summary report for pooled width of 2.5 mm Suture Tape braided at various braiding settings.

Figure 63:
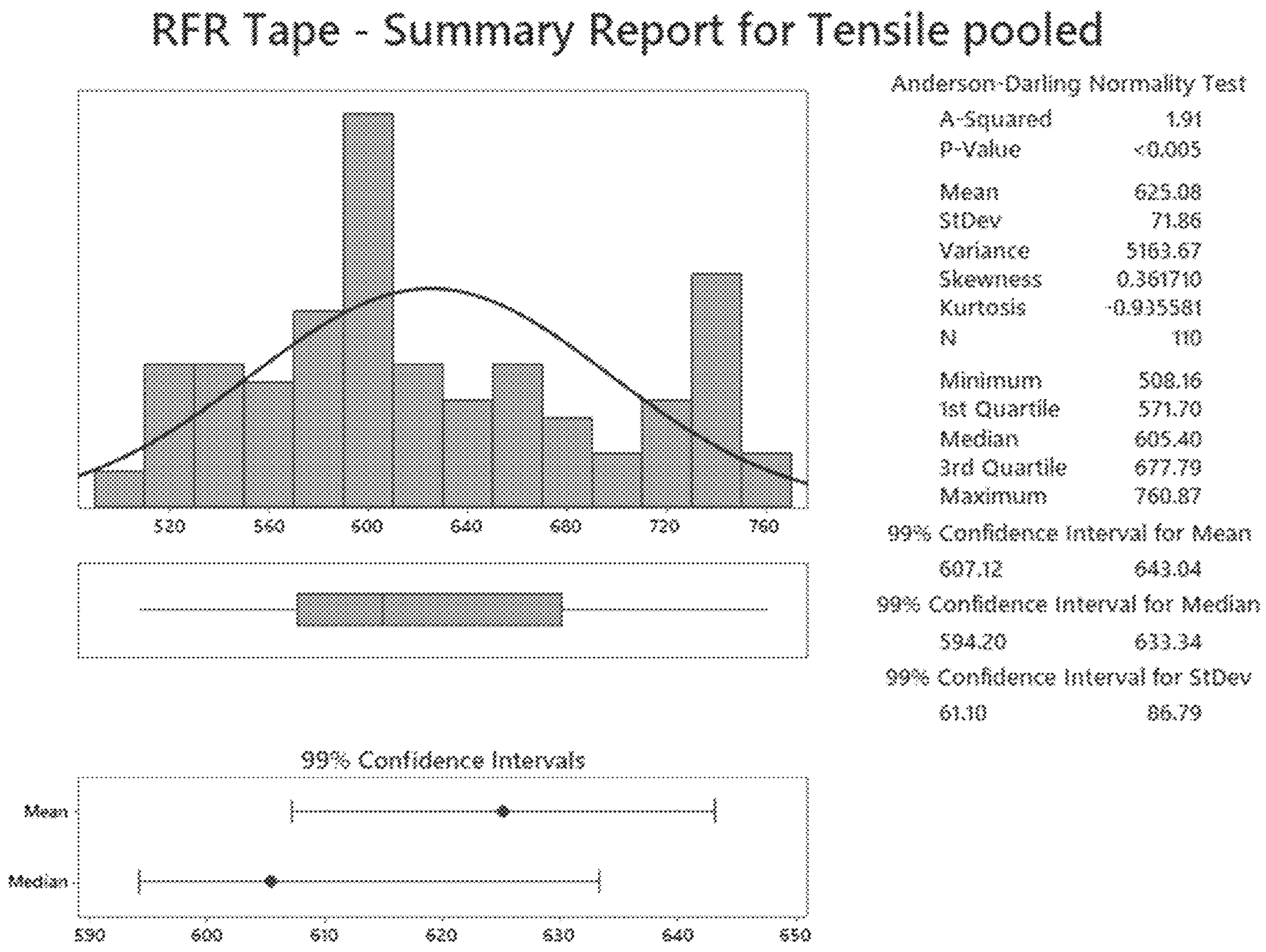
FIG. 63 is a summary report for the pooled knot tensile strength of 2.5 mm Suture Tape braided at various braiding settings.

FIG. 63 is a summary report for the pooled knot tensile strength of 2.5 mm Suture Tape braided at various braiding settings.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A braided construct, comprising:

a first winded subassembly braided together with at least a second winded subassembly, wherein, prior to the first winded subassembly being braided together with the second winded subassembly, the first winded subassembly is comprised of at least a first high-strength polyethylene fiber winded around a first high-strength collagen fiber in a clockwise direction and a second high-strength polyethylene fiber winded around the first high-strength collagen fiber in a counterclockwise direction such that the first high-strength polyethylene fiber and the second high-strength polyethylene fiber repeatedly cross one another while extending in a longitudinal direction along the first high-strength collagen fiber, and wherein the first high-strength polyethylene fiber crosses over but not under the second high-strength polyethylene fiber while extending in the longitudinal direction along the first high-strength collagen fiber, and wherein the second high-strength polyethylene fiber crosses under but not over the first high-strength polyethylene fiber while extending in the longitudinal direction along the first high-strength collagen fiber, wherein, prior to the first winded subassembly being braided together with the second winded subassembly, the second winded subassembly is comprised of at least a third high-strength polyethylene fiber winded around a second high-strength collagen fiber in the clockwise direction and a fourth high-strength polyethylene fiber winded around the second high-strength collagen fiber in the counterclockwise direction such that the third high-strength polyethylene fiber and the fourth high-strength polyethylene fiber repeatedly cross one another while extending in the longitudinal direction along the second high-strength collagen fiber, and wherein the third high-strength polyethylene fiber crosses over but not under the fourth high-strength polyethylene fiber while extending in the longitudinal direction along the second high-strength collagen fiber, and wherein the fourth high-strength polyethylene fiber crosses under but not over the third high-strength polyethylene fiber while extending in the longitudinal direction along the second high-strength collagen fiber.

2. The braided strand of claim 1, wherein, prior to the first winded subassembly being braided together with the second winded subassembly, the first high-strength polyethylene fiber and the second high-strength polyethylene fiber are the only two fibers winded around the first high-strength collagen fiber.

3. The braided strand of claim 1, wherein the first high-strength polyethylene fiber and the second high-strength polyethylene fiber are winded around the first high-strength collagen fiber at a pitch expressed as a number of turns per inch.

4. The braided strand of claim 1 further comprising at least a first additional synthetic fiber braided together with the first winded subassembly and the second winded subassembly.

5. A braided construct, comprising:

a number of winded subassemblies braided together with a number of additional synthetic fibers, wherein the number of winded subassemblies is greater than the number of additional synthetic fibers, wherein the number of winded subassemblies includes a first winded subassembly, wherein, prior to the number of winded subassemblies being braided together with the number of additional synthetic fibers, the first winded subassembly includes at least a first high-strength polyethylene fiber winded around a first high-strength collagen fiber in a clockwise direction and a second high-strength polyethylene fiber winded around the first high-strength collagen fiber in a counterclockwise direction such that the first high-strength polyethylene fiber and the second high-strength polyethylene fiber repeatedly cross one another while extending in a longitudinal direction along the first high-strength collagen fiber, and wherein the first high-strength polyethylene fiber crosses over but not under the second high-strength polyethylene fiber while extending in the longitudinal direction along the first high-strength collagen fiber, and wherein the second high-strength polyethylene fiber crosses under but not over the first high-strength polyethylene fiber while extending in the longitudinal direction along the first high-strength collagen fiber.

6. The braided construct of claim 5, wherein the first high-strength collagen fiber has a larger diameter than either of the first high-strength polyethylene fiber and the second high-strength polyethylene fiber.

7. The braided construct of claim 5, wherein the first high-strength polyethylene fiber is winded around the first high-strength collagen fiber at a pitch expressed as a number of turns per inch.

8. The braided construct of claim 5, wherein the number of additional synthetic fibers is greater than 1.

9. The braided construct of claim 5 forming a 13-carrier braid in which the number of winded subassemblies is 9 and the number of additional synthetic fibers is 4.

10. A braided construct, comprising:

at least a first winded subassembly braided together with at least one additional synthetic fiber, wherein, prior to the first winded subassembly being braided together with the at least one additional synthetic fiber, the first winded subassembly includes a first high-strength polyethylene fiber winded around a first high-strength collagen fiber in a clockwise direction and a second high-strength polyethylene fiber winded around the first high-strength collagen fiber in a counterclockwise direction such that the first high-strength polyethylene fiber and the second high-strength polyethylene fiber repeatedly cross one another while extending in a longitudinal direction along the first high-strength collagen fiber, and wherein the first high-strength polyethylene fiber crosses over but not under the second high-strength polyethylene fiber while extending in the longitudinal direction along the first high-strength collagen fiber, and wherein the second high-strength polyethylene fiber crosses under but not over the first high-strength polyethylene fiber while extending in the longitudinal direction along the first high-strength collagen fiber.

11. The braided construct of claim 10, wherein, prior to the first winded subassembly being braided together with the at least one additional synthetic fiber, the first high-strength polyethylene fiber and the second high-strength polyethylene fiber are the only two fibers winded around the first high-strength collagen fiber.

12. The braided construct of claim 10 braided around a braided synthetic core.

13. The braided construct of claim 10, wherein the first high-strength collagen fiber has a larger diameter than either of the first high-strength polyethylene fiber and the second high-strength polyethylene fiber.

14. The braided construct of claim 10, wherein the first high-strength polyethylene fiber and the second high-strength polyethylene fiber are winded around the first high-strength collagen fiber at a pitch expressed as a number of turns per inch.

15. The braided construct of claim 14, wherein the first high-strength polyethylene fiber and the second high-strength polyethylene fiber are winded around the first high-strength collagen fiber at approximately 4 turns per inch.

16. The braided construct of claim 10 also including a second winded subassembly braided together with the first winded subassembly and the at least one additional synthetic fiber, wherein, prior to the second winded subassembly being braided together with the first winded subassembly and the at least one additional synthetic fiber, the second winded subassembly includes a third high-strength polyethylene fiber winded around a second high-strength collagen fiber.

17. The braided construct of claim 16, wherein the second winded subassembly also includes a fourth high-strength polyethylene fiber winded around the second high-strength collagen fiber.

18. The braided construct of claim 10 comprising the first winded subassembly braided together with at least two additional synthetic fibers.

19. The braided construct of claim 10, wherein, prior to the first winded subassembly being braided together with the at least one additional synthetic fiber, the first high-strength collagen fiber is unbraided.

20. The braided construct of claim 10, wherein, prior to the first winded subassembly being braided together with the at least one additional synthetic fiber, the first winded subassembly includes the first high-strength polyethylene fiber and the second high-strength polyethylene fiber winded around a plurality of high-strength collagen fibers in the clockwise direction and the counterclockwise direction, respectively, and wherein the plurality of high-strength collagen fibers includes the first high-strength collagen fiber.

* * * * *